(12) United States Patent
Aissaoui et al.

(10) Patent No.: US 7,375,227 B2
(45) Date of Patent: May 20, 2008

(54) QUINOLINE DERIVATIVES

(75) Inventors: Hamed Aissaoui, Purlversheim (FR); Christoph Binkert, Basel (CH); Martine Clozel, Binningen (CH); Boris Mathys, Egerkingen (CH); Claus Mueller, Hegenheim (FR); Oliver Nayler, Arlesheim (CH); Michael Scherz, Ettingen (CH); Jörg Velker, Lörrach (DE); Thomas Weller, Binningen (CH)

(73) Assignee: Actelion Pharmaceuticals Ltd. (CH)

( * ) Notice: Subject to any disclaimer, the term of this patent is extended or adjusted under 35 U.S.C. 154(b) by 566 days.

(21) Appl. No.: 10/501,054

(22) PCT Filed: Dec. 2, 2002

(86) PCT No.: PCT/EP02/13577

§ 371 (c)(1),
(2), (4) Date: Sep. 15, 2004

(87) PCT Pub. No.: WO03/048154

PCT Pub. Date: Jun. 12, 2003

(65) Prior Publication Data

US 2005/0043535 A1     Feb. 24, 2005

(30) Foreign Application Priority Data

Dec. 4, 2001     (EP)     ............. PCT/EP01/14195

(51) Int. Cl.
*C07D 215/38*     (2006.01)
*C07D 215/44*     (2006.01)
(52) U.S. Cl. ........................... 546/157; 546/163
(58) Field of Classification Search ........... 546/157, 546/163
See application file for complete search history.

(56) References Cited

FOREIGN PATENT DOCUMENTS

| | | |
|---|---|---|
| EP | 0 428 434 | 5/1991 |
| WO | WO 99/21835 | 5/1999 |
| WO | WO 01/09088 | 2/2001 |
| WO | WO 01/45694 | 6/2001 |
| WO | WO-01/45700 A1 | 6/2001 |
| WO | WO-01/45711 A1 | 6/2001 |
| WO | WO 01/66143 | 9/2001 |
| WO | WO 02/02530 | 1/2002 |
| WO | WO 02/47687 | 6/2002 |
| WO | WO 02/058702 | 8/2002 |
| WO | WO 02/078641 | 10/2002 |
| WO | WO 02/078707 | 10/2002 |
| WO | WO 02/079155 | 10/2002 |
| WO | WO 02/079188 | 10/2002 |

OTHER PUBLICATIONS

Ames, R.S., et al., *Nature* (1999), 401, pp. 282-286.
Barlin G.B., et al., *Aust. J. Chem.* (1984), 37, pp. 1065-1073.
Bern H.A., et al., *Recent Prog. Horm. Res.* (1985), 41, pp. 533-552.
Breu V., et al., *FEBS Lett.* (1993), 334, pp. 210-214.
Douglas S.A., et al., *Br. J. Pharmacol.* (2000), 131, pp. 1262-1274.
Douglas S.A., et al., *J. Cardiovasc. Pharmacol.* (2000), 36, Suppl.1, pp. S163-S166.
Gartlon J., et al., *Psychopharmacology* (Berlin) (2001), 155, pp. 426-433.
Irving H., et al., *J. Chem. Soc.* (1959), p. 288.
Kaneko C., et al., *Chem. Pharm. Bull.* (1980), 28, pp. 1157-1171.
Laguzza B.C., et al., *Tetrahedron Lett.* (1981), 22, pp. 1483-1486.
Liu Q., et al., *Biochem. Biophys. Res. Commun.* (1999), 266, pp. 174-178.
Mori M., et al., *Biochem. Biophys. Res. Commun.* (1999), 265, pp. 123-129.
Radinov R., et al., *Synthesis* (19 86), pp. 886-891.
Russell F.D. et al., *Br. J. Pharmacol.* (2001), 132, pp. 5-9.
Silvestre R.A., et al., *Horm. Metab. Res.* (2001), 33, pp. 379-381.
Takahashi K., et al., *Peptides* (2001), 22, pp. 1175-1179.
Totsune K., et al., *Lancet* (2001), 358, pp. 810-811.
Tsandis A., et al., *J. Am. Coll. Cardiol.* (2001), 37, p. 164A.
Zou Y., et al., *FEBS Lett.* (2001), 508, pp. 57-60.

*Primary Examiner*—D. Margaret Seaman

(57) ABSTRACT

The invention relates to novel 1-pyridin-4-yl urea derivatives and related compounds and their use as active ingredients in the preparation of pharmaceutical compositions. The invention also concerns related aspects including processes for the preparation of the compounds, pharmaceutical compositions containing one or more of those compounds and especially their use as neurohormonal antagonists.

23 Claims, No Drawings

QUINOLINE DERIVATIVES

FIELD OF THE INVENTION

The present invention relates to novel 4-(piperidinyl- and pyrrolidinyl-alkyl-ureido)-quinoline derivatives of the general formula 1 and their use as active ingredients in the preparation of pharmaceutical compositions. The invention also concerns related aspects including processes for the preparation of the compounds, pharmaceutical compositions containing one or more compounds of the general formula 1 and especially their use as neurohormonal antagonists.

BACKGROUND OF THE INVENTION

Urotensin II is a cyclic 11-amino acid peptide neurohormone considered to be the most potent vasoconstrictor known, up to 28-fold more potent than endothelin-1. The effects of urotensin II are mediated through activation of a G-protein coupled receptor, the UT receptor, also known as GPR14 or SENR (Ames R S, et al, "Human urotensin-II is a potent vasoconstrictor and agonist for the orphan receptor GPR14" Nature (1999) 401, 282-6. Mori M, Sugo T, Abe M, Shimomura Y, Kurihara M, Kitada C, Kikuchi K, Shintani Y, Kurokawa T, Onda H, Nishimura O, Fujino M. "Urotensin II is the endogenous ligand of a G-protein-coupled orphan receptor, SENR (GPR14)" Biochem. Biophys. Res. Commun. (1999) 265, 123-9. Liu Q, Pong S S, Zeng Z, et al, "Identification of urotensin II as the endogenous ligand for the orphan G-protein-coupled receptor GPR14" Biochem. Biophys. Res. Commun. (1999) 266, 174-178.) Urotensin II and its receptor are conserved across evolutionarily distant species, suggesting an important physiological role for the system (Bern H A, Pearson D, Larson B A, Nishioka R S. "Neurohormones from fish tails: the caudal neurosecretory system. I. Urophysiology and the caudal neurosecretory system of fishes" Recent Prog. Horm. Res. (1985) 41, 533-552). In euryhaline fish, urotensin II has an osmoregulatory role, and in mammals urotensin II exerts potent and complex hemodynamic actions. The response to urotensin II is dependent on the anatomical source and species of the tissue being studied. (Douglas S A, Sulpizio A C, Piercy V, Sarau H M, Ames R S, Aiyar N V, Ohlstein E H, Willette R N. "Differential vasoconstrictor activity of human urotensin-II in vascular tissue isolated from the rat, mouse, dog, pig, marmoset and cynomolgus monkey" Br. J. Pharmacol. (2000) 131, 1262-1274. Douglas, S A, Ashton D J, Sauermelch C F, Coatney R W, Ohistein D H, Ruffolo M R, Ohistein E H, Aiyar N V, Willette R "Human urotensin-II is a potent vasoactive peptide: pharmacological characterization in the rat, mouse, dog and primate" J. Cardiovasc. Pharmacol. (2000) 36, Suppl 1:S163-6).

Like other neurohormones, urotensin II has growth stimulating and profibrotic actions in addition to its vasoactive properties. Urotensin II increases smooth muscle cell proliferation, and stimulates collagen synthesis (Tzandis A, et al, "Urotensin II stimulates collagen synthesis by cardiac fibroblasts and hypertrophic signaling in cardiomyocytes via G(alpha)q- and Ras-dependent pathways" J. Am. Coll. Cardiol. (2001) 37, 164A. Zou Y, Nagai R, and Yamazaki T, "Urotensin II induces hypertrophic responses in cultured cardiomyocytes from neonatal rats" FEBS Lett (2001) 508, 57-60). Urotensin II regulates hormone release (Silvestre R A, et al, "Inhibition of insulin release by urotensin II-a study on the perfused rat pancreas" Horm Metab Res (2001) 33, 379-81). Urotensin II has direct actions on atrial and ventricular myocytes (Russell F D, Molenaar P, and O'Brien D M "Cardiostimulant effects of urotensin-II in human heart in vitro" Br. J. Pharmacol. (2001) 132, 5-9). Urotensin II is produced by cancer cell lines and its receptor is also expressed in these cells. (Takahashi K, et al, "Expression of urotensin II and urotensin II receptor mRNAs in various human tumor cell lines and secretion of urotensin Il-like immunoreactivity by SW-13 adrenocortical carcinoma cells" Peptides (2001) 22, 1175-9). Urotensin II and its receptor are found in spinal cord and brain tissue, and intracerebroventricular infusion of urotensin II into mice induces behavioral changes (Gartlon J, et al, "Central effects of urotensin-II following ICV administration in rats" Psychopharmacology (Berlin) (2001) 155, 426-33).

Dysregulation of urotensin II is associated with human disease. Elevated circulating levels of urotensin II are detected in hypertensive patients, in heart failure patients, and in patients awaiting kidney transplantation (Totsune K, et al, "Role of urotensin II in patients on dialysis" Lancet (2001) 358, 810-1).

Substances with the ability to block the actions of urotensin II are expected to prove useful in the treatment of various diseases. WO-2001/45694, WO-2002/78641, WO-2002/78707, WO-2002/79155, and WO-2002/79188 disclose certain sulfonamides as urotensin II receptor antagonists, and their use to treat diseases associated with a urotensin II imbalance. WO-2001/45700 and WO-2001/45711 disclose certain pyrrolidines or piperidines as urotensin II receptor antagonists and their use to treat diseases associated with a urotensin II imbalance. These derivatives are different from the compounds of the present invention as they do not comprise urea derivatives bearing a 4-pyridinyl-like moiety. WO-2002/047687 discloses certain 2-amino-quinolones as urotensin 11 receptor antagonists and their use to treat diseases associated with a urotensin 11 imbalance. WO-2002/058702 discloses certain 2-amino-quinolines as urotensin II receptor antagonists and their use to treat diseases associated with a urotensin II imbalance. These derivatives are different from the compounds of the present invention as they do not bear a substituted urea function in the 4-position of the quinoline ring. WO-2001/66143 discloses certain 2,3-dihydro-1H-pyrrolo[2,3-b]quinolin-4-ylamine derivatives useful as urotensin II receptor antagonists, WO-2002/00606 discloses certain biphenyl compounds useful as urotensin II receptor antagonists, and WO-2002/02530 also discloses certain compounds useful as urotensin II receptor antagonists.

EP 428434 discloses certain alkylureidopyridines as neurokinin and substance P antagonists. WO-99/21835 discloses certain ureidoquinolines as H+-ATPase and bone resorption inhibitors. WO-01/009088 discloses certain substituted heteroarylureas as inhibitors of the CCR-3 receptor. All of these ureidopyridine derivatives differ in their composition from compounds of the present invention. The present invention comprises N-(cyclic amino alkyl)-N'-pyridin-4-yl urea derivatives which are novel compositions of matter and which are useful as urotensin II receptor antagonists.

DESCRIPTION OF THE INVENTION

The present invention relates to compounds of the general formula 1.

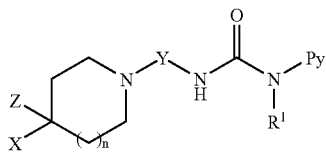

General Formula 1 wherein:

Py represents pyridin-4-yl mono-substituted in position 2 with —$NR^2R^3$; pyridin-4-yl disubstituted in position 2 with —$NR^2R^3$ and in position 6 with lower alkyl or arylalkyl; unsubstituted quinolin-4-yl; quinolin-4-yl mono-substituted in position 2 with lower alkyl; quinolin-4-yl di-substituted in position 2 with lower alkyl and in position 6, 7, or 8 with halogen, lower alkyl, or arylalkyl; 2-hydroxymethyl-quinolin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; 1-benzyl-2,3-dihydro-1H-pyrrolo[2,3-b]pyridin-4-yl;

X represents aryl; aryl-O—; arylalkyl-; lower alkyl-$SO_2NR^2$—; aryl-$SO_2NR^2$—; arylalkyl-$SO_2NR^2$—; lower alkyl-$CONR^2$—; aryl-$CONR^2$—; arylalkyl-$CONR^2$—; lower alkyl-$NR^3CONR^2$—; aryl-$NR^3CONR^2$—; arylalkyl-$NR^3CONR^2$—; aryl-CO—; arylalkyl-CO—; lower alkyl-$NR^2CO$—;aryl-$NR^2CO$—; arylalkyl-$NR^2CO$—; or X and Z represent together with the carbon atom to which they are attached an exocyclic double bond which bears an aryl substituent.

Y represents —$C(R^4)(R^5)(CH_2)_m$— or —$(CH_2)_mC(R^4)(R^5)$—

Z represents hydrogen; in case X represents aryl or arylalkyl, Z represents hydrogen, hydroxyl, carboxyl, aryl-$CONR^2$—, lower alkyl-$NR^2CO$—, aryl-$NR^2CO$— or arylalkyl-$NR^2CO$—;

n represents the numbers 0 or 1;

m represents the numbers 1 or 2;

$R^1$ represents hydrogen or lower alkyl;

$R^2$ and $R^3$ represent independently hydrogen, lower alkyl, or arylalkyl; in case $R^2$ and $R^3$ are attached to the same nitrogen atom, $R^2$ and $R^3$ together form with the nitrogen to which they are attached, a piperidine, pyrrolidine or morpholine ring;

$R^4$ represents hydrogen, lower alkyl, aryl, arylalkyl, or forms together with $R^5$ a 3-, 4-, 5-, or 6-membered saturated carbocyclic ring including the carbon atom to which $R^4$ and $R^5$ are attached as ring atoms;

$R^5$ represents hydrogen, methyl, or forms together with $R^4$ a 3-, 4-, 5-, or 6-membered saturated carbocyclic ring including the carbon atom to which $R^4$ and $R^5$ are attached as ring atoms;

and optically pure enantiomers or diastereomers, mixtures of enantiomers or diastereomers, diastereomeric racemates, and mixtures of diastereomeric racemates; as well as their pharmaceutically acceptable salts, solvent complexes, and morphological forms.

In the definitions of the general formula 1 the expression 'aryl' means a substituted or unsubstituted aromatic carbocyclic or heterocyclic ring system, consisting of a five- or six-membered aromatic ring, or of a fused five-six or six-six aromatic ring system. Preferred aryl groups are for example 2-furyl; 2-thienyl; phenyl; 2-methylphenyl; 2-biphenyl; 2-methoxyphenyl; 2-phenoxyphenyl; 2-chlorophenyl; 2-bromophenyl; 2-i-propylphenyl; 2-fluorophenyl; 2-methylsulfonylphenyl; 2-cyanophenyl; 2-trifluoromethylphenyl; 3-methylphenyl; 3-biphenyl; 3-phenoxyphenyl; 3-methoxyphenyl; 3-chlorophenyl; 3-bromophenyl; 3-fluorophenyl; 3-cyanophenyl; 3-trifluoromethylphenyl; 3-carboxyphenyl; 4-methylphenyl; 4-ethylphenyl; 4-i-propylphenyl; 4-phenyloxyphenyl; 4-trifluoromethylphenyl; 4-trifluoromethoxyphenyl; 4-phenoxyphenyl; 4-cyanophenyl; 4-hydroxyphenyl; 4-acetylaminophenyl; 4-methanesulfonylphenyl; 4-n-propylphenyl; 4-iso-propylphenyl; 4-tert-butylphenyl; 4-n-pentylphenyl; 4-biphenyl; 4-chlorophenyl; 4-bromophenyl; 4-bromo-2-ethylphenyl; 4-fluorophenyl; 2,4-difluorophenyl; 4-n-butoxyphenyl; 2,6-dimethoxyphenyl; 3,5-bis-trifluoromethylphenyl; 2-pyridyl; 3-pyridyl; 4-pyridyl; 1-naphthyl; 2-naphthyl; 4-(pyrrol-1-yl)phenyl; 4-benzoylphenyl; 5-dimethylaminonaphth-1-yl; 5-chloro-3-methylthiophen-2-yl; 5-chloro-3-methyl-benzo[b]thiophen-2-yl; 3-(phenylsulfonyl)-thiophen-2-yl; 2-(2,2,2-trifluoroacetyl)-1-2,3,4-tetrahydroisoquinolin-7-yl; 4-(3-chloro-2-cyanophenyloxy) phenyl; 2-(5-benzamidomethyl)thiophenyl; 4,5-dichlorothien-2-yl; 5-quinolyl-; 6-quinolyl; 7-quinolyl; 8-quinolyl; (2-acetylamino-4-methyl)thiazol-5-yl; or 1-methyl imidazol-4-yl.

In the definitions of the general formula 1 the expression 'lower alkyl' means a saturated straight chain, branched chain or cyclic substituent consisting of from one to eight carbons, comprising methyl, ethyl, n-propyl, 3-allyl, iso-propyl, n-butyl, iso-butyl, n-pentyl, n-hexyl, n-octyl, cyclopropyl, cyclopentyl, cyclohexyl, cyclopropylmethyl and the like. Preferred lower alkyl groups are methyl, ethyl, and n-propyl.

In the definitions of the general formula 1 the expression 'arylalkyl' means a C1 to C3 group bearing an aryl group, where 'aryl' has the meaning given above.

The present invention encompasses pharmaceutically acceptable salts of compounds of the general formula 1. This encompasses either salts with inorganic acids or organic acids like hydrohalogenic acids, e.g. hydrochloric or hydrobromic acid, sulfuric acid, phosphoric acid, nitric acid, citric acid, formic acid, acetic acid, maleic acid, tartaric acid, methylsulfonic acid, p-tolylsulfonic acid and the like or in case the compound of formula 1 is acidic in nature with an inorganic base like an alkali or earth alkali base, e.g. sodium, potassium, or calcium salts, etc. The compounds of general formula 1 can also be present in form of zwitterions.

The present invention encompasses different solvation complexes of compounds of general formula 1. The salvation can be effected in the course of the manufacturing process or can take place separately, e.g. as a consequence of hygroscopic properties of an initially anhydrous compound of general formula 1.

The present invention further encompasses different morphological forms, e.g. crystalline forms, of compounds of general formula 1 and their salts and salvation complexes. Particular heteromorphs may exhibit different dissolution properties, stability profiles, and the like, and are all included in the scope of the present invention.

The compounds of the general formula 1 might have one or more asymmetric carbon atoms and may be prepared in form of optically pure enantiomers or diastereomers, mixtures of enantiomers or diastereomers, diastereomeric racemates, and mixtures of diastereomeric racemates. The present invention encompasses all these forms. They are prepared by stereoselective synthesis, or by separation of mixtures in a manner known per se, i.e. by column chromatography, thin layer chromatography, HPLC, crystallization, etc.

Preferred compounds of the invention are compounds of the general formula 2.

General Formula 2

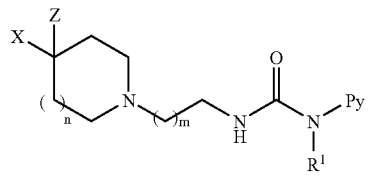

wherein:

Py represents 2-(benzyl-methyl-amino)-pyridin-4-yl; 2-(benzyl-methyl-amino)-6-methyl-pyridin-4-yl; 2-(benzylamino)-pyridin-4-yl; 2-benzylamino-6-methyl-pyridin-4-yl; 2-(dimethylamino)-pyridin-4-yl; 2-(dimethylamino)-6-methyl-pyridin-4-yl; 2-(methylamino)-pyridin-4-yl; 2-(methylamino)-methyl-pyridin-4-yl; 2-aminopyridin-4-yl; 2-amino-6-methyl-pyridin-4-yl; 2-(pyrrolidin-1-yl)-pyridin-4-yl; quinol-4-yl; 2-methylquinol-4-yl; 2-cyclopropylquinol-4-yl; 8-benzyl-2-methyl-quinol-4-yl; [1,8]naphthyridin-4-yl; 7-methyl-[1,8]naphthyridin-4-yl; 5,6,7,8-tetrahydro-[1,8]naphthyridin-4-yl; 8-benzyl-5,6,7,8-tetrahydro-[1, 8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; 1-benzyl-2,3-dihydro-1H-pyrrolo[2,3-b]pyridin-4-yl;

X represents aryl; aryl-O—; arylalkyl-; lower alkyl-SO$_2$NR$^2$—; aryl-SO$_2$NR$^2$—; arylalkyl-SO$_2$NR$^2$—; lower alkyl-CONR$^2$—; aryl-CONR$^2$—; arylalkyl-CONR$^2$—; lower alkyl-NR$^3$CONR$^2$—; aryl-NR$^3$CONR$^2$—; arylalkyl-NR$^3$CONR$^2$—; aryl-CO—; arylalkyl-CO—; lower alkyl-NR$^2$CO—;aryl-N R$^2$CO—; arylalkyl-NR$^2$CO—;

Z represents hydrogen; in case X represents aryl or arylalkyl, Z represents hydrogen or hydroxyl;

n represents the numbers 0 or 1;

m represents the numbers 1 or 2;

R$^1$ represents hydrogen or lower alkyl;

R$^2$ and R$^3$ represent independently hydrogen, lower alkyl, or arylalkyl;

Preferred compounds of general formula 1 are the compounds of general formula 3:

General formula 3

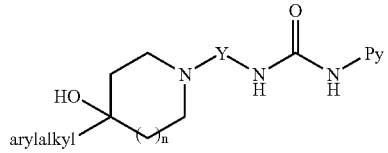

wherein n, Y and Py have the meaning given in general formula 1.

Preferred compounds of general formula 1 are the compounds of general formula 4:

General formula 4

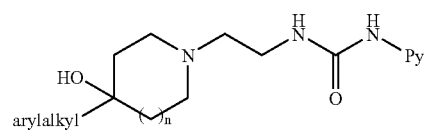

wherein n and Py has the meaning given in general formula 2.

Preferred compounds of general formula 1 are the compounds of general formula 5:

General formula 5

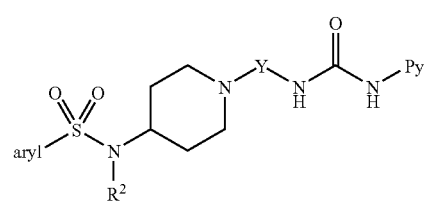

wherein R$^2$, Y and Py have the meaning given in general formula 1.

Preferred compounds of general formula 1 are the compounds of general formula 6:

General formula 6

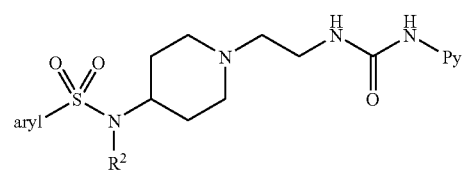

wherein R$^2$ and Py have the meaning given in general formula 2.

Preferred compounds of general formula 1 are the compounds of general formula 7:

General formula 7

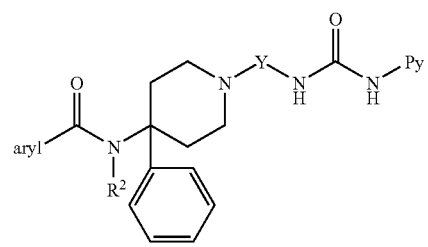

wherein R$^2$, Y and Py have the meaning given in general formula 1.

Preferred compounds of general formula 1 are the compounds of general formula 8:

General formula 8

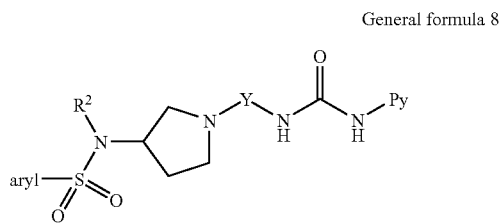

wherein R², Y and Py have the meaning given in general formula 1.

Preferred compounds of general formula 1 are the compounds of general formula 9:

General formula 9

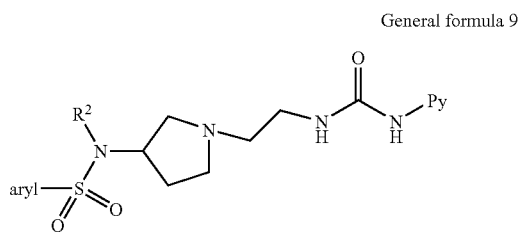

wherein R² and Py have the meaning given in general formula 2.

Preferred compounds of general formula 1 are the compounds of general formula 10:

General formula 10

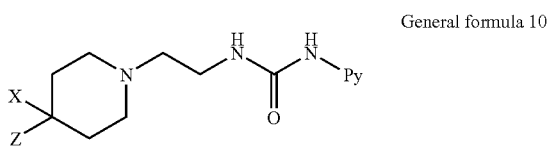

wherein X, Z and Py have the meaning given in general formula 1.

Preferred compounds of general formula 1 are the compounds of general formula 11:

General formula 11

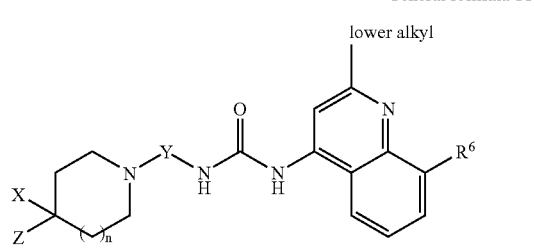

wherein $R^6$ is hydrogen, lower alkyl, or arylalkyl; and n, X, Y, and Z have the meaning given in general formula 1.

Preferred compounds of general formula 1 are the compounds of general formula 12:

General formula 12

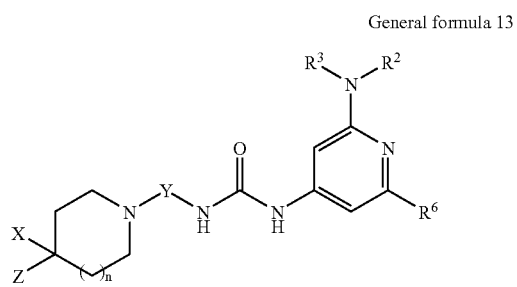

wherein $R^6$ has the meaning given in general formula 11; and n, X and Z have the meaning given in general formula 2.

Preferred compounds of general formula 1 are the compounds of general formula 13:

General formula 13

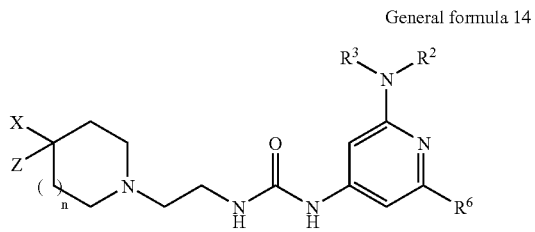

wherein $R^6$ has the meaning given in general formula 11; and n, $R^2$, $R^3$, X, Y, and Z have the meaning given in general formula 1.

Preferred compounds of general formula 1 are the compounds of general formula 14:

General formula 14

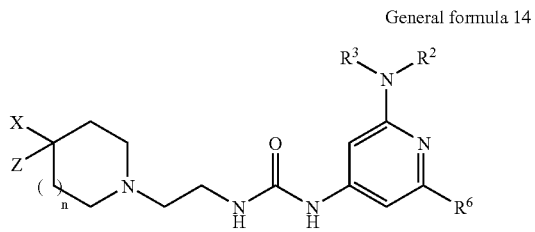

wherein $R^6$ has the meaning given in general formula 11; and n, $R^2$, $R^3$, X and Z have the meaning given in general formula 1.

Preferred compounds of general formula 1 are the compounds of general formula 15:

General formula 15

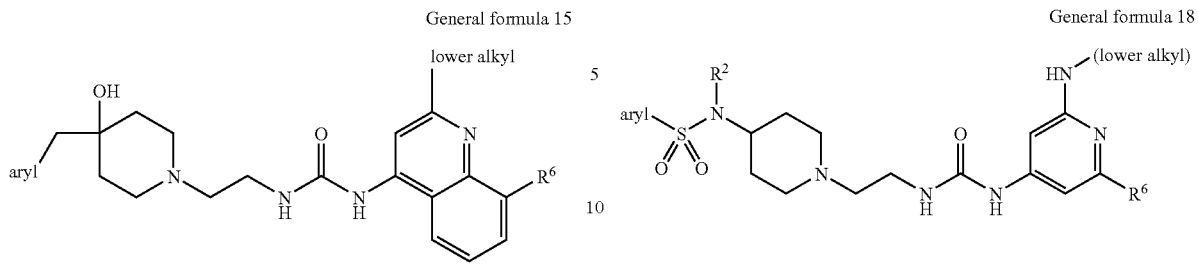

wherein R⁶ has the meaning given in general formula 11.

Preferred compounds of general formula 1 are the compounds of general formula 16:

General formula 16

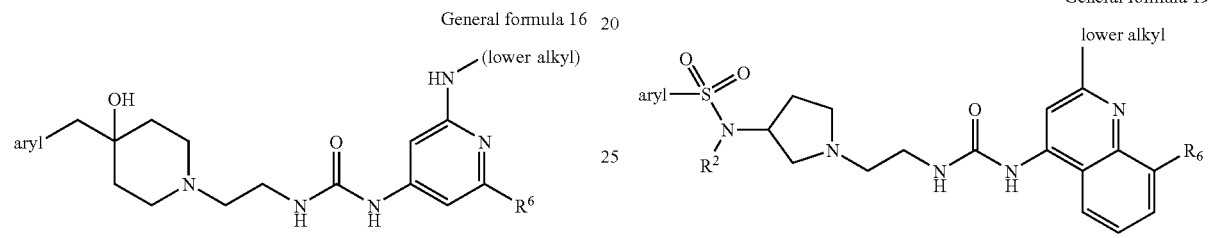

wherein R⁶ has the meaning given in general formula 11.

Preferred compounds of general formula 1 are the compounds of general formula 17:

General formula 17

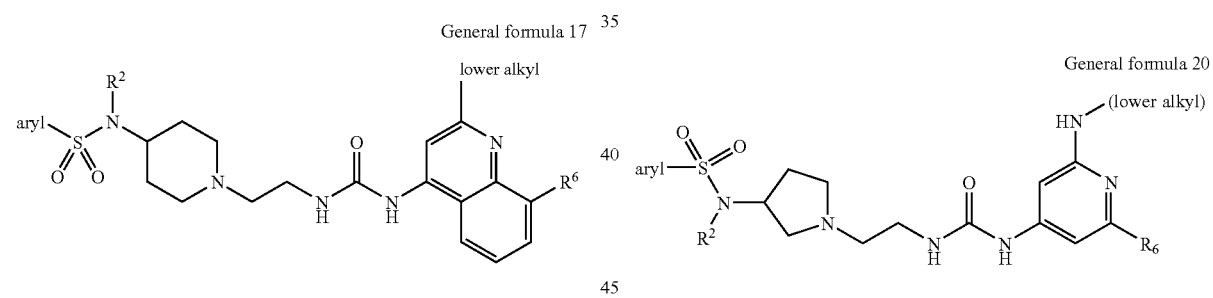

wherein R⁶ has the meaning given in general formula 11; and R² has the meaning given in general formula 1.

Preferred compounds of general formula 1 are the compounds of general formula 18:

General formula 18

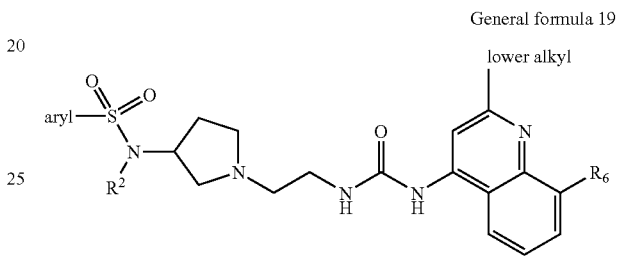

wherein R⁶ has the meaning given in general formula 11; and R² has the meaning given in general formula 1.

Preferred compounds of general formula 1 are the compounds of general formula 19:

General formula 19 wherein R⁶ has the meaning given in general formula 11; and R² has the meaning given in general formula 1.

Preferred compounds of general formula 1 are the compounds of general formula 20:

General formula 20

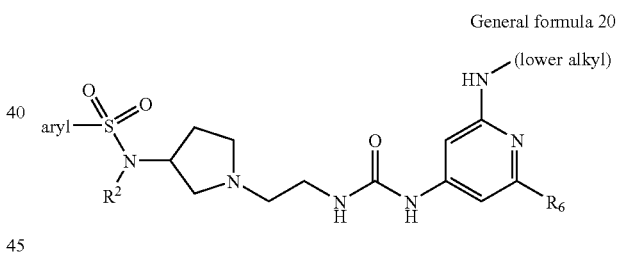

wherein R⁶ has the meaning given in general formula 11; and R² has the meaning given in general formula 1.

Examples of particularly preferred compounds of general formula 1 are selected from the group consisting of:

| Example Number | |
|---|---|
| 1. | N-(1-{2-[3-(2-Methyl-quinolin-4-yl)-ureido]-ethyl}-piperidin-4-yl)-4-trifluoromethyl-benzenesulfonamide |
| 3. | N-Methyl-N-(1-{2-[3-(2-methyl-quinolin-4-yl)-ureido]-ethyl}-pyrrolidin-3-yl)-benzenesulfonamide |
| 5. | Thiophene-2-sulfonic acid (1-{2-[3-(2-methyl-quinolin-4-yl)-ureido]-ethyl}-pyrrolidin-3-yl)-amide |
| 8. | 3-Methyl-N-(1-{2-[3-(2-methyl-quinolin-4-yl)-ureido]-ethyl}-pyrrolidin-3-yl)-benzenesulfonamide |
| 9. | 3,N-Dimethyl-N-(1-{2-[3-(2-methyl-quinolin-4-yl)-ureido]-ethyl}-pyrrolidin-3-yl)-benzenesulfonamide |
| 11. | 2-Methyl-N-(1-{2-[3-(2-methyl-quinolin-4-yl)-ureido]-ethyl}-pyrrolidin-3-yl)-benzenesulfonamide |

-continued

| Example Number | |
|---|---|
| 12. | 2,N-Dimethyl-N-(1-{2-[3-(2-methyl-quinolin-4-yl)-ureido]-ethyl}-pyrrolidin-3-yl)-benzenesulfonamide |
| 13. | 4-Methyl-N-(1-{2-[3-(2-methyl-quinolin-4-yl)-ureido]-ethyl}-piperidin-4-yl)-benzenesulfonamide |
| 14. | 4-Methyl-N-(1-{2-[3-(2-methyl-quinolin-4-yl)-ureido]-ethyl}-pyrrolidin-3-yl)-benzenesulfonamide |
| 15. | 4,N-Dimethyl-N-(1-{2-[3-(2-methyl-quinolin-4-yl)-ureido]-ethyl}-pyrrolidin-3-yl)-benzenesulfonamide |
| 17. | 2-Fluoro-N-(1-{2-[3-(2-methyl-quinolin-4-yl)-ureido]-ethyl}-pyrrolidin-3-yl)-benzenesulfonamide |
| 18. | 2-Fluoro-N-methyl-N-(1-{2-[3-(2-methyl-quinolin-4-yl)-ureido]-ethyl}-pyrrolidin-3-yl)-benzenesulfonamide |
| 21. | 3-Fluoro-N-methyl-N-(1-{2-[3-(2-methyl-quinolin-4-yl)-ureido]-ethyl}-pyrrolidin-3-yl)-benzenesulfonamide |
| 24. | 4-Fluoro-N-methyl-N-(1-{2-[3-(2-methyl-quinolin-4-yl)-ureido]-ethyl}-pyrrolidin-3-yl)-benzenesulfonamide |
| 31. | 4-Cyano-N-(1-{2-[3-(2-methyl-quinolin-4-yl)-ureido]-ethyl}-piperidin-4-yl)-benzenesulfonamide |
| 35. | 3-Methoxy-N-(1-{2-[3-(2-methyl-quinolin-4-yl)-ureido]-ethyl}-pyrrolidin-3-yl)-benzenesulfonamide |
| 36. | 3-Methoxy-N-methyl-N-(1-{2-[3-(2-methyl-quinolin-4-yl)-ureido]-ethyl}-pyrrolidin-3-yl)-benzenesulfonamide |
| 37. | 4-Methoxy-N-(1-{2-[3-(2-methyl-quinolin-4-yl)-ureido]-ethyl}-piperidin-4-yl)-benzenesulfonamide |
| 38. | 4-Methoxy-N-(1-{2-[3-(2-methyl-quinolin-4-yl)-ureido]-ethyl}-pyrrolidin-3-yl)-benzenesulfonamide |
| 39. | 4-Methoxy-N-methyl-N-(1-{2-[3-(2-methyl-quinolin-4-yl)-ureido]-ethyl}-pyrrolidin-3-yl)-benzenesulfonamide |
| 41. | 3-Chloro-N-(1-{2-[3-(2-methyl-quinolin-4-yl)-ureido]-ethyl}-pyrrolidin-3-yl)-benzenesulfonamide |
| 42. | 3-Chloro-N-methyl-N-(1-{2-[3-(2-methyl-quinolin-4-yl)-ureido]-ethyl}-pyrrolidin-3-yl)-benzenesulfonamide |
| 43. | 4-Chloro-N-(1-{2-[3-(2-methyl-quinolin-4-yl)-ureido]-ethyl}-piperidin-4-yl)-benzenesulfonamide |
| 44. | 4-Chloro-N-(1-{2-[3-(2-methyl-quinolin-4-yl)-ureido]-ethyl}-pyrrolidin-3-yl)-benzenesulfonamide |
| 46. | 2-Chloro-N-(1-{2-[3-(2-methyl-quinolin-4-yl)-ureido]-ethyl}-pyrrolidin-3-yl)-benzenesulfonamide |
| 55. | Biphenyl-4-sulfonic acid methyl-(1-{2-[3-(2-methyl-quinolin-4-yl)-ureido]-ethyl}-pyrrolidin-3-yl)-amide |
| 57. | N-(1-{2-[3-(2-Methyl-quinolin-4-yl)-ureido]-ethyl}-pyrrolidin-3-yl)-4-propyl-benzenesulfonamide |
| 58. | N-Methyl-N-(1-{2-[3-(2-methyl-quinolin-4-yl)-ureido]-ethyl}-pyrrolidin-3-yl)-4-propyl-benzenesulfonamide |
| 62. | Naphthalene-2-sulfonic acid (1-{2-[3-(2-methyl-quinolin-4-yl)-ureido]-ethyl}-piperidin-4-yl)-amide |
| 63. | Naphthalene-2-sulfonic acid (1-{2-[3-(2-methyl-quinolin-4-yl)-ureido]-ethyl}-pyrrolidin-3-yl)-amide |
| 64. | Naphthalene-2-sulfonic acid methyl-(1-{2-[3-(2-methyl-quinolin-4-yl)-ureido]-ethyl}-pyrrolidin-3-yl)-amide |
| 65. | Naphthalene-1-sulfonic acid (1-{2-[3-(2-methyl-quinolin-4-yl)-ureido]-ethyl}-piperidin-4-yl)-amide |
| 66. | Naphthalene-1-sulfonic acid (1-{2-[3-(2-methyl-quinolin-4-yl)-ureido]-ethyl}-pyrrolidin-3-yl)-amide |
| 67. | Naphthalene-1-sulfonic acid methyl-(1-{2-[3-(2-methyl-quinolin-4-yl)-ureido]-ethyl}-pyrrolidin-3-yl)-amide |
| 69. | Quinoline-8-sulfonic acid (1-{2-[3-(2-methyl-quinolin-4-yl)-ureido]-ethyl}-pyrrolidin-3-yl)-amide |
| 70. | Quinoline-8-sulfonic acid methyl-(1-{2-[3-(2-methyl-quinolin-4-yl)-ureido]-ethyl}-pyrrolidin-3-yl)-amide |
| 72. | 4-tert-Butyl-N-(1-{2-[3-(2-methyl-quinolin-4-yl)-ureido]-ethyl}-pyrrolidin-3-yl)-benzenesulfonamide |
| 73. | 4-tert-Butyl-N-methyl-N-(1-{2-[3-(2-methyl-quinolin-4-yl)-ureido]-ethyl}-pyrrolidin-3-yl)-benzenesulfonamide |
| 77. | N-(1-{2-[3-(2-Methyl-quinolin-4-yl)-ureido]-ethyl}-pyrrolidin-3-yl)-4-trifluoromethyl-benzenesulfonamide |
| 78. | N-Methyl-N-(1-{2-[3-(2-methyl-quinolin-4-yl)-ureido]-ethyl}-pyrrolidin-3-yl)-4-trifluoromethyl-benzenesulfonamide |
| 79. | N-(1-{2-[3-(2-Methyl-quinolin-4-yl)-ureido]-ethyl}-piperidin-4-yl)-2-trifluoromethyl-benzenesulfonamide |
| 80. | N-(1-{2-[3-(2-Methyl-quinolin-4-yl)-ureido]-ethyl}-pyrrolidin-3-yl)-2-trifluoromethyl-benzenesulfonamide |
| 81. | N-Methyl-N-(1-{2-[3-(2-methyl-quinolin-4-yl)-ureido]-ethyl}-pyrrolidin-3-yl)-2-trifluoromethyl-benzenesulfonamide |
| 83. | N-(1-{2-[3-(2-Methyl-quinolin-4-yl)-ureido]-ethyl}-pyrrolidin-3-yl)-3-trifluoromethyl-benzenesulfonamide |

-continued

| Example Number | |
|---|---|
| 85. | 3,4-Dichloro-N-(1-{2-[3-(2-methyl-quinolin-4-yl)-ureido]-ethyl}-piperidin-4-yl)-benzenesulfonamide |
| 87. | 3,4-Dichloro-N-methyl-N-(1-{2-[3-(2-methyl-quinolin-4-yl)-ureido]-ethyl}-pyrrolidin-3-yl)-benzenesulfonamide |
| 88. | N-(1-{2-[3-(2-Methyl-quinolin-4-yl)-ureido]-ethyl}-piperidin-4-yl)-4-pentyl-benzenesulfonamide |
| 89. | N-(1-{2-[3-(2-Methyl-quinolin-4-yl)-ureido]-ethyl}-pyrrolidin-3-yl)-4-pentyl-benzenesulfonamide |
| 90. | N-Methyl-N-(1-{2-[3-(2-methyl-quinolin-4-yl)-ureido]-ethyl}-pyrrolidin-3-yl)-4-pentyl-benzenesulfonamide |
| 92. | 4-Butoxy-N-(1-{2-[3-(2-methyl-quinolin-4-yl)-ureido]-ethyl}-pyrrolidin-3-yl)-benzenesulfonamide |
| 93. | 4-Butoxy-N-methyl-N-(1-{2-[3-(2-methyl-quinolin-4-yl)-ureido]-ethyl}-pyrrolidin-3-yl)-benzenesulfonamide |
| 94. | 4,5-Dichloro-thiophene-2-sulfonic acid (1-{2-[3-(2-methyl-quinolin-4-yl)-ureido]-ethyl}-piperidin-4-yl)-amide |
| 95. | 4,5-Dichloro-thiophene-2-sulfonic acid (1-{2-[3-(2-methyl-quinolin-4-yl)-ureido]-ethyl}-pyrrolidin-3-yl)-amide |
| 96. | 4,5-Dichloro-thiophene-2-sulfonic acid methyl-(1-{2-[3-(2-methyl-quinolin-4-yl)-ureido]-ethyl}-pyrrolidin-3-yl)-amide |
| 97. | 4-(3-Chloro-2-cyano-phenoxy)-N-(1-{2-[3-(2-methyl-quinolin-4-yl)-ureido]-ethyl}-piperidin-4-yl)-benzenesulfonamide |
| 98. | 4-(3-Chloro-2-cyano-phenoxy)-N-(1-{2-[3-(2-methyl-quinolin-4-yl)-ureido]-ethyl}-pyrrolidin-3-yl)-benzenesulfonamide |
| 99. | 4-(3-Chloro-2-cyano-phenoxy)-N-methyl-N-(1-{2-[3-(2-methyl-quinolin-4-yl)-ureido]-ethyl}-pyrrolidin-3-yl)-benzenesulfonamide |
| 103. | N-[4-Methyl-5-(1-{2-[3-(2-methyl-quinolin-4-yl)-ureido]-ethyl}-piperidin-4-ylsulfamoyl)-thiazol-2-yl]-acetamide |
| 106. | 3-Bromo-N-(1-{2-[3-(2-methyl-quinolin-4-yl)-ureido]-ethyl}-piperidin-4-yl)-benzenesulfonamide |
| 107. | 3-Bromo-N-(1-{2-[3-(2-methyl-quinolin-4-yl)-ureido]-ethyl}-pyrrolidin-3-yl)-benzenesulfonamide |
| 108. | 3-Bromo-N-methyl-N-(1-{2-[3-(2-methyl-quinolin-4-yl)-ureido]-ethyl}-pyrrolidin-3-yl)-benzenesulfonamide |
| 109. | 4-Bromo-N-(1-{2-[3-(2-methyl-quinolin-4-yl)-ureido]-ethyl}-piperidin-4-yl)-benzenesulfonamide |
| 110. | 4-Bromo-N-(1-{2-[3-(2-methyl-quinolin-4-yl)-ureido]-ethyl}-pyrrolidin-3-yl)-benzenesulfonamide |
| 111. | 4-Bromo-N-methyl-N-(1-{2-[3-(2-methyl-quinolin-4-yl)-ureido]-ethyl}-pyrrolidin-3-yl)-benzenesulfonamide |
| 113. | N-(1-{2-[3-(2-Methyl-quinolin-4-yl)-ureido]-ethyl}-pyrrolidin-3-yl)-2-trifluoromethoxy-benzenesulfonamide |
| 115. | N-(1-{2-[3-(2-Methyl-quinolin-4-yl)-ureido]-ethyl}-piperidin-4-yl)-4-trifluoromethoxy-benzenesulfonamide |
| 116. | N-(1-{2-[3-(2-Methyl-quinolin-4-yl)-ureido]-ethyl}-pyrrolidin-3-yl)-4-trifluoromethoxy-benzenesulfonamide |
| 117. | N-Methyl-N-(1-{2-[3-(2-methyl-quinolin-4-yl)-ureido]-ethyl}-pyrrolidin-3-yl)-4-trifluoromethoxy-benzenesulfonamide |
| 118. | 5-Dimethylamino-naphthalene-1-sulfonic acid (1-{2-[3-(2-methyl-quinolin-4-yl)-ureido]-ethyl}-piperidin-4-yl)-amide |
| 119. | 5-Dimethylamino-naphthalene-1-sulfonic acid (1-{2-[3-(2-methyl-quinolin-4-yl)-ureido]-ethyl}-pyrrolidin-3-yl)-amide |
| 120. | 5-Dimethylamino-naphthalene-1-sulfonic acid methyl-(1-{2-[3-(2-methyl-quinolin-4-yl)-ureido]-ethyl}-pyrrolidin-3-yl)-amide |
| 121. | 5-Chloro-3-methyl-benzo[b]thiophene-2-sulfonic acid (1-{2-[3-(2-methyl-quinolin-4-yl)-ureido]-ethyl}-piperidin-4-yl)-amide |
| 122. | 5-Chloro-3-methyl-benzo[b]thiophene-2-sulfonic acid (1-{2-[3-(2-methyl-quinolin-4-yl)-ureido]-ethyl}-pyrrolidin-3-yl)-amide |
| 123. | 5-Chloro-3-methyl-benzo[b]thiophene-2-sulfonic acid methyl-(1-{2-[3-(2-methyl-quinolin-4-yl)-ureido]-ethyl}-pyrrolidin-3-yl)-amide |
| 124. | 4-Bromo-2-ethyl-N-(1-{2-[3-(2-methyl-quinolin-4-yl)-ureido]-ethyl}-piperidin-4-yl)-benzenesulfonamide |
| 125. | 4-Bromo-2-ethyl-N-(1-{2-[3-(2-methyl-quinolin-4-yl)-ureido]-ethyl}-pyrrolidin-3-yl)-benzenesulfonamide |
| 126. | 4-Bromo-2-ethyl-N-methyl-N-(1-{2-[3-(2-methyl-quinolin-4-yl)-ureido]-ethyl}-pyrrolidin-3-yl)-benzenesulfonamide |
| 130. | N-[5-(1-{2-[3-(2-Methyl-quinolin-4-yl)-ureido]-ethyl}-piperidin-4-ylsulfamoyl)-thiophen-2-ylmethyl]-benzamide |
| 131. | N-[5-(1-{2-[3-(2-Methyl-quinolin-4-yl)-ureido]-ethyl}-pyrrolidin-3-ylsulfamoyl)-thiophen-2-ylmethyl]-benzamide |
| 132. | N-{5-[Methyl-(1-{2-[3-(2-methyl-quinolin-4-yl)-ureido]-ethyl}-pyrrolidin-3-yl)-sulfamoyl]-thiophen-2-ylmethyl}-benzamide |
| 133. | 4-Benzenesulfonyl-thiophene-2-sulfonic acid (1-{2-[3-(2-methyl-quinolin-4-yl)-ureido]-ethyl}-piperidin-4-yl)-amide |
| 134. | 4-Benzenesulfonyl-thiophene-2-sulfonic acid (1-{2-[3-(2-methyl-quinolin-4-yl)-ureido]-ethyl}-pyrrolidin-3-yl)-amide |

-continued

| Example Number | |
|---|---|
| 135. | 4-Benzenesulfonyl-thiophene-2-sulfonic acid methyl-(1-{2-[3-(2-methyl-quinolin-4-yl)-ureido]-ethyl}-pyrrolidin-3-yl)-amide |
| 136. | 2-(2,2,2-Trifluoro-acetyl)-1,2,3,4-tetrahydro-isoquinoline-7-sulfonic acid (1-{2-[3-(2-methyl-quinolin-4-yl)-ureido]-ethyl}-piperidin-4-yl)-amide |
| 137. | 2-(2,2,2-Trifluoro-acetyl)-1,2,3,4-tetrahydro-isoquinoline-7-sulfonic acid (1-{2-[3-(2-methyl-quinolin-4-yl)-ureido]-ethyl}-pyrrolidin-3-yl)-amide |
| 138. | 2-(2,2,2-Trifluoro-acetyl)-1,2,3,4-tetrahydro-isoquinoline-7-sulfonic acid methyl-(1-{2-[3-(2-methyl-quinolin-4-yl)-ureido]-ethyl}-pyrrolidin-3-yl)-amide |
| 141. | 2-Phenyl-ethanesulfonic acid (1-{2-[3-(2-methyl-quinolin-4-yl)-ureido]-ethyl}-piperidin-4-yl)-amide |
| 142. | 4-Chloro-N-methyl-N-(1-{2-[3-(2-methyl-quinolin-4-yl)-ureido]-ethyl}-pyrrolidin-3-yl)-benzenesulfonamide |
| 144. | 4-Bromo-N-methyl-N-(1-{2-[3-(2-methyl-quinolin-4-yl)-ureido]-ethyl}-piperidin-4-yl)-benzenesulfonamide |
| 174. | 1-{2-[4-(3-Biphenyl-2-yl-ureido)-piperidin-1-yl]-ethyl}-3-(2-methyl-quinolin-4-yl)-urea |
| 175. | 1-{2-[3-(3-Biphenyl-2-yl-ureido)-pyrrolidin-1-yl]-ethyl}-3-(2-methyl-quinolin-4-yl)-urea |
| 239. | 1-(2-{4-[3-(2-Isopropyl-phenyl)-ureido]-piperidin-1-yl}-ethyl)-3-(2-methyl-quinolin-4-yl)-urea |
| 240. | 1-(2-{3-[3-(2-Isopropyl-phenyl)-ureido]-pyrrolidin-1-yl}-ethyl)-3-(2-methyl-quinolin-4-yl)-urea |
| 249. | 1-(2-Methyl-quinolin-4-yl)-3-(2-{3-[3-(2-phenoxy-phenyl)-ureido]-pyrrolidin-1-yl}-ethyl)-urea |
| 275. | N-(1-{2-[3-(2-Methyl-quinolin-4-yl)-ureido]-ethyl}-piperidin-4-yl)-2-naphthalen-1-yl-acetamide |
| 341. | 2-(4-Bromo-phenyl)-N-(1-{2-[3-(2-methyl-quinolin-4-yl)-ureido]-ethyl}-piperidin-4-yl)-acetamide |
| 346. | 4-Benzoyl-N-methyl-N-(1-{2-[3-(2-methyl-quinolin-4-yl)-ureido]-ethyl}-pyrrolidin-3-yl)-benzamide |
| 365. | 1-(2-Methyl-quinolin-4-yl)-3-[2-(4-phenyl-piperidin-1-yl)-ethyl]-urea |
| 367. | 1-(2-Methyl-quinolin-4-yl)-3-[2-(4-o-tolyl-piperidin-1-yl)-ethyl]-urea |
| 369. | 1-[2-(4-Benzyl-4-hydroxy-piperidin-1-yl)-ethyl]-3-(2-methyl-quinolin-4-yl)-urea |
| 370. | 1-[2-(4-Hydroxy-4-phenyl-piperidin-1-yl)-ethyl]-3-(2-methyl-quinolin-4-yl)-urea |
| 376. | 1-[2-(4-Benzyl-piperidin-1-yl)-ethyl]-3-(2-methyl-quinolin-4-yl)-urea |
| 437. | 1-[2-(Benzyl-methyl-amino)-pyridin-4-yl]-3-[2-(4-benzyl-piperidin-1-yl)-ethyl]-urea |

Examples of preferred compounds of general formula 1 are selected from the list consisting of:

| Example Number | |
|---|---|
| 143. | 4-Bromo-N-ethyl-N-(1-{2-[3-(2-methyl-quinolin-4-yl)-ureido]-ethyl}-piperidin-4-yl)-benzenesulfonamide |
| 145. | 4-Bromo-N-ethyl-N-(1-(2-[3-(2-methyl-quinolin-4-yl)-ureido]-ethyl}-pyrrolidin-3-yl)-benzenesulfonamide |
| 146. | 4-Bromo-N-(1-{2-[3-(2-methyl-quinolin-4-yl)-ureido]-ethyl}-piperidin-4-yl)-N-propyl-benzenesulfonamide |
| 147. | 4-Bromo-N-(1-{2-[3-(2-methyl-quinolin-4-yl)-ureido]-ethyl}-pyrrolidin-3-yl)-N-propyl-benzenesulfonamide |
| 148. | 4-Bromo-N-isobutyl-N-(1-{2-[3-(2-methyl-quinolin-4-yl)-ureido]-ethyl}-piperidin-4-yl)-benzenesulfonamide |
| 149. | 4-Bromo-N-isobutyl-N-(1-{2-[3-(2-methyl-quinolin-4-yl)-ureido]-ethyl}-pyrrolidin-3-yl)-benzenesulfonamide |
| 150. | 4-Bromo-N-butyl-N-(1-{2-[3-(2-methyl-quinolin-4-yl)-ureido]-ethyl}-piperidin-4-yl)-benzenesulfonamide |
| 151. | 4-Bromo-N-butyl-N-(1-{2-[3-(2-methyl-quinolin-4-yl)-ureido]-ethyl}-pyrrolidin-3-yl)-benzenesulfonamide |
| 152. | N-Benzyl-4-bromo-N-(1-{2-[3-(2-methyl-quinolin-4-yl)-ureido]-ethyl}-piperidin-4-yl)-benzenesulfonamide |
| 153. | N-Benzyl-4-bromo-N-(1-{2-[3-(2-methyl-quinolin-4-yl)-ureido]-ethyl}-pyrrolidin-3-yl)-benzenesulfonamide |

-continued

| Example Number | |
|---|---|
| 154. | 4-Bromo-N-(1-{2-[3-(2-methyl-quinolin-4-yl)-ureido]-ethyl}-piperidin-4-yl)-N-phenethyl-benzenesulfonamide |
| 155. | 4-Bromo-N-(1-{2-[3-(2-methyl-quinolin-4-yl)-ureido]-ethyl}-pyrrolidin-3-yl)-N-phenethyl-benzenesulfonamide |
| 156. | 4-Bromo-N-methyl-N-((R)-1-{2-[3-(2-methyl-quinolin-4-yl)-ureido]-ethyl}-pyrrolidin-3-yl)-benzenesulfonamide |
| 157. | 4-Bromo-N-ethyl-N-((R)-1-{2-[3-(2-methyl-quinolin-4-yl)-ureido]-ethyl}-pyrrolidin-3-yl)-benzenesulfonamide |
| 158. | 4-Bromo-N-ethyl-N-((S)-1-{2-[3-(2-methyl-quinolin-4-yl)-ureido]-ethyl}-pyrrolidin-3-yl)-benzenesulfonamide |
| 159. | 4-Bromo-N-methyl-N-((S)-1-{2-[3-(2-methyl-quinolin-4-yl)-ureido]-ethyl}-pyrrolidin-3-yl)-benzenesulfonamide |
| 160. | N-Ethyl-3-methyl-N-(1-{2-[3-(2-methyl-quinolin-4-yl)-ureido]-ethyl}-piperidin-4-yl)-benzenesulfonamide |
| 161. | N-Ethyl-4-methyl-N-(1-{2-[3-(2-methyl-quinolin-4-yl)-ureido]-ethyl}-piperidin-4-yl)-benzenesulfonamide |
| 162. | N-Ethyl-2-methyl-N-(1-{2-[3-(2-methyl-quinolin-4-yl)-ureido]-ethyl}-piperidin-4-yl)-benzenesulfonamide |
| 163. | 3-Chloro-N-ethyl-N-(1-{2-[3-(2-methyl-quinolin-4-yl)-ureido]-ethyl}-piperidin-4-yl)-benzenesulfonamide |
| 164. | 2-Chloro-N-ethyl-N-(1-{2-[3-(2-methyl-quinolin-4-yl)-ureido]-ethyl}-piperidin-4-yl)-benzenesulfonamide |
| 165. | 4-Chloro-N-ethyl-N-(1-{2-[3-(2-methyl-quinolin-4-yl)-ureido]-ethyl}-piperidin-4-yl)-benzenesulfonamide |
| 166. | N-Ethyl-4-fluoro-N-(1-{2-[3-(2-methyl-quinolin-4-yl)-ureido]-ethyl}-piperidin-4-yl)-benzenesulfonamide |
| 167. | N-Ethyl-4-methoxy-N-(1-{2-[3-(2-methyl-quinolin-4-yl)-ureido]-ethyl}-piperidin-4-yl)-benzenesulfonamide |
| 168. | 3,4-Dichloro-N-ethyl-N-(1-{2-[3-(2-methyl-quinolin-4-yl)-ureido]-ethyl}-piperidin-4-yl)-benzenesulfonamide |
| 169. | N-Ethyl-N-(1-{2-[3-(2-methyl-quinolin-4-yl)-ureido]-ethyl}-piperidin-4-yl)-4-trifluoromethyl-benzenesulfonamide |
| 230. | 1-(2-Methyl-quinolin-4-yl)-3-{2-[4-(3-phenethyl-ureido)-piperidin-1-yl]-ethyl}-urea |
| 384. | 1-[(S)-1-(4-Benzyl-piperidin-1-ylmethyl)-2-methyl-propyl]-3-(2-methyl-quinolin-4-yl)-urea |
| 385. | 1-[(S)-1-Benzyl-2-(4-benzyl-piperidin-1-yl)-ethyl]-3-(2-methyl-quinolin-4-yl)-urea |
| 386. | 1-[(S)-1-(4-Benzyl-piperidin-1-ylmethyl)-3-methyl-butyl]-3-(2-methyl-quinolin-4-yl)-urea |
| 389. | 1-[2-(4-Benzyl-4-hydroxy-piperidin-1-yl)-ethyl]-3-(2-cyclopropyl-quinolin-4-yl)-urea |
| 392. | 1-{2-[4-(3-Methyl-benzylidene)-piperidin-1-yl]-ethyl}-3-(2-methyl-quinolin-4-yl)-urea |
| 394. | 1-{2-[4-(2-Methyl-benzylidene)-piperidin-1-yl]-ethyl}-3-(2-methyl-quinolin-4-yl)-urea |
| 395. | 1-{2-[4-(4-Methoxy-benzylidene)-piperidin-1-yl]-ethyl}-3-(2-methyl-quinolin-4-yl)-urea |
| 396. | 1-{2-[4-(4-Fluoro-benzylidene)-piperidin-1-yl]-ethyl}-3-(2-methyl-quinolin-4-yl)-urea |
| 397. | 1-{2-[4-(4-Bromo-benzylidene)-piperidin-1-yl]-ethyl}-3-(2-methyl-quinolin-4-yl)-urea |
| 398. | 1-{2-[4-(3-Methyl-benzyl)-piperidin-1-yl]-ethyl}-3-(2-methyl-quinolin-4-yl)-urea |
| 399. | 1-{2-[4-(2-Methyl-benzyl)-piperidin-1-yl]-ethyl}-3-(2-methyl-quinolin-4-yl)-urea |
| 401. | 1-{2-[4-(4-Fluoro-benzyl)-piperidin-1-yl]-ethyl}-3-(2-methyl-quinolin-4-yl)-urea |
| 412. | 1-{2-[3-(2-Methyl-quinolin-4-yl)-ureido]-ethyl}-piperidine-4-carboxylic acid benzyl-phenyl-amide |
| 416. | 1-{2-[3-(2-Methyl-quinolin-4-yl)-ureido]-ethyl}-piperidine-4-carboxylic acid (2-chloro-phenyl)-methyl-amide |
| 425. | 1-{2-[3-(2-Methyl-quinolin-4-yl)-ureido]-ethyl}-4-phenyl-piperidine-4-carboxylic acid benzyl-methyl-amide |
| 427. | 1-{2-[3-(2-Methyl-quinolin-4-yl)-ureido]-ethyl}-4-phenyl-piperidine-4-carboxylic acid methyl-phenethyl-amide |
| 428. | 1-{2-[3-(2-Methyl-quinolin-4-yl)-ureido]-ethyl}-4-phenyl-piperidine-4-carboxylic acid benzyl-ethyl-amide |
| 429. | 1-{2-[3-(2-Methyl-quinolin-4-yl)-ureido]-ethyl}-4-phenyl-piperidine-4-carboxylic acid dimethylamide |
| 432. | 4-Benzyl-1-{2-[3-(2-methyl-quinolin-4-yl)-ureido]-ethyl}-piperidine-4-carboxylic acid benzyl-ethyl-amide |

-continued

| Example Number | |
|---|---|
| 447. | 1-[2-(4-Benzyl-4-hydroxy-piperidin-1-yl)-ethyl]-3-(2-methylamino-pyridin-4-yl)-urea |
| 448. | 1-[2-(4-Benzyl-piperidin-1-yl)-ethyl]-3-(2-methylamino-pyridin-4-yl)-urea |

Because of their ability to inhibit the actions of urotensin II, the described compounds can be used for treatment of diseases which are associated with an increase in vasoconstriction, proliferation or other disease states associated with the actions of urotensin II. Examples of such diseases are hypertension, atherosclerosis, angina or myocardial ischemia, congestive heart failure, cardiac insufficiency, cardiac arrhythmias, renal ischemia, chronic kidney disease, renal failure, stroke, cerebral vasospasm, cerebral ischemia, dementia, migraine, subarachnoidal hemorrhage, diabetes, diabetic arteriopathy, diabetic nephropathy, connective tissue diseases, cirrhosis, asthma, chronic obstructive pulmonary disease, high-altitude pulmonary edema, Raynaud's syndrome, portal hypertension, thyroid dysfunction, pulmonary edema, pulmonary hypertension, or pulmonary fibrosis. They can also be used for prevention of restenosis after balloon or stent angioplasty, for the treatment of cancer, prostatic hypertrophy, erectile dysfunction, hearing loss, amaurosis, chronic bronchitis, asthma, gram negative septicemia, shock, sickle cell anemia, sickle cell acute chest syndrome, glomerulonephritis, renal colic, glaucoma, therapy and prophylaxis of diabetic complications, complications of vascular or cardiac surgery or after organ transplantation, complications of cyclosporin treatment, pain, addictions, schizophrenia, Alzheimer's disease, anxiety, obsessive-compulsive behavior, epileptic seizures, stress, depression, dementias, neuromuscular disorders, neurodegenerative diseases, as well as other diseases related to a dysregulation of urotensin II or urotensin II receptors.

These compositions may be administered in enteral or oral form e.g. as tablets, dragees, gelatine capsules, emulsions, solutions or suspensions, in nasal form like sprays and aerosols, or rectally in form of suppositories. These compounds may also be administered in intramuscular, parenteral or intravenous form, e.g. in form of injectable solutions.

These pharmaceutical compositions may contain the compounds of formula 1 as well as their pharmaceutically acceptable salts in combination with inorganic and/or organic excipients, which are usual in the pharmaceutical industry, like lactose, maize or derivatives thereof, talcum, stearic acid or salts of these materials.

For gelatine capsules vegetable oils, waxes, fats, liquid or half-liquid polyols etc. may be used. For the preparation of solutions and sirups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, anti-oxidants etc.

The compounds of general formula 1 may also be used in combination with one or more other therapeutically useful substances e.g. α- and, β-blockers like phentolamine, phenoxybenzamine, atenolol, propranolol, timolol, metoprolol, carteolol, carvedilol, etc.; with vasodilators like hydralazine, minoxidil, diazoxide, flosequinan, etc.; with calcium-antagonists like diltiazem, nicardipine, nimodipine, verapamil, nifedipine, etc.; with angiotensin converting enzyme-inhibitors like cilazapril, captopril, enalapril, lisinopril etc.; with potassium channel activators like pinacidil, chromakalim, etc.; with angiotensin receptor antagonists like losartan, valsartan, candesartan, irbesartan, eprosartan, telmisartan, and tasosartan, etc.; with diuretics like hydrochlorothiazide, chlorothiazide, acetolamide, bumetanide, furosemide, metolazone, chlortalidone, etc.; with sympatholytics like methyldopa, clonidine, guanabenz, reserpine, etc.; with endothelin receptor antagonists like bosentan, tezosentan, darusentan, atrasentan, enrasentan, or sitaxsentan, etc.; with anti-hyperlipidemic agents like lovastatin, pravistatin, fluvastatin, atorvastatin, cerivastatin, simvastatin, etc.; and other therapeutics which serve to treat high blood pressure, vascular disease or other disorders listed above.

The dosage may vary within wide limits but should be adapted to the specific situation. In general the dosage given daily in oral form should be between about 3 mg and about 3 g, preferably between about 10 mg and about 1 g, especially preferred between 5 mg and 300 mg, per adult with a body weight of about 70 kg. The dosage should be administered preferably in 1 to 3 doses of equal weight per day. As usual children should receive lower doses which are adapted to body weight and age.

General Preparation of Compounds of the Invention

Compounds of the general formula 1 can be prepared using methods generally known in the art, according to the general sequence of reactions outlined below. For simplicity and clarity reasons sometimes only a few of the possible synthetic routes that lead to compounds of general formula 1 are described.

For the synthesis of compounds of general formula 1 general synthetic routes illustrated in Schemes A through E can be employed. The generic groups Py, $R^1$, $R^2$, $R^3$, X, Z, Y, n, and m employed in Schemes A through E have the definitions given in general formula 1 above. Other abbreviations used are defined in the Experimental Section. Some instances of the generic groups X and Z might be incompatible with the assembly illustrated in Schemes A through E and so will require the use of protecting groups. The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as are necessary are in place.

Preparation of compounds of general formula 1 wherein Y is —$(CH_2)_m C(R^4)(R^5)$—. Compounds of general formula 1 wherein Y is —$(CH_2)_m C(R^4)(R^5)$— are prepared according to Scheme A. Compounds of general formula 1 wherein Y is —$C(R^4)(R^5)$—$(CH_2)_m$— are prepared according to Scheme B.

Scheme A

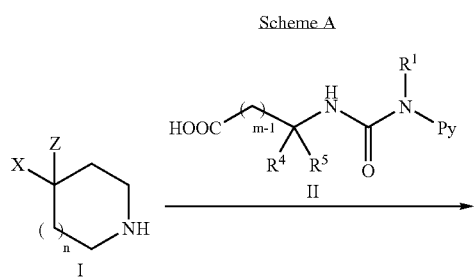

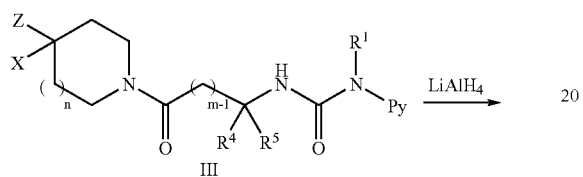

4-Substituted-piperidines and 3-substituted-pyrrolidines of general structure I in Scheme A are either commercially available in racemic or optically active form or are prepared in racemic or optically active form by methods well known in the art.

Ureido acetic- and propionic acid derivatives of general structure 11 in Scheme A are prepared according to Scheme F below. N-Acylation of piperidines and pyrrolidines of general structure I with ureido acetic- and propionic acid derivatives of general structure II is accomplished in a polar solvent such as DMF in the presence of a small stoichiometric excess of a coupling reagent such as a carbodiimide to provide amides of general structure III. Selective reduction of the amide carbonyl group with a reagent such as $LiAlH_4$ in a polar solvent such as THF provides the target compounds of general formula 1 wherein Y is $-(CH_2)_m C(R^4)(R^5)-$.

Preparation of compounds of general formula 1 wherein $R^1$ is H. These compounds are alternatively prepared according to Scheme B.

Scheme B

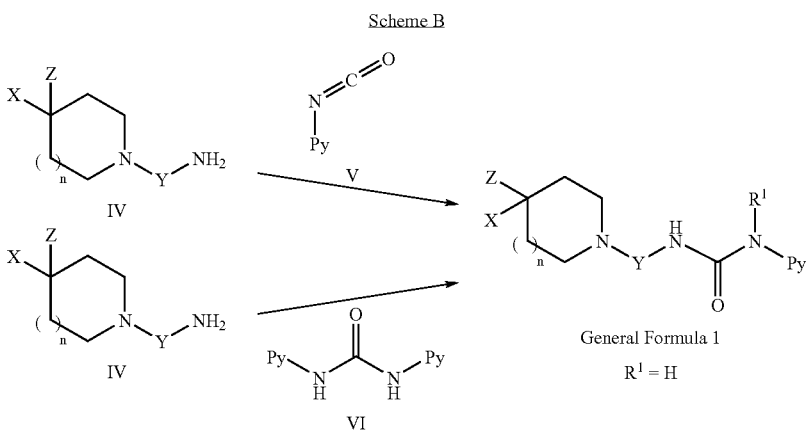

-continued

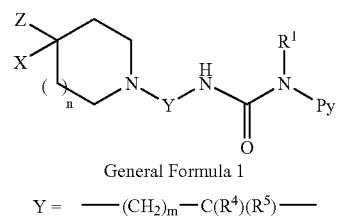

General Formula 1

$Y = -(CH_2)_m-C(R^4)(R^5)-$

Amines of general structure IV are reacted with isocyanates of general structure V or ureas of general structure VI to provide the final compounds of general formula 1 wherein $R^1$ is H. Alternatively, amines of general structure IV are reacted with ureas of general structure VI to provide the final compounds of general formula 1 wherein $R^1$ is H. The preparation of isocyanates of general structure V and of ureas of general structure VI is described in Scheme E below. The preparation of amines of general structure IV is described in Scheme G below.

Compounds of general formula 1 wherein $R^4$ and $R^5$ are H. These compounds are prepared according to the method illustrated in Scheme C.

Scheme C

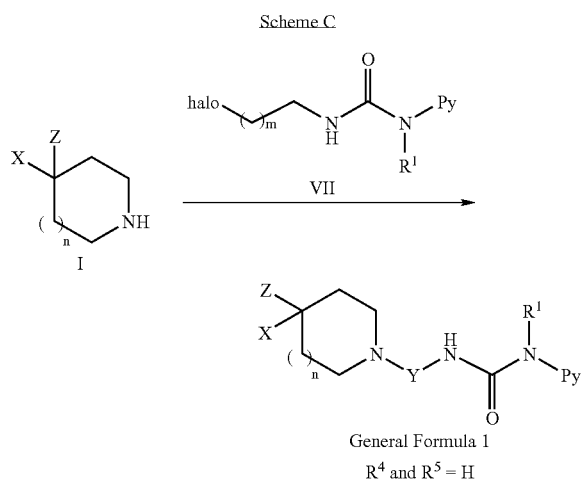

General Formula 1
$R^4$ and $R^5$ = H

4-Substituted-piperidines and 3-substituted-pyrrolidines of general structure I in Scheme C are either commercially available in racemic or optically active form or are prepared in racemic or optically active form by methods well known in the art. Haloalkyl ureas of general structure VII in Scheme C are prepared according to Scheme E below. N-Alkylation of piperidines and pyrrolidines of general structure I with haloalkyl ureas of general structure VII is accomplished in a polar solvent such as tetrahydrofuran in the presence of a sub-stoichiometric amount of an iodide salt such as NaI and a small stoichiometric excess of acid scavenger such as $Na_2CO_3$, to provide the target compounds of general formula 1.

Compounds of general formula 1 wherein X represents lower alkyl-$SO_2NR^2$—; aryl-$SO_2NR^2$—; arylalkyl-$SO_2NR^2$—; lower alkyl-$CONR^2$—; aryl-$CONR^2$—; arylalkyl-$CONR^2$—; lower alkyl-$NR^3CONR^2$—; aryl-$NR^3CONR^2$—; arylalkyl-$NR^3CONR^2$—; and Z, $R^4$ and $R^5$ represent H. These compounds are alternatively prepared according to the method illustrated in Scheme D.

Scheme D

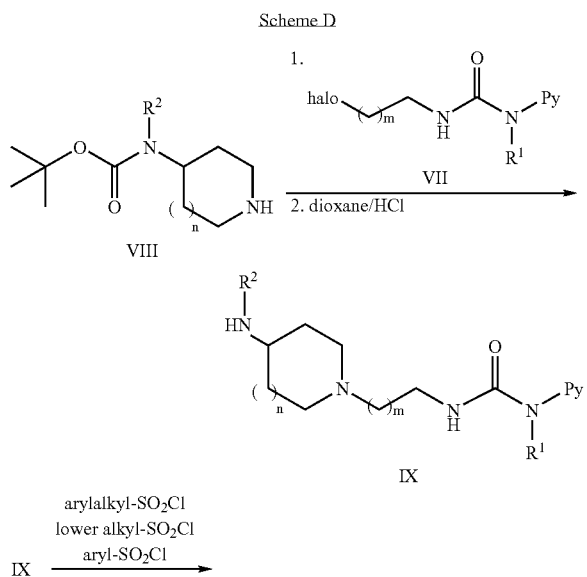

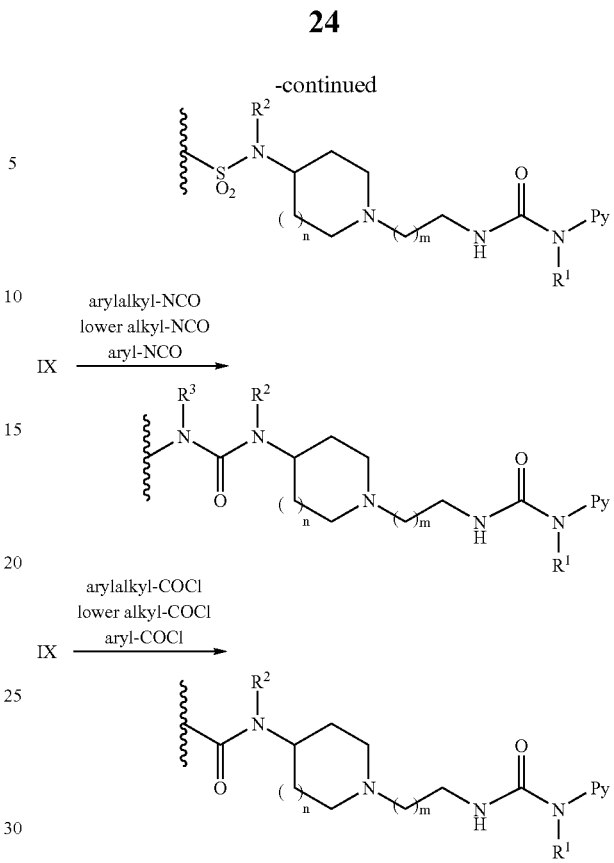

Racemic or chiral carbamates of general structure VIII are either commercially available or readily prepared by methods well known in the art. Haloalkyl ureas of general structure VII are prepared according to Scheme E below. Carbamates of general structure VIII are reacted with haloalkyl ureas of general structure VII in a polar solvent such as tetrahydrofuran in the presence of a substoichiometric amount of an iodide salt such as NaI and a small stoichiometric excess of an acid scavenger such as $Na_2CO_3$, followed by removal of the carbamate group under acidic conditions, such as reaction with TFA in $CH_2Cl_2$. The resulting compounds of general structure IX are converted to final compounds of general formula 1 wherein lower alkyl-$SO_2NR^2$—; aryl-$SO_2NR^2$—; arylalkyl-$SO_2NR^2$—; lower alkyl-$CONR^2$—; aryl-$CONR^2$—; arylalkyl-$CONR^2$—; lower alkyl-$NR^3CONR^2$—; aryl-$NR^3CONR^2$—; arylalkyl-$NR^3CONR^2$—; and Z, $R^4$ and $R^5$ represent H, by reaction with commercially available or well known sulfonylchlorides, isocyanates, or acid chlorides.

Synthetic intermediates used in Schemes A, B, C, and D. Synthetic intermediates containing the group Py, as defined in the general formula 1 above, are obtained by the methods illustrated in Scheme E and F.

Scheme E

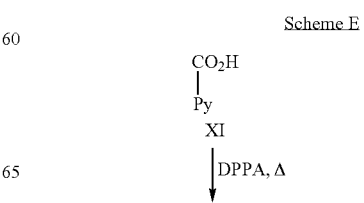

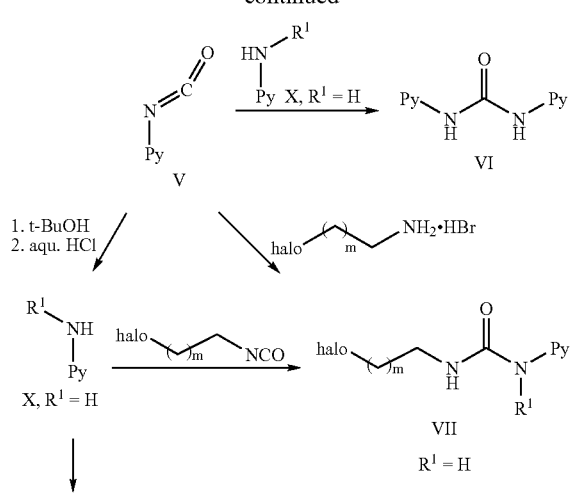

Carboxylic acids of general structure XI are commercially available or are prepared by well known methods. Reaction with diphenylphosphorylazide provides the acyl azide, which undergoes Curtius rearrangement to provide the isocyanates of general structure V, which are used in situ. Isocyanates of general structure V, reacted with halopropylamine hydrochloride or haloethylamine hydrochloride in the presence of an acid scavenger such as DIPEA, provide ureas of general structure VII wherein $R^1$ is H. Isocyanates of general structure V are reacted with tert-butanol to provide the corresponding carbamoyl ester, which is hydrolyzed with aqueous acid such as HCl, to provide amines of general structure X where $R^1$ is H. Alkylation by one of several methods well known in the art, such as reductive amination with a suitable lower aldehyde provides secondary amines of general structure X. Reaction of amines of general structure X with commercially available chloroethylisocyanate or chloropropylisocyanate in a polar aprotic solvent such as tetrahydrofuran provides the ureas of general structure VII.

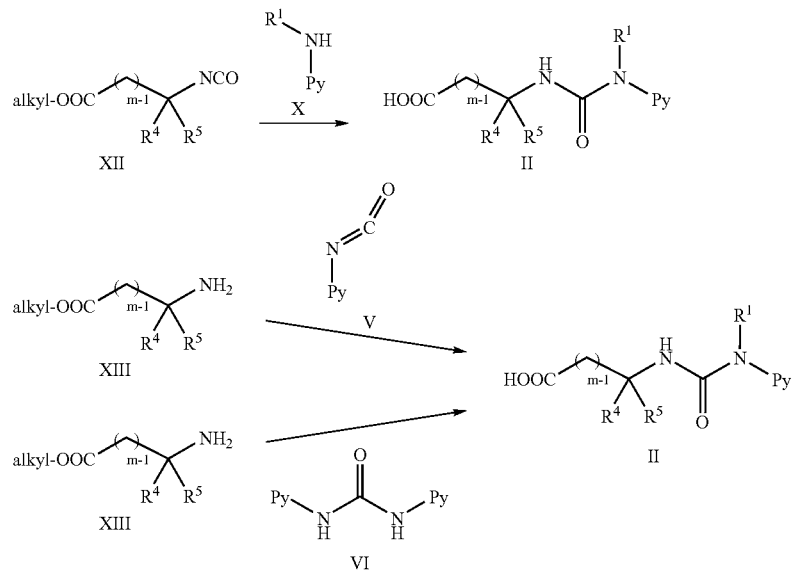

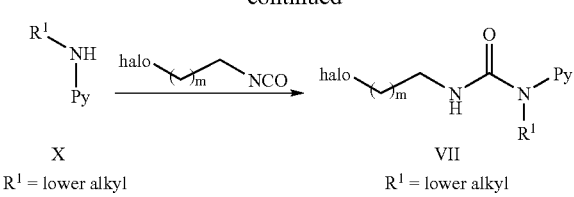

Reaction of amines of general structure X with isocyanates of general structure V provide symmetrical ureas of general structure VI. Reaction of amines of general structure X with commercially available 2- or 3-isocyanato-carboxylic acid esters of general formula XII in a polar aprotic solvent such as tetrahydrofuran, followed by hydrolysis of the ester in aqueous acid such as HCl, provides carboxylic acids of general structure II. Alternatively, isocyanates of general structure V and ureas of general structure VI react with amino acid esters of general structure XIII to provide, after hydrolysis of the ester in aqueous acid such as HCl, carboxylic acids of general structure II.

Synthetic intermediates of general structure IV are obtained by the methods illustrated in Scheme G.

Scheme G

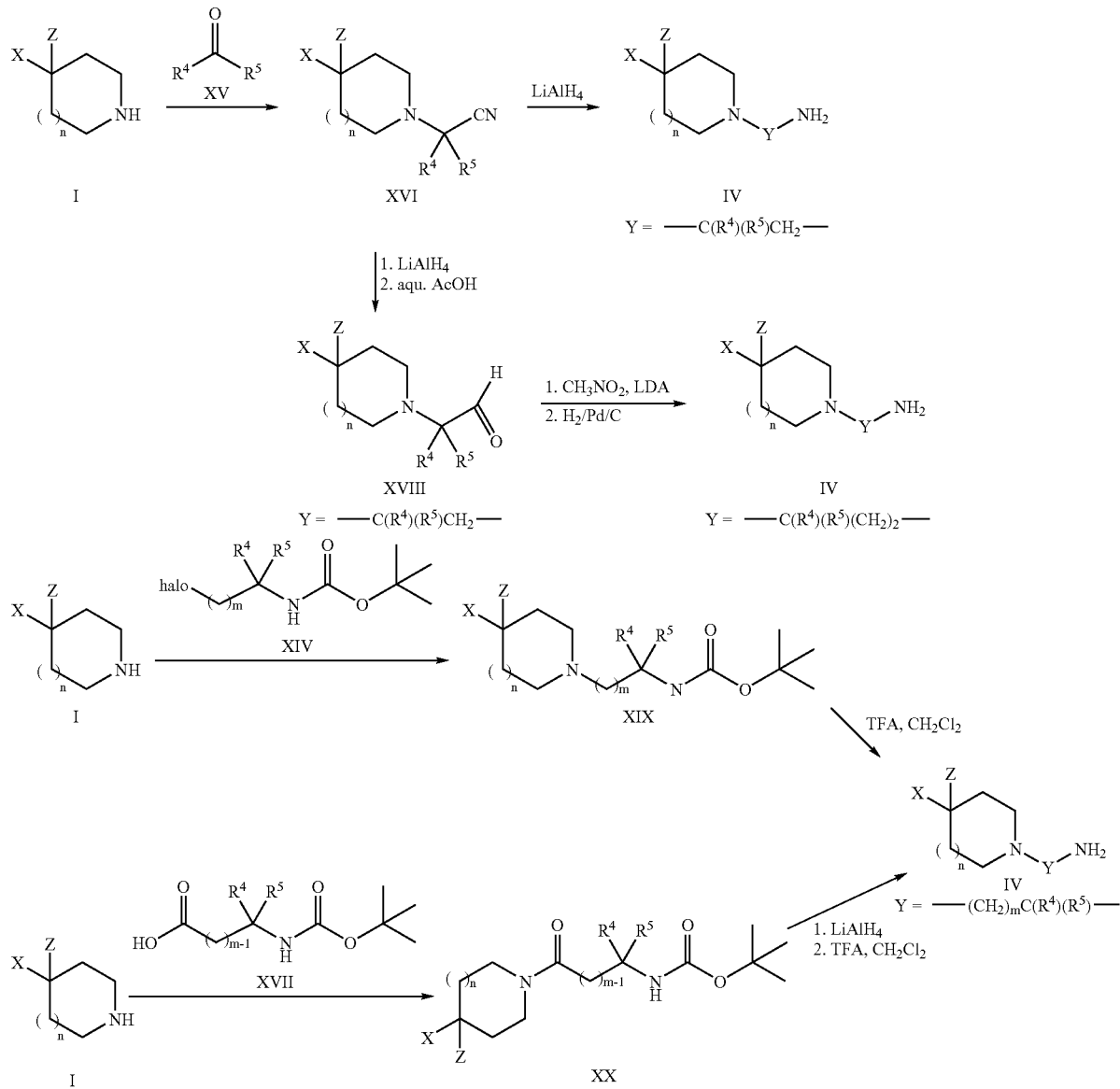

4-Substituted-piperidines and 3-substituted-pyrrolidines of general structure I in Scheme A are either commercially available in racemic or optically active form or are prepared in racemic or optically active form by methods well known in the art. Ketones and aldehydes of general formula XV are commercially available or are prepared by methods well-known in the art. Reaction of ketones and aldehydes of general formula XV with 4-substituted-piperidines and 3-substituted-pyrrolidines of general structure I in presence of a cyanide ion donor such as acetone cyanohydrine provides piperidine and pyrrolidine derivatives of general structure XVI. Complete reduction of the cyano group with a reducing reagent such as LiAlH$_4$ in a polar aprotic solvent such as THF provides the intermediate primary amines of general structure IV, wherein Y is —C(R$^4$)(R$^5$)—CH$_2$—. Partial reduction of the cyano group of compounds of general structure XVI with a reducing reagent such as DIBAL-H, followed by aqueous hydrolysis provides aldehydes of general structure XVIII. Condensation with the nitromethane anion and subsequent reduction, for example by catalytic hydrogenation, provides the intermediate primary amines of general structure IV, wherein Y is —C(R$^4$)(R$^5$)(CH$_2$)$_2$—. Haloalkyl carbamates of general structure XIV in Scheme G are commercially available or are prepared by methods well-known in the art. N-Alkylation of piperidines and pyrrolidines of general structure I with haloalkyl carbamates of general structure XIV is accomplished in a polar solvent such as THF in the presence of a small stoichiometric excess of acid scavenger such as DIPEA to provide compounds of general structure XIX. Cleavage of the resulting carbamate with methods well known in the art, for example with TFA in a solvent such as CH$_2$Cl$_2$, provides the intermediate primary amine derivatives of general structure IV wherein Y is —(CH$_2$)$_m$C(R$^4$)

(R⁵)—. Protected amino acids of general structure XVII are commercially available or are prepared by methods well-known in the art. N-Acylation of piperidines and pyrrolidines of general structure IV with compounds of general structure XVII is accomplished under well-known conditions, for example in a polar solvent such as DMF in the presence of a small stoichiometric excess of a coupling agent such as a carbodiimide, to provide compounds of general structure XX. Reduction with a reagent such as LiAlH$_4$ and deprotection provides intermediate primary amines of general structure IV wherein Y is —(CH$_2$)$_m$C(R⁴)(R⁵)—.

The foregoing general description of the invention will now be further illustrated with a number of non-limiting examples.

EXAMPLES OF THE INVENTION

List of Abbreviations:

| | |
|---|---|
| BSA | bovine serum albumin |
| CDI | N,N-carbonyldiimidazole |
| DIBAL-H | diisobutylaluminum hydride |
| DIPEA | diisopropylethylamine |
| DMF | dimethylformamide |
| DMSO | dimethylsulfoxide |
| DPPA | diphenylphosphoryl azide |
| EDC | N-(3-dimethylaminopropyl)-N'-ethylcarbodiimide hydrochloride |
| EDTA | ethylenediamine tetra-acetic acid |
| ESI | electrospray ionization |
| EtOAc | ethyl acetate |
| Hex | hexane |
| HOBt | 1-hydroxybenzotriazole |
| AcOH | acetic acid |
| HPLC | high performance liquid chromatography |
| LC-MS | liquid chromatography-mass spectroscopy |
| LDA | lithium diisopropylamide |
| MeOH | methanol |
| min | minutes |
| MHz | megahertz |
| MS | mass spectroscopy |
| NaHMDS | sodium bis(trimethylsilyl)amide |
| NMR | nuclear magnetic resonance |
| ppm | part per million |
| PBS | phosphate-buffered saline |
| sat. | saturated |
| T$_3$P | 1-propylphosphonic acid cyclic anhydride |
| TBTU | 2-(1H-benzotriazole-1-yl)-1,1,3,3-tetramethyluronium bromide |
| TEA | triethylamine |
| TFA | trifluoroacetic acid |
| THF | tetrahydrofuran |
| TLC | thin layer chromatography |
| TMSCI | chlorotrimethylsilane |
| t$_R$ | retention time |

Reactions are routinely performed under an inert atmosphere such as N$_2$ gas in air dried glassware. Solvents are used as received from the vendor. Evaporations are performed in a rotary evaporator at reduced pressure and a water bath temperature of 50° C. LC-MS characterizations are performed on a Finnigan HP1100 platform using ESI, and positive ion detection with a Navigator AQK detector. Analytical liquid chromatographic separations are performed by Method A, or where indicated, by Method B. Method A consists of a C18 column of 30×4.6 mm dimensions and a mobile phase consisting of a 1 minute gradient of 2-95% CH$_3$CN (containing 0.013 TFA) in water (containing 0.04% TFA) at a flow rate of 0.45 mL/min. Method B consists of a C18 column of 30×4.6 mm dimensions and an isocratic mobile phase consisting of CH$_3$CN-water (1:9) containing 1% formic acid. Retention time (t$_R$) is given in min. TLC is performed on pre-coated silica gel 60 F$_{254}$ glass-backed plates (Merck). Preparative HPLC is performed on a Varian/Gilson platform using a C18 column of 60×21 mm dimensions and a mobile phase consisting of a gradient of 2 to 95% CH$_3$CN in water containing 0.05% formic acid.

Example 1

N-(1-{2-[3-(2-Methyl-quinolin-4-yl)-ureido]-ethyl}-piperidin-4-yl)-4-trifluoromethyl-benzenesulfonamide 1A. 1-(2-Chloro-ethyl)-3-(2-methyl-quinolin-4-yl)-urea

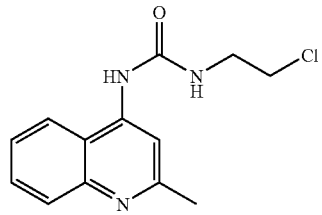

To a solution of 4-amino-2-methylquinoline (12.6 g, 80 mmol) in THF (480 mL) is added 2-chloroethylisocyanate (10.2 mL, 120 mmol) at rt. The reaction mixture is stirred for 40 h at rt. MeOH (100 mL) is added, and stirring is continued an additional hour. The reaction mixture is evaporated and the residue is taken up in CH$_2$Cl$_2$. The organic layer is shaken with 1 N HCl (250 mL), and the resulting precipitate is collected by filtration. The solid is washed with CH$_2$Cl$_2$ (100 mL), saturated NaHCO$_3$ (2×100 mL), and with water (4×100 mL). The resulting solid is dried under HV at rt for 14 h to provide the title compound.

1B. (1-{2-[3-(2-Methyl-quinolin-4-yl)-ureido]-ethyl}-piperidin-4-yl)-carbamic acid tert-butyl ester

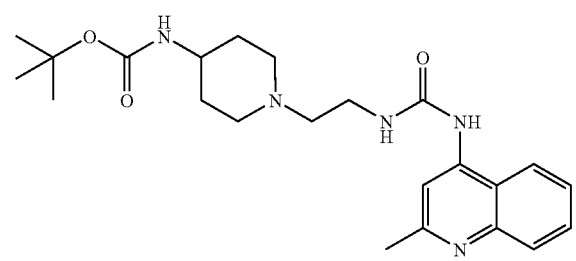

A mixture of piperidin-4-yl-carbamic acid tert-butyl ester (10 mmol), 1-(2-chloro-ethyl)-3-(2-methyl-quinolin-4-yl)-urea (10 mmol), NaHCO$_3$ (20 mmol), NaI (0.5 mmol), and THF (70 mL) is stirred in a sealed vessel at 70° C. for 6 d. The reaction mixture is filtered, evaporated to dryness, and the residue is purified by preparative HPLC to provide the title compound.

1C. 1-[2-(4-Amino-piperidin-1-yl)-ethyl]-3-(2-methyl-quinolin-4-yl)-urea

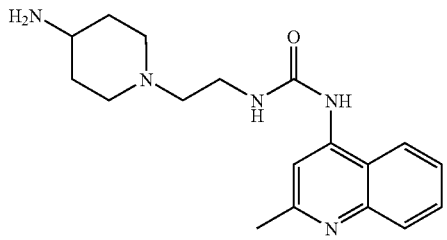

A solution of (1-{2-[3-(2-methyl-quinolin-4-yl)-ureido]-ethyl}piperidin-4-yl)-carbamic acid tert-butyl ester (2.86 g, 5.5 mmol) in AcOH (35 mL) is treated with conc. HCl (3.5 mL). After 30 min, the reaction mixture is frozen and lyophylized to provide the title compound as the dihydrochloride salt.

1D. N-(1-{2-[3-(2-Methyl-quinolin-4-yl)-ureido]-ethyl}-piperidin-4-yl)-4-trifluoromethyl-benzenesulfonamide

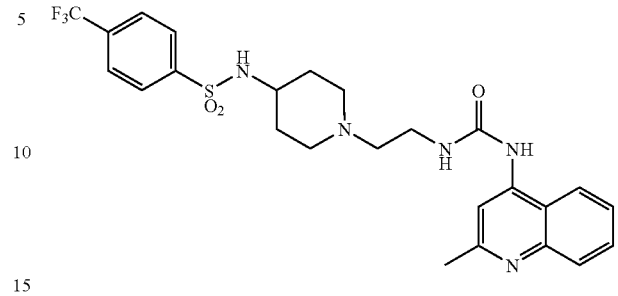

A solution of 4-trifluoromethyl-benzenesulfonyl chloride (0.03 mmol) in THF (1 mL) is added to a mixture of 1-[2-(4-amino-piperidin-1-yl)-ethyl]-3-(2-methyl-quinolin-4-yl)-urea (0.025 mmol), DIPEA (6 μL) and THF (1 mL). The reaction mixture is heated at 40° C. for 18 h, and then is evaporated to dryness. The residue is taken up in formic acid (1 mL), and purified by preparative HPLC to provide the title compound.

The following compounds are prepared analogously:

| | Example | $t_r$ | MS (ES+) |
|---|---|---|---|
| 1. | N-(1-{2-[3-(2-Methyl-quinolin-4-yl)-ureido]-ethyl}-piperidin-4-yl)-4-trifluoromethyl-benzenesulfonamide | 1.04 | 536.2 |
| 2. | N-(1-{2-[3-(2-Methyl-quinolin-4-yl)-ureido]-ethyl}-pyrrolidin-3-yl)-benzenesulfonamide | 0.91 | 454.2 |
| 3. | N-Methyl-N-(1-{2-[3-(2-methyl-quinolin-4-yl)-ureido]-ethyl}-pyrrolidin-3-yl)-benzenesulfonamide | 0.98 | 468.2 |
| 4. | Thiophene-2-sulfonic acid (1-{2-[3-(2-methyl-quinolin-4-yl)-ureido]-ethyl}-piperidin-4-yl)-amide | 0.89 | 474.2 |
| 5. | Thiophene-2-sulfonic acid (1-{2-[3-(2-methyl-quinolin-4-yl)-ureido]-ethyl}-pyrrolidin-3-yl)-amide | 0.89 | 460.2 |
| 6. | Thiophene-2-sulfonic acid methyl-(1-{2-[3-(2-methyl-quinolin-4-yl)-ureido]-ethyl}-pyrrolidin-3-yl)-amide | 0.97 | 474.2 |
| 7. | 3-Methyl-N-(1-{2-[3-(2-methyl-quinolin-4-yl)-ureido]-ethyl}-piperidin-4-yl)-benzenesulfonamide | 1.00 | 482.2 |
| 8. | 3-Methyl-N-(1-{2-[3-(2-methyl-quinolin-4-yl)-ureido]-ethyl}-pyrrolidin-3-yl)-benzenesulfonamide | 1.00 | 468.2 |
| 9. | 3,N-Dimethyl-N-(1-{2-[3-(2-methyl-quinolin-4-yl)-ureido]-ethyl}-pyrrolidin-3-yl)-benzenesulfonamide | 1.06 | 482.2 |
| 10. | 2-Methyl-N-(1-{2-[3-(2-methyl-quinolin-4-yl)-ureido]-ethyl}-piperidin-4-yl)-benzenesulfonamide | 0.99 | 482.2 |
| 11. | 2-Methyl-N-(1-{2-[3-(2-methyl-quinolin-4-yl)-ureido]-ethyl}-pyrrolidin-3-yl)-benzenesulfonamide | 0.99 | 468.2 |
| 12. | 2,N-Dimethyl-N-(1-{2-[3-(2-methyl-quinolin-4-yl)-ureido]-ethyl}-pyrrolidin-3-yl)-benzenesulfonamide | 1.05 | 482.2 |
| 13. | 4-Methyl-N-(1-{2-[3-(2-methyl-quinolin-4-yl)-ureido]-ethyl}-piperidin-4-yl)-benzenesulfonamide | 1.00 | 482.2 |
| 14. | 4-Methyl-N-(1-{2-[3-(2-methyl-quinolin-4-yl)-ureido]-ethyl}-pyrrolidin-3-yl)-benzenesulfonamide | 0.99 | 468.2 |
| 15. | 4,N-Dimethyl-N-(1-{2-[3-(2-methyl-quinolin-4-yl)-ureido]-ethyl}-pyrrolidin-3-yl)-benzenesulfonamide | 1.06 | 482.2 |
| 16. | 2-Fluoro-N-(1-{2-[3-(2-methyl-quinolin-4-yl)-ureido]-ethyl}-piperidin-4-yl)-benzenesulfonamide | 0.92 | 486.2 |
| 17. | 2-Fluoro-N-(1-{2-[3-(2-methyl-quinolin-4-yl)-ureido]-ethyl}-pyrrolidin-3-yl)-benzenesulfonamide | 0.93 | 472.2 |
| 18. | 2-Fluoro-N-methyl-N-(1-{2-[3-(2-methyl-quinolin-4-yl)-ureido]-ethyl}-pyrrolidin-3-yl)-benzenesulfonamide | 1.00 | 486.2 |
| 19. | 3-Fluoro-N-(1-{2-[3-(2-methyl-quinolin-4-yl)-ureido]-ethyl}-piperidin-4-yl)-benzenesulfonamide | 0.98 | 486.2 |
| 20. | 3-Fluoro-N-(1-{2-[3-(2-methyl-quinolin-4-yl)-ureido]-ethyl}-pyrrolidin-3-yl)-benzenesulfonamide | 0.97 | 472.2 |
| 21. | 3-Fluoro-N-methyl-N-(1-{2-[3-(2-methyl-quinolin-4-yl)-ureido]-ethyl}-pyrrolidin-3-yl)-benzenesulfonamide | 1.04 | 486.2 |
| 22. | 4-Fluoro-N-(1-{2-[3-(2-methyl-quinolin-4-yl)-ureido]-ethyl}-piperidin-4-yl)-benzenesulfonamide | 0.97 | 486.2 |

| | Example | $t_r$ | MS (ES+) |
|---|---|---|---|
| 23. | 4-Fluoro-N-(1-{2-[3-(2-methyl-quinolin-4-yl)-ureido]-ethyl}-pyrrolidin-3-yl)-benzenesulfonamide | 0.97 | 472.2 |
| 24. | 4-Fluoro-N-methyl-N-(1-{2-[3-(2-methyl-quinolin-4-yl)-ureido]-ethyl}-pyrrolidin-3-yl)-benzenesulfonamide | 1.03 | 486.2 |
| 25. | 2-Cyano-N-(1-{2-[3-(2-methyl-quinolin-4-yl)-ureido]-ethyl}-piperidin-4-yl)-benzenesulfonamide | 0.93 | 493.2 |
| 26. | 2-Cyano-N-(1-{2-[3-(2-methyl-quinolin-4-yl)-ureido]-ethyl}-pyrrolidin-3-yl)-benzenesulfonamide | 0.88 | 479.2 |
| 27. | 2-Cyano-N-methyl-N-(1-{2-[3-(2-methyl-quinolin-4-yl)-ureido]-ethyl}-pyrrolidin-3-yl)-benzenesulfonamide | 0.99 | 493.2 |
| 28. | 3-Cyano-N-(1-{2-[3-(2-methyl-quinolin-4-yl)-ureido]-ethyl}-piperidin-4-yl)-benzenesulfonamide | 0.95 | 493.2 |
| 29. | 3-Cyano-N-(1-{2-[3-(2-methyl-quinolin-4-yl)-ureido]-ethyl}-pyrrolidin-3-yl)-benzenesulfonamide | 0.95 | 479.2 |
| 30. | 3-Cyano-N-methyl-N-(1-{2-[3-(2-methyl-quinolin-4-yl)-ureido]-ethyl}-pyrrolidin-3-yl)-benzenesulfonamide | 1.02 | 493.2 |
| 31. | 4-Cyano-N-(1-{2-[3-(2-methyl-quinolin-4-yl)-ureido]-ethyl}-piperidin-4-yl)-benzenesulfonamide | 0.96 | 493.2 |
| 32. | 4-Cyano-N-(1-{2-[3-(2-methyl-quinolin-4-yl)-ureido]-ethyl}-pyrrolidin-3-yl)-benzenesulfonamide | 0.96 | 479.2 |
| 33. | 4-Cyano-N-methyl-N-(1-{2-[3-(2-methyl-quinolin-4-yl)-ureido]-ethyl}-pyrrolidin-3-yl)-benzenesulfonamide | 1.02 | 493.2 |
| 34. | 3-Methoxy-N-(1-{2-[3-(2-methyl-quinolin-4-yl)-ureido]-ethyl}-piperidin-4-yl)-benzenesulfonamide | 0.99 | 498.2 |
| 35. | 3-Methoxy-N-(1-{2-[3-(2-methyl-quinolin-4-yl)-ureido]-ethyl}-pyrrolidin-3-yl)-benzenesulfonamide | 0.99 | 484.2 |
| 36. | 3-Methoxy-N-methyl-N-(1-{2-[3-(2-methyl-quinolin-4-yl)-ureido]-ethyl}-pyrrolidin-3-yl)-benzenesulfonamide | 1.04 | 498.2 |
| 37. | 4-Methoxy-N-(1-{2-[3-(2-methyl-quinolin-4-yl)-ureido]-ethyl}-piperidin-4-yl)-benzenesulfonamide | 0.97 | 498.2 |
| 38. | 4-Methoxy-N-(1-{2-[3-(2-methyl-quinolin-4-yl)-ureido]-ethyl}-pyrrolidin-3-yl)-benzenesulfonamide | 0.97 | 484.2 |
| 39. | 4-Methoxy-N-methyl-N-(1-{2-[3-(2-methyl-quinolin-4-yl)-ureido]-ethyl}-pyrrolidin-3-yl)-benzenesulfonamide | 1.03 | 498.2 |
| 40. | 3-Chloro-N-(1-{2-[3-(2-methyl-quinolin-4-yl)-ureido]-ethyl}-piperidin-4-yl)-benzenesulfonamide | 1.06 | 502.2 |
| 41. | 3-Chloro-N-(1-{2-[3-(2-methyl-quinolin-4-yl)-ureido]-ethyl}-pyrrolidin-3-yl)-benzenesulfonamide | 1.05 | 488.2 |
| 42. | 3-Chloro-N-methyl-N-(1-{2-[3-(2-methyl-quinolin-4-yl)-ureido]-ethyl}-pyrrolidin-3-yl)-benzenesulfonamide | 1.10 | 502.2 |
| 43. | 4-Chloro-N-(1-{2-[3-(2-methyl-quinolin-4-yl)-ureido]-ethyl}-piperidin-4-yl)-benzenesulfonamide | 1.06 | 502.1 |
| 44. | 4-Chloro-N-(1-{2-[3-(2-methyl-quinolin-4-yl)-ureido]-ethyl}-pyrrolidin-3-yl)-benzenesulfonamide | 1.06 | 488.2 |
| 45. | 2-Chloro-N-(1-{2-[3-(2-methyl-quinolin-4-yl)-ureido]-ethyl}-piperidin-4-yl)-benzenesulfonamide | 0.98 | 502.2 |
| 46. | 2-Chloro-N-(1-{2-[3-(2-methyl-quinolin-4-yl)-ureido]-ethyl}-pyrrolidin-3-yl)-benzenesulfonamide | 0.97 | 488.2 |
| 47. | 1-Methyl-1H-imidazole-4-sulfonic acid (1-{2-[3-(2-methyl-quinolin-4-yl)-ureido]-ethyl}-piperidin-4-yl)-amide | 0.62 | 472.2 |
| 48. | 1-Methyl-1H-imidazole-4-sulfonic acid (1-{2-[3-(2-methyl-quinolin-4-yl)-ureido]-ethyl}-pyrrolidin-3-yl)-amide | 0.62 | 458.2 |
| 49. | 1-Methyl-1H-imidazole-4-sulfonic acid methyl-(1-{2-[3-(2-methyl-quinolin-4-yl)-ureido]-ethyl}-pyrrolidin-3-yl)-amide | 0.67 | 472.2 |
| 50. | 3,4-Difluoro-N-(1-{2-[3-(2-methyl-quinolin-4-yl)-ureido]-ethyl}-piperidin-4-yl)-benzenesulfonamide | 0.93 | 504.2 |
| 51. | 3,4-Difluoro-N-(1-{2-[3-(2-methyl-quinolin-4-yl)-ureido]-ethyl}-pyrrolidin-3-yl)-benzenesulfonamide | 0.91 | 490.2 |
| 52. | 3,4-Difluoro-N-methyl-N-(1-{2-[3-(2-methyl-quinolin-4-yl)-ureido]-ethyl}-pyrrolidin-3-yl)-benzenesulfonamide | 0.98 | 504.2 |
| 53. | Biphenyl-4-sulfonic acid (1-{2-[3-(2-methyl-quinolin-4-yl)-ureido]-ethyl}-piperidin-4-yl)-amide | 1.06 | 544.2 |
| 54. | Biphenyl-4-sulfonic acid (1-{2-[3-(2-methyl-quinolin-4-yl)-ureido]-ethyl}-pyrrolidin-3-yl)-amide | 1.06 | 530.2 |
| 55. | Biphenyl-4-sulfonic acid methyl-(1-{2-[3-(2-methyl-quinolin-4-yl)-ureido]-ethyl}-pyrrolidin-3-yl)-amide | 1.08 | 544.2 |
| 56. | N-(1-{2-[3-(2-Methyl-quinolin-4-yl)-ureido]-ethyl}-piperidin-4-yl)-4-propyl-benzenesulfonamide | 1.05 | 510.2 |
| 57. | N-(1-{2-[3-(2-Methyl-quinolin-4-yl)-ureido]-ethyl}-pyrrolidin-3-yl)-4-propyl-benzenesulfonamide | 1.04 | 496.2 |
| 58. | N-Methyl-N-(1-{2-[3-(2-methyl-quinolin-4-yl)-ureido]-ethyl}-pyrrolidin-3-yl)-4-propyl-benzenesulfonamide | 1.08 | 510.2 |

-continued

| | Example | $t_r$ | MS (ES+) |
|---|---|---|---|
| 59. | 3-(1-{2-[3-(2-Methyl-quinolin-4-yl)-ureido]-ethyl}-piperidin-4-ylsulfamoyl)-benzoic acid | 0.60 | 512.2 |
| 60. | 3-(1-(2-[3-(2-Methyl-quinolin-4-yl)-ureido]-ethyl)-pyrrolidin-3-ylsulfamoyl)-benzoic acid | 0.60 | 498.2 |
| 61. | 3-[Methyl-(1-{2-[3-(2-methyl-quinolin-4-yl)-ureido]-ethyl}-pyrrolidin-3-yl)-sulfamoyl]-benzoic acid | 0.60 | 512.2 |
| 62. | Naphthalene-2-sulfonic acid (1-{2-[3-(2-methyl-quinolin-4-yl)-ureido]-ethyl}-piperidin-4-yl)-amide | 1.03 | 518.2 |
| 63. | Naphthalene-2-sulfonic acid (1-(2-{3-(2-methyl-quinolin-4-yl)-ureido]-ethyl}-pyrrolidin-3-yl)-amide | 1.02 | 504.2 |
| 64. | Naphthalene-2-sulfonic acid methyl-(1-{2-[3-(2-methyl-quinolin-4-yl)-ureido]-ethyl}-pyrrolidin-3-yl)-amide | 1.04 | 518.2 |
| 65. | Naphthalene-1-sulfonic acid (1-{2-[3-(2-methyl-quinolin-4-yl)-ureido]-ethyl}-piperidin-4-yl)-amide | 1.00 | 518.2 |
| 66. | Naphthalene-1-sulfonic acid (1-{2-[3-(2-methyl-quinolin-4-yl)-ureido]-ethyl}-pyrrolidin-3-yl)-amide | 0.99 | 504.2 |
| 67. | Naphthalene-1-sulfonic acid methyl-(1-{2-[3-(2-methyl-quinolin-4-yl)-ureido]-ethyl}-pyrrolidin-3-yl)-amide | 1.04 | 518.2 |
| 68. | Quinoline-8-sulfonic acid (1-{2-[3-(2-methyl-quinolin-4-yl)-ureido]-ethyl}-piperidin-4-yl)-amide | 0.87 | 519.2 |
| 69. | Quinoline-8-sulfonic acid (1-{2-[3-(2-methyl-quinolin-4-yl)-ureido]-ethyl}-pyrrolidin-3-yl)-amide | 0.85 | 505.2 |
| 70. | Quinoline-8-sulfonic acid methyl-(1-{2-[3-(2-methyl-quinolin-4-yl)-ureido]-ethyl}-pyrrolidin-3-yl)-amide | 0.87 | 519.2 |
| 71. | 4-tert-Butyl-N-(1-{2-[3-(2-methyl-quinolin-4-yl)-ureido]-ethyl}-piperidin-4-yl)-benzenesulfonamide | 1.07 | 524.2 |
| 72. | 4-tert-Butyl-N-(1-{2-[3-(2-methyl-quinolin-4-yl)-ureido]-ethyl}-pyrrolidin-3-yl)-benzenesulfonamide | 1.07 | 510.2 |
| 73. | 4-tert-Butyl-N-methyl-N-(1-{2-[3-(2-methyl-quinolin-4-yl)-ureido]-ethyl}-pyrrolidin-3-yl)-benzenesulfonamide | 1.09 | 524.2 |
| 74. | N-[4-(1-{2-[3-(2-Methyl-quinolin-4-yl)-ureido]-ethyl}-piperidin-4-ylsulfamoyl)-phenyl]-acetamide | 0.76 | 525.2 |
| 75. | N-[4-(1-{2-[3-(2-Methyl-quinolin-4-yl)-ureido]-ethyl}-pyrrolidin-3-ylsulfamoyl)-phenyl]-acetamide | 0.76 | 511.2 |
| 76. | N-{4-[Methyl-(1-{2-[3-(2-methyl-quinolin-4-yl)-ureido]-ethyl}-pyrrolidin-3-yl)-sulfamoyl]-phenyl}-acetamide | 0.81 | 525.2 |
| 77. | N-(1-{2-[3-(2-Methyl-quinolin-4-yl)-ureido]-ethyl}-pyrrolidin-3-yl)-4-trifluoromethyl-benzenesulfonamide | 1.03 | 522.2 |
| 78. | N-Methyl-N-(1-{2-[3-(2-methyl-quinolin-4-yl)-ureido]-ethyl}-pyrrolidin-3-yl)-4-trifluoromethyl-benzenesulfonamide | 1.06 | 536.2 |
| 79. | N-(1-{2-[3-(2-Methyl-quinolin-4-yl)-ureido]-ethyl}-piperidin-4-yl)-2-trifluoromethyl-benzenesulfonamide | 0.97 | 536.2 |
| 80. | N-(1-{2-[3-(2-Methyl-quinolin-4-yl)-ureido]-ethyl}-pyrrolidin-3-yl)-2-trifluoromethyl-benzenesulfonamide | 0.95 | 522.1 |
| 81. | N-Methyl-N-(1-{2-[3-(2-methyl-quinolin-4-yl)-ureido]-ethyl}-pyrrolidin-3-yl)-2-trifluoromethyl-benzenesulfonamide | 1.02 | 536.2 |
| 82. | N-(1-{2-[3-(2-Methyl-quinolin-4-yl)-ureido]-ethyl}-piperidin-4-yl)-3-trifluoromethyl-benzenesulfonamide | 1.03 | 536.2 |
| 83. | N-(1-{2-[3-(2-Methyl-quinolin-4-yl)-ureido]-ethyl}-pyrrolidin-3-yl)-3-trifluoromethyl-benzenesulfonamide | 1.02 | 522.2 |
| 84. | N-Methyl-N-(1-{2-[3-(2-methyl-quinolin-4-yl)-ureido]-ethyl}-pyrrolidin-3-yl)-3-trifluoromethyl-benzenesulfonamide | 1.05 | 536.2 |
| 85. | 3,4-Dichloro-N-(1-{2-[3-(2-methyl-quinolin-4-yl)-ureido]-ethyl}-piperidin-4-yl)-benzenesulfonamide | 1.05 | 536.1 |
| 86. | 3,4-Dichloro-N-(1-{2-[3-(2-methyl-quinolin-4-yl)-ureido]-ethyl}-pyrrolidin-3-yl)-benzenesulfonamide | 1.04 | 522.1 |
| 87. | 3,4-Dichloro-N-methyl-N-(1-{2-[3-(2-methyl-quinolin-4-yl)-ureido]-ethyl}-pyrrolidin-3-yl)-benzenesulfonamide | 1.07 | 536.1 |
| 88. | N-(1-{2-[3-(2-Methyl-quinolin-4-yl)-ureido]-ethyl}-piperidin-4-yl)-4-pentyl-benzenesulfonamide | 1.11 | 538.3 |
| 89. | N-(1-{2-[3-(2-Methyl-quinolin-4-yl)-ureido]-ethyl}-pyrrolidin-3-yl)-4-pentyl-benzenesulfonamide | 1.10 | 524.2 |
| 90. | N-Methyl-N-(1-{2-[3-(2-methyl-quinolin-4-yl)-ureido]-ethyl}-pyrrolidin-3-yl)-4-pentyl-benzenesulfonamide | 1.12 | 538.3 |
| 91. | 4-Butoxy-N-(1-{2-[3-(2-methyl-quinolin-4-yl)-ureido]-ethyl}-piperidin-4-yl)-benzenesulfonamide | 1.08 | 540.2 |
| 92. | 4-Butoxy-N-(1-{2-[3-(2-methyl-quinolin-4-yl)-ureido]-ethyl}-pyrrolidin-3-yl)-benzenesulfonamide | 1.08 | 526.2 |
| 93. | 4-Butoxy-N-methyl-N-(1-{2-[3-(2-methyl-quinolin-4-yl)-ureido]-ethyl}-pyrrolidin-3-yl)-benzenesulfonamide | 1.09 | 540.2 |

-continued

| | Example | t_r | MS (ES+) |
|---|---|---|---|
| 94. | 4,5-Dichloro-thiophene-2-sulfonic acid (1-{2-[3-(2-methyl-quinolin-4-yl)-ureido]-ethyl}-piperidin-4-yl)-amide | 1.05 | 542.1 |
| 95. | 4,5-Dichloro-thiophene-2-sulfonic acid (1-{2-[3-(2-methyl-quinolin-4-yl)-ureido]-ethyl}-pyrrolidin-3-yl)-amide | 1.04 | 528.0 |
| 96. | 4,5-Dichloro-thiophene-2-sulfonic acid methyl-(1-{2-[3-(2-methyl-quinolin-4-yl)-ureido]-ethyl}-pyrrolidin-3-yl)-amide | 1.06 | 542.0 |
| 97. | 4-(3-Chloro-2-cyano-phenoxy)-N-(1-{2-[3-(2-methyl-quinolin-4-yl)-ureido]-ethyl}-piperidin-4-yl)-benzenesulfonamide | 1.08 | 619.2 |
| 98. | 4-(3-Chloro-2-cyano-phenoxy)-N-(1-{2-[3-(2-methyl-quinolin-4-yl)-ureido]-ethyl}-pyrrolidin-3-yl)-benzenesulfonamide | 1.08 | 605.2 |
| 99. | 4-(3-Chloro-2-cyano-phenoxy)-N-methyl-N-(1-{2-[3-(2-methyl-quinolin-4-yl)-ureido]-ethyl}-pyrrolidin-3-yl)-benzenesulfonamide | 1.09 | 619.2 |
| 100. | 2-Methanesulfonyl-N-(1-{2-[3-(2-methyl-quinolin-4-yl)-ureido]-ethyl}-piperidin-4-yl)-benzenesulfonamide | 0.86 | 546.2 |
| 101. | 2-Methanesulfonyl-N-(1-{2-[3-(2-methyl-quinolin-4-yl)-ureido]-ethyl}-pyrrolidin-3-yl)-benzenesulfonamide | 0.83 | 532.1 |
| 102. | 2-Methanesulfonyl-N-methyl-N-(1-{2-[3-(2-methyl-quinolin-4-yl)-ureido]-ethyl}-pyrrolidin-3-yl)-benzenesulfonamide | 0.83 | 546.1 |
| 103. | N-[4-Methyl-5-(1-{2-[3-(2-methyl-quinolin-4-yl)-ureido]-ethyl}-piperidin-4-ylsulfamoyl)-thiazol-2-yl]-acetamide | 0.79 | 546.2 |
| 104. | N-[4-Methyl-5-(1-{2-[3-(2-methyl-quinolin-4-yl)-ureido]-ethyl}-pyrrolidin-3-ylsulfamoyl)-thiazol-2-yl]-acetamide | 0.79 | 532.2 |
| 105. | N-{4-Methyl-5-[methyl-(1-{2-[3-(2-methyl-quinolin-4-yl)-ureido]-ethyl}-pyrrolidin-3-yl)-sulfamoyl]-thiazol-2-yl}-acetamide | 0.85 | 546.2 |
| 106. | 3-Bromo-N-(1-{2-[3-(2-methyl-quinolin-4-yl)-ureido]-ethyl}-piperidin-4-yl)-benzenesulfonamide | 0.98 | 546.1 |
| 107. | 3-Bromo-N-(1-{2-[3-(2-methyl-quinolin-4-yl)-ureido]-ethyl}-pyrrolidin-3-yl)-benzenesulfonamide | 0.96 | 532.0 |
| 108. | 3-Bromo-N-methyl-N-(1-{2-[3-(2-methyl-quinolin-4-yl)-ureido]-ethyl}-pyrrolidin-3-yl)-benzenesulfonamide | 1.02 | 546.0 |
| 109. | 4-Bromo-N-(1-{2-[3-(2-methyl-quinolin-4-yl)-ureido]-ethyl}-piperidin-4-yl)-benzenesulfonamide | 0.98 | 546.1 |
| 110. | 4-Bromo-N-(1-{2-[3-(2-methyl-quinolin-4-yl)-ureido]-ethyl}-pyrrolidin-3-yl)-benzenesulfonamide | 0.97 | 532.0 |
| 111. | 4-Bromo-N-methyl-N-(1-{2-[3-(2-methyl-quinolin-4-yl)-ureido]-ethyl}-pyrrolidin-3-yl)-benzenesulfonamide | 1.03 | 546.1 |
| 112. | N-(1-{2-[3-(2-Methyl-quinolin-4-yl)-ureido]-ethyl}-piperidin-4-yl)-2-trifluoromethoxy-benzenesulfonamide | 1.00 | 552.1 |
| 113. | N-(1-{2-[3-(2-Methyl-quinolin-4-yl)-ureido]-ethyl}-pyrrolidin-3-yl)-2-trifluoromethoxy-benzenesulfonamide | 0.99 | 538.1 |
| 114. | N-Methyl-N-(1-{2-[3-(2-methyl-quinolin-4-yl)-ureido]-ethyl}-pyrrolidin-3-yl)-2-trifluoromethoxy-benzenesulfonamide | 1.04 | 552.2 |
| 115. | N-(1-{2-[3-(2-Methyl-quinolin-4-yl)-ureido]-ethyl}-piperidin-4-yl)-4-trifluoromethoxy-benzenesulfonamide | 1.05 | 552.1 |
| 116. | N-(1-{2-[3-(2-Methyl-quinolin-4-yl)-ureido]-ethyl}-pyrrolidin-3-yl)-4-trifluoromethoxy-benzenesulfonamide | 1.04 | 538.1 |
| 117. | N-Methyl-N-(1-{2-[3-(2-methyl-quinolin-4-yl)-ureido]-ethyl}-pyrrolidin-3-yl)-4-trifluoromethoxy-benzenesulfonamide | 1.06 | 552.1 |
| 118. | 5-Dimethylamino-naphthalene-1-sulfonic acid (1-{2-[3-(2-methyl-quinolin-4-yl)-ureido]-ethyl}-piperidin-4-yl)-amide | 0.94 | 561.2 |
| 119. | 5-Dimethylamino-naphthalene-1-sulfonic acid (1-{2-[3-(2-methyl-quinolin-4-yl)-ureido]-ethyl}-pyrrolidin-3-yl)-amide | 0.97 | 547.2 |
| 120. | 5-Dimethylamino-naphthalene-1-sulfonic acid methyl-(1-{2-[3-(2-methyl-quinolin-4-yl)-ureido]-ethyl}-pyrrolidin-3-yl)-amide | 1.04 | 561.2 |
| 121. | 5-Chloro-3-methyl-benzo[b]thiophene-2-sulfonic acid (1-{2-[3-(2-methyl-quinolin-4-yl)-ureido]-ethyl}-piperidin-4-yl)-amide | 1.09 | 572.2 |

-continued

| | Example | $t_r$ | MS (ES+) |
|---|---|---|---|
| 122. | 5-Chloro-3-methyl-benzo[b]thiophene-2-sulfonic acid (1-{2-[3-(2-methyl-quinolin-4-yl)-ureido]-ethyl}-pyrrolidin-3-yl)-amide | 1.09 | 558.1 |
| 123. | 5-Chloro-3-methyl-benzo[b]thiophene-2-sulfonic acid methyl-(1-{2-[3-(2-methyl-quinolin-4-yl)-ureido]-ethyl}-pyrrolidin-3-yl)-amide | 1.10 | 572.1 |
| 124. | 4-Bromo-2-ethyl-N-(1-{2-[3-(2-methyl-quinolin-4-yl)-ureido]-ethyl}-piperidin-4-yl)-benzenesulfonamide | 1.07 | 574.1 |
| 125. | 4-Bromo-2-ethyl-N-(1-{2-[3-(2-methyl-quinolin-4-yl)-ureido]-ethyl}-pyrrolidin-3-yl)-benzenesulfonamide | 1.06 | 560.1 |
| 126. | 4-Bromo-2-ethyl-N-methyl-N-(1-{2-[3-(2-methyl-quinolin-4-yl)-ureido]-ethyl}-pyrrolidin-3-yl)-benzenesulfonamide | 1.09 | 574.1 |
| 127. | N-(1-{2-[3-(2-Methyl-quinolin-4-yl)-ureido]-ethyl}-piperidin-4-yl)-3,5-bis-trifluoromethyl-benzenesulfonamide | 1.09 | 604.1 |
| 128. | N-(1-{2-[3-(2-Methyl-quinolin-4-yl)-ureido]-ethyl}-pyrrolidin-3-yl)-3,5-bis-trifluoromethyl-benzenesulfonamide | 1.09 | 590.1 |
| 129. | N-Methyl-N-(1-{2-[3-(2-methyl-quinolin-4-yl)-ureido]-ethyl}-pyrrolidin-3-yl)-3,5-bis-trifluoromethyl-benzenesulfonamide | 1.10 | 604.2 |
| 130. | N-[5-(1-{2-[3-(2-Methyl-quinolin-4-yl)-ureido]-ethyl}-piperidin-4-ylsulfamoyl)-thiophen-2-ylmethyl]-benzamide | 0.96 | 607.2 |
| 131. | N-[5-(1-{2-[3-(2-Methyl-quinolin-4-yl)-ureido]-ethyl}-pyrrolidin-3-ylsulfamoyl)-thiophen-2-ylmethyl]-benzamide | 0.94 | 593.1 |
| 132. | N-{5-[Methyl-(1-{2-[3-(2-methyl-quinolin-4-yl)-ureido]-ethyl}-pyrrolidin-3-yl)-sulfamoyl]-thiophen-2-ylmethyl}-benzamide | 0.99 | 607.2 |
| 133. | 4-Benzenesulfonyl-thiophene-2-sulfonic acid (1-{2-[3-(2-methyl-quinolin-4-yl)-ureido]-ethyl}-piperidin-4-yl)-amide | 1.04 | 614.1 |
| 134. | 4-Benzenesulfonyl-thiophene-2-sulfonic acid (1-{2-[3-(2-methyl-quinolin-4-yl)-ureido]-ethyl}-pyrrolidin-3-yl)-amide | 1.03 | 600.1 |
| 135. | 4-Benzenesulfonyl-thiophene-2-sulfonic acid methyl-(1-{2-[3-(2-methyl-quinolin-4-yl)-ureido]-ethyl}-pyrrolidin-3-yl)-amide | 1.05 | 614.1 |
| 136. | 2-(2,2,2-Trifluoro-acetyl)-1,2,3,4-tetrahydro-isoquinoline-7-sulfonic acid (1-{2-[3-(2-methyl-quinolin-4-yl)-ureido]-ethyl}-piperidin-4-yl)-amide | 1.03 | 619.2 |
| 137. | 2-(2,2,2-Trifluoro-acetyl)-1,2,3,4-tetrahydro-isoquinoline-7-sulfonic acid (1-{2-[3-(2-methyl-quinolin-4-yl)-ureido]-ethyl}-pyrrolidin-3-yl)-amide | 1.03 | 605.1 |
| 138. | 2-(2,2,2-Trifluoro-acetyl)-1,2,3,4-tetrahydro-isoquinoline-7-sulfonic acid methyl-(1-{2-[3-(2-methyl-quinolin-4-yl)-ureido]-ethyl}-pyrrolidin-3-yl)-amide | 1.05 | 619.2 |
| 139. | N-(1-{2-[3-(2-Methyl-quinolin-4-yl)-ureido]-ethyl}-piperidin-4-yl)-C-phenyl-methanesulfonamide | 0.73 | 482.2 |
| 140. | Octane-1-sulfonic acid (1-{2-[3-(2-methyl-quinolin-4-yl)-ureido]-ethyl}-piperidin-4-yl)-amide | 1.05 | 504.3 |
| 141. | 2-Phenyl-ethanesulfonic acid (1-{2-[3-(2-methyl-quinolin-4-yl)-ureido]-ethyl}-piperidin-4-yl)-amide | 0.87 | 496.2 |
| 142. | 4-Chloro-N-methyl-N-(1-{2-[3-(2-methyl-quinolin-4-yl)-ureido]-ethyl}-pyrrolidin-3-yl)-benzenesulfonamide | 1.01 | 502.1 |

Example 143

4-Bromo-N-ethyl-N-(1-{2-[3-(2-methyl-quinolin-4-yl)-ureido]-ethyl}-piperidin-4-yl)-benzenesulfonamide

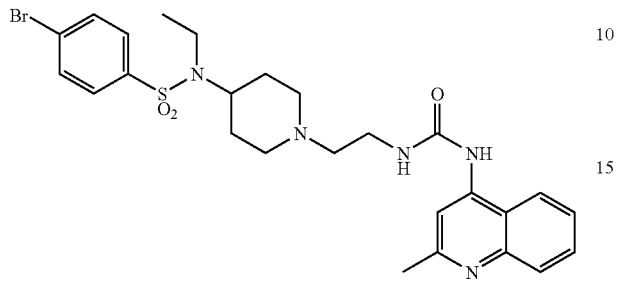

To a solution of 4-bromo-N-(1-{2-[3-(2-methyl-quinolin-4-yl)-ureido]-ethyl}-piperidin-4-yl)-benzenesulfonamide (Example 109., 27.3 mg, 0.05 mmol) in DMSO (1 mL) are added ethyliodide (7.8 mg, 0.05 mmol) and $CsCO_3$ (40 mg, 12 mmol). The reaction mixture is stirred at room temperature for 3 h and then quenched with formic acid (0.25 mL). The reaction mixture is purified by preparative HPLC to provide the title compound.

The following compounds are prepared analogously:

| | Example | $t_r$ | MS (ES+) |
|---|---|---|---|
| 143. | 4-Bromo-N-ethyl-N-(1-{2-[3-(2-methyl-quinolin-4-yl)-ureido]-ethyl}-piperidin-4-yl)-benzenesulfonamide | 1.06 | 574.03 |
| 144. | 4-Bromo-N-methyl-N-(1-{2-[3-(2-methyl-quinolin-4-yl)-ureido]-ethyl}-piperidin-4-yl)-benzenesulfonamide | 1.05 | 559.99 |
| 145. | 4-Bromo-N-ethyl-N-(1-{2-[3-(2-methyl-quinolin-4-yl)-ureido]-ethyl}-pyrrolidin-3-yl)-benzenesulfonamide | 1.05 | 559.99 |
| 146. | 4-Bromo-N-(1-{2-[3-(2-methyl-quinolin-4-yl)-ureido]-ethyl}-piperidin-4-yl)-N-propyl-benzenesulfonamide | 1.09 | 588.06 |
| 147. | 4-Bromo-N-(1-{2-[3-(2-methyl-quinolin-4-yl)-ureido]-ethyl}-pyrrolidin-3-yl)-N-propyl-benzenesulfonamide | 1.07 | 574.02 |
| 148. | 4-Bromo-N-isobutyl-N-(1-{2-[3-(2-methyl-quinolin-4-yl)-ureido]-ethyl}-piperidin-4-yl)-benzenesulfonamide | 1.11 | 602.02 |
| 149. | 4-Bromo-N-isobutyl-N-(1-{2-[3-(2-methyl-quinolin-4-yl)-ureido]-ethyl}-pyrrolidin-3-yl)-benzenesulfonamide | 1.09 | 588.03 |
| 150. | 4-Bromo-N-butyl-N-(1-{2-[3-(2-methyl-quinolin-4-yl)-ureido]-ethyl}-piperidin-4-yl)-benzenesulfonamide | 1.1 | 602.06 |
| 151. | 4-Bromo-N-butyl-N-(1-{2-[3-(2-methyl-quinolin-4-yl)-ureido]-ethyl}-pyrrolidin-3-yl)-benzenesulfonamide | 1.09 | 588.04 |
| 152. | N-Benzyl-4-bromo-N-(1-{2-[3-(2-methyl-quinolin-4-yl)-ureido]-ethyl}-piperidin-4-yl)-benzenesulfonamide | 1.11 | 636.03 |
| 153. | N-Benzyl-4-bromo-N-(1-{2-[3-(2-methyl-quinolin-4-yl)-ureido]-ethyl}-pyrrolidin-3-yl)-benzenesulfonamide | 1.1 | 622 |
| 154. | 4-Bromo-N-(1-{2-[3-(2-methyl-quinolin-4-yl)-ureido]-ethyl}-piperidin-4-yl)-N-phenethyl-benzenesulfonamide | 1.13 | 650.02 |
| 155. | 4-Bromo-N-(1-{2-[3-(2-methyl-quinolin-4-yl)-ureido]-ethyl}-pyrrolidin-3-yl)-N-phenethyl-benzenesulfonamide | 1.11 | 636.02 |
| 156. | 4-Bromo-N-methyl-N-((R)-1-{2-[3-(2-methyl-quinolin-4-yl)-ureido]-ethyl}-pyrrolidin-3-yl)-benzenesulfonamide | 0.80 | 545.71 |
| 157. | 4-Bromo-N-ethyl-N-((R)-1-{2-[3-(2-methyl-quinolin-4-yl)-ureido]-ethyl}-pyrrolidin-3-yl)-benzenesulfonamide | 0.79 | 559.97 |
| 158. | 4-Bromo-N-ethyl-N-((S)-1-{2-[3-(2-methyl-quinolin-4-yl)-ureido]-ethyl}-pyrrolidin-3-yl)-benzenesulfonamide | 0.84 | 560.02 |
| 159. | 4-Bromo-N-methyl-N-((S)-1-{2-[3-(2-methyl-quinolin-4-yl)-ureido]-ethyl}-pyrrolidin-3-yl)-benzenesulfonamide | 0.80 | 546.00 |
| 160. | N-Ethyl-3-methyl-N-(1-{2-[3-(2-methyl-quinolin-4-yl)-ureido]-ethyl}-piperidin-4-yl)-benzenesulfonamide | 0.98 | 510.40 |
| 161. | N-Ethyl-4-methyl-N-(1-{2-[3-(2-methyl-quinolin-4-yl)-ureido]-ethyl}-piperidin-4-yl)-benzenesulfonamide | 0.97 | 510.40 |
| 162. | N-Ethyl-2-methyl-N-(1-{2-[3-(2-methyl-quinolin-4-yl)-ureido]-ethyl}-piperidin-4-yl)-benzenesulfonamide | 0.97 | 510.40 |
| 163. | 3-Chloro-N-ethyl-N-(1-{2-[3-(2-methyl-quinolin-4-yl)-ureido]-ethyl}-piperidin-4-yl)-benzenesulfonamide | 1.00 | 530.36 |
| 164. | 2-Chloro-N-ethyl-N-(1-{2-[3-(2-methyl-quinolin-4-yl)-ureido]-ethyl}-piperidin-4-yl)-benzenesulfonamide | 0.97 | 530.36 |

-continued

| Example | | $t_r$ | MS (ES+) |
|---|---|---|---|
| 165. | 4-Chloro-N-ethyl-N-(1-{2-[3-(2-methyl-quinolin-4-yl)-ureido]-ethyl}-piperidin-4-yl)-benzenesulfonamide | 1.00 | 530.36 |
| 166. | N-Ethyl-4-fluoro-N-(1-{2-[3-(2-methyl-quinolin-4-yl)-ureido]-ethyl}-piperidin-4-yl)-benzenesulfonamide | 0.95 | 514.38 |
| 167. | N-Ethyl-4-methoxy-N-(1-{2-[3-(2-methyl-quinolin-4-yl)-ureido]-ethyl}-piperidin-4-yl)-benzenesulfonamide | 0.95 | 526.41 |
| 168. | 3,4-Dichloro-N-ethyl-N-(1-{2-[3-(2-methyl-quinolin-4-yl)-ureido]-ethyl}-piperidin-4-yl)-benzenesulfonamide | 1.08 | 564.30 |
| 169. | N-Ethyl-N-(1-{2-[3-(2-methyl-quinolin-4-yl)-ureido]-ethyl}-piperidin-4-yl)-4-trifluoromethyl-benzenesulfonamide | 1.07 | 564.36 |

Example 170

1-{2-[3-(3-Biphenyl-2-yl-1-methyl-ureido)-pyrrolidin-1-yl]-ethyl}-3-(2-methyl-quinolin-4-yl)-urea 170A. Methyl-(1-{2-[3-(2-methyl-quinolin-4-yl)-ureido]-ethyl}-pyrrolidin-3-yl)-carbamic acid tert-butyl ester A mixture of methyl-pyrrolidin-3-yl-carbamic acid tert-butyl ester (10 mmol), 1-(2-chloro-ethyl)-3-(2-methyl-quinolin-4-yl)-urea (10 mmol), NaHCO₃ (20 mmol), NaI (0.5 mmol), and THF (70 mL) is stirred in a sealed vessel at 70° C. for 6 d. The reaction mixture is filtered, evaporated to dryness, and the residue is purified by preparative HPLC to provide the title compound.

170B. 1-[2-(3-Methylamino-pyrrolidin-1-yl)-ethyl]-3-(2-methyl-quinolin-4-yl)-urea

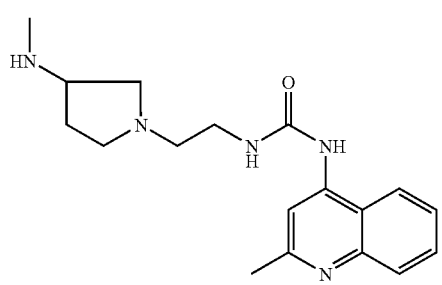

A solution of methyl-(1-{2-[3-(2-methyl-quinolin-4-yl)-ureido]-ethyl}-pyrrolidin-3-yl)-carbamic acid tert-butyl ester (2.35 g, 5.5 mmol) in AcOH (35 mL) is treated with conc. HCl (3.5 mL). After 30 min, the reaction mixture is frozen and lyophylized to provide the title compound as the dihydrochloride salt.

170C. 1-{2-[3-(3-Biphenyl-2-yl-1-methyl-ureido)-pyrrolidin-1-yl]-ethyl}-3-(2-methyl-quinolin-4-yl)-urea

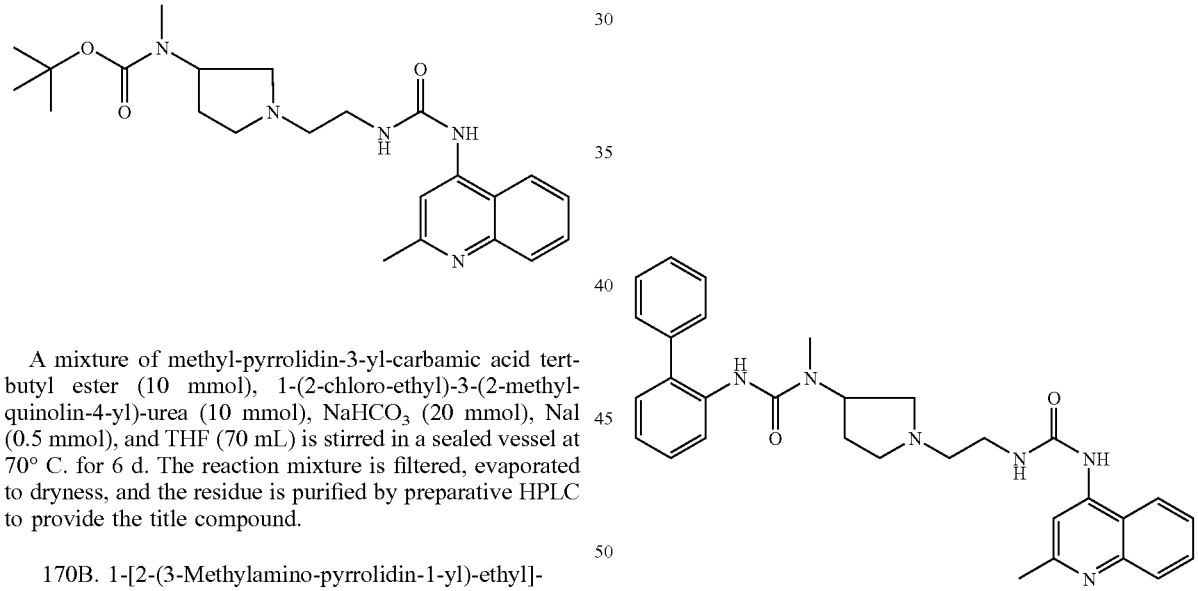

To a solution of 1-[2-(3-methylamino-pyrrolidin-1-yl)-ethyl]-3-(2-methyl-quinolin-4-yl)-urea (0.03 mmol) in THF (0.3 mL) is added a solution of 2-biphenyl isocyanate (0.09 mmol) in THF (0.6 mL). The reaction is allowed to stir for 18 h, and then is quenched with water (0.1 mL), and stirred for an additional 0.5 h. The reaction mixture is evaporated. The residue is taken up in a mixture of formic acid/TFA (1:1; 1 mL), and purified by preparative HPLC.

The following compounds are prepared analogously:

| | Example | $t_r$ | MS (ES+) |
|---|---|---|---|
| 170. | 1-{2-[3-(3-Biphenyl-2-yl-1-methyl-ureido)-pyrrolidin-1-yl]-ethyl}-3-(2-methyl-quinolin-4-yl)-urea | 0.93 | 523.3 |
| 171. | 1-(2-Methyl-quinolin-4-yl)-3-{2-[4-(3-p-tolyl-ureido)-piperidin-1-yl]-ethyl}-urea | 0.91 | 461.2 |
| 172. | 1-(2-Methyl-quinolin-4-yl)-3-{2-[3-(3-p-tolyl-ureido)-pyrrolidin-1-yl]-ethyl}-urea | 0.82 | 447.2 |
| 173. | 1-(2-Methyl-quinolin-4-yl)-3-{2-[3-(1-methyl-3-p-tolyl-ureido)-pyrrolidin-1-yl]-ethyl}-urea | 0.82 | 461.2 |
| 174. | 1-{2-[4-(3-Biphenyl-2-yl-ureido)-piperidin-1-yl]-ethyl}-3-(2-methyl-quinolin-4-yl)-urea | 1.03 | 523.3 |
| 175. | 1-{2-[3-(3-Biphenyl-2-yl-ureido)-pyrrolidin-1-yl]-ethyl}-3-(2-methyl-quinolin-4-yl)-urea | 0.97 | 509.2 |
| 176. | 1-(2-Methyl-quinolin-4-yl)-3-(2-{4-[3-(4-phenoxy-phenyl)-ureido]-piperidin-1-yl}-ethyl)-urea | 1.08 | 539.2 |
| 177. | 1-(2-Methyl-quinolin-4-yl)-3-(2-{3-[3-(4-phenoxy-phenyl)-ureido]-pyrrolidin-1-yl}-ethyl)-urea | 1.04 | 525.2 |
| 178. | 1-(2-{3-[1-Methyl-3-(4-phenoxy-phenyl)-ureido]-pyrrolidin-1-yl}-ethyl)-3-(2-methyl-quinolin-4-yl)-urea | 1.03 | 539.3 |
| 179. | 1-(2-{4-[3-(4-Ethyl-phenyl)-ureido]-piperidin-1-yl}-ethyl)-3-(2-methyl-quinolin-4-yl)-urea | 0.98 | 475.3 |
| 180. | 1-(2-{3-[3-(4-Ethyl-phenyl)-ureido]-pyrrolidin-1-yl}-ethyl)-3-(2-methyl-quinolin-4-yl)-urea | 0.91 | 461.3 |
| 181. | 1-(2-{3-[3-(4-Ethyl-phenyl)-1-methyl-ureido]-pyrrolidin-1-yl}-ethyl)-3-(2-methyl-quinolin-4-yl)-urea | 0.92 | 475.3 |
| 182. | 1-{2-[4-(3-Allyl-ureido)-piperidin-1-yl]-ethyl}-3-(2-methyl-quinolin-4-yl)-urea | 0.66 | 411.2 |
| 183. | 1-{2-[3-(3-Allyl-ureido)-pyrrolidin-1-yl]-ethyl}-3-(2-methyl-quinolin-4-yl)-urea | 0.66 | 397.2 |
| 184. | 1-{2-[3-(3-Allyl-1-methyl-ureido)-pyrrolidin-1-yl]-ethyl}-3-(2-methyl-quinolin-4-yl)-urea | 0.69 | 411.2 |
| 185. | 1-{2-[4-(3-Cyclohexyl-ureido)-piperidin-1-yl]-ethyl}-3-(2-methyl-quinolin-4-yl)-urea | 0.84 | 453.2 |
| 186. | 1-{2-[3-(3-Cyclohexyl-ureido)-pyrrolidin-1-yl]-ethyl}-3-(2-methyl-quinolin-4-yl)-urea | 0.83 | 439.2 |
| 187. | 1-{2-[3-(3-Cyclohexyl-1-methyl-ureido)-pyrrolidin-1-yl]-ethyl}-3-(2-methyl-quinolin-4-yl)-urea | 0.84 | 453.3 |
| 188. | 1-(2-Methyl-quinolin-4-yl)-3-{2-[4-(3-m-tolyl-ureido)-piperidin-1-yl]-ethyl}-urea | 0.90 | 461.3 |
| 189. | 1-(2-Methyl-quinolin-4-yl)-3-{2-[3-(3-m-tolyl-ureido)-pyrrolidin-1-yl]-ethyl}-urea | 0.82 | 447.2 |
| 190. | 1-(2-Methyl-quinolin-4-yl)-3-{2-[3-(1-methyl-3-m-tolyl-ureido)-pyrrolidin-1-yl]-ethyl}-urea | 0.83 | 461.2 |
| 191. | 1-(2-{4-[3-(4-Methoxy-phenyl)-ureido]-piperidin-1-yl}-ethyl)-3-(2-methyl-quinolin-4-yl)-urea | 0.81 | 477.3 |
| 192. | 1-(2-{3-[3-(4-Methoxy-phenyl)-ureido]-pyrrolidin-1-yl}-ethyl)-3-(2-methyl-quinolin-4-yl)-urea | 0.76 | 463.2 |
| 193. | 1-(2-{3-[3-(4-Methoxy-phenyl)-1-methyl-ureido]-pyrrolidin-1-yl}-ethyl)-3-(2-methyl-quinolin-4-yl)-urea | 0.76 | 477.2 |
| 194. | 1-(2-{4-[3-(2-Methoxy-phenyl)-ureido]-piperidin-1-yl}-ethyl)-3-(2-methyl-quinolin-4-yl)-urea | 0.87 | 477.3 |
| 195. | 1-(2-{3-[3-(2-Methoxy-phenyl)-ureido]-pyrrolidin-1-yl}-ethyl)-3-(2-methyl-quinolin-4-yl)-urea | 0.81 | 463.2 |
| 196. | 1-(2-{3-[3-(2-Methoxy-phenyl)-1-methyl-ureido]-pyrrolidin-1-yl}-ethyl)-3-(2-methyl-quinolin-4-yl)-urea | 0.82 | 477.2 |
| 197. | 1-{2-[4-(3-Ethyl-ureido)-piperidin-1-yl]-ethyl}-3-(2-methyl-quinolin-4-yl)-urea | 0.64 | 399.2 |
| 198. | 1-{2-[3-(3-Ethyl-ureido)-pyrrolidin-1-yl]-ethyl}-3-(2-methyl-quinolin-4-yl)-urea | 0.63 | 385.2 |
| 199. | 1-{2-[3-(3-Ethyl-1-methyl-ureido)-pyrrolidin-1-yl]-ethyl}-3-(2-methyl-quinolin-4-yl)-urea | 0.66 | 399.2 |
| 200. | 1-(2-Methyl-quinolin-4-yl)-3-{2-[4-(3-o-tolyl-ureido)-piperidin-1-yl]-ethyl}-urea | 0.83 | 461.2 |
| 201. | 1-(2-Methyl-quinolin-4-yl)-3-{2-[3-(3-o-tolyl-ureido)-pyrrolidin-1-yl]-ethyl}-urea | 0.81 | 447.2 |
| 202. | 1-(2-Methyl-quinolin-4-yl)-3-{2-[3-(1-methyl-3-o-tolyl-ureido)-pyrrolidin-1-yl]-ethyl}-urea | 0.79 | 461.2 |
| 203. | 1-(2-{4-[3-(3-Chloro-phenyl)-ureido]-piperidin-1-yl}-ethyl)-3-(2-methyl-quinolin-4-yl)-urea | 0.97 | 481.2 |
| 204. | 1-(2-{3-[3-(3-Chloro-phenyl)-ureido]-pyrrolidin-1-yl}-ethyl)-3-(2-methyl-quinolin-4-yl)-urea | 0.87 | 467.2 |
| 205. | 1-(2-{3-[3-(3-Chloro-phenyl)-1-methyl-ureido]-pyrrolidin-1-yl}-ethyl)-3-(2-methyl-quinolin-4-yl)-urea | 0.87 | 481.2 |
| 206. | 1-(2-Methyl-quinolin-4-yl)-3-{2-[4-(3-naphthalen-2-yl-ureido)-piperidin-1-yl]-ethyl}-urea | 1.02 | 497.3 |

-continued

|   | Example | $t_r$ | MS (ES+) |
|---|---|---|---|
| 207. | 1-(2-Methyl-quinolin-4-yl)-3-{2-[3-(3-naphthalen-2-yl-ureido)-pyrrolidin-1-yl]-ethyl}-urea | 0.89 | 483.2 |
| 208. | 1-{2-[3-(1-Methyl-3-naphthalen-2-yl-ureido)-pyrrolidin-1-yl]-ethyl}-3-(2-methyl-quinolin-4-yl)-urea | 0.89 | 497.2 |
| 209. | 1-(2-{4-[3-(2,4-Difluoro-phenyl)-ureido]-piperidin-1-yl}-ethyl)-3-(2-methyl-quinolin-4-yl)-urea | 0.87 | 483.2 |
| 210. | 1-(2-{3-[3-(2,4-Difluoro-phenyl)-ureido]-pyrrolidin-1-yl}-ethyl)-3-(2-methyl-quinolin-4-yl)-urea | 0.81 | 469.2 |
| 211. | 1-(2-{3-[3-(2,4-Difluoro-phenyl)-1-methyl-ureido]-pyrrolidin-1-yl}-ethyl)-3-(2-methyl-quinolin-4-yl)-urea | 0.79 | 483.2 |
| 212. | 1-{2-[4-(3-Butyl-ureido)-piperidin-1-yl]-ethyl}-3-(2-methyl-quinolin-4-yl)-urea | 0.76 | 427.3 |
| 213. | 1-{2-[3-(3-Butyl-ureido)-pyrrolidin-1-yl]-ethyl}-3-(2-methyl-quinolin-4-yl)-urea | 0.75 | 413.2 |
| 214. | 1-{2-[3-(3-Butyl-1-methyl-ureido)-pyrrolidin-1-yl]-ethyl}-3-(2-methyl-quinolin-4-yl)-urea | 0.78 | 427.2 |
| 215. | 1-{2-[4-(3-Benzyl-ureido)-piperidin-1-yl]-ethyl}-3-(2-methyl-quinolin-4-yl)-urea | 0.82 | 461.2 |
| 216. | 1-{2-[3-(3-Benzyl-ureido)-pyrrolidin-1-yl]-ethyl}-3-(2-methyl-quinolin-4-yl)-urea | 0.80 | 447.2 |
| 217. | 1-{2-[3-(3-Benzyl-1-methyl-ureido)-pyrrolidin-1-yl]-ethyl}-3-(2-methyl-quinolin-4-yl)-urea | 0.79 | 461.2 |
| 218. | 1-(2-{4-[3-(2-Fluoro-phenyl)-ureido]-piperidin-1-yl}-ethyl)-3-(2-methyl-quinolin-4-yl)-urea | 0.85 | 465.2 |
| 219. | 1-(2-{3-[3-(2-Fluoro-phenyl)-ureido]-pyrrolidin-1-yl}-ethyl)-3-(2-methyl-quinolin-4-yl)-urea | 0.79 | 451.2 |
| 220. | 1-(2-{3-[3-(2-Fluoro-phenyl)-1-methyl-ureido]-pyrrolidin-1-yl}-ethyl)-3-(2-methyl-quinolin-4-yl)-urea | 0.76 | 465.2 |
| 221. | 1-(2-{4-[3-(4-Fluoro-phenyl)-ureido]-piperidin-1-yl}-ethyl)-3-(2-methyl-quinolin-4-yl)-urea | 0.87 | 465.2 |
| 222. | 1-(2-{3-[3-(4-Fluoro-phenyl)-ureido]-pyrrolidin-1-yl}-ethyl)-3-(2-methyl-quinolin-4-yl)-urea | 0.80 | 451.2 |
| 223. | 1-(2-{3-[3-(4-Fluoro-phenyl)-1-methyl-ureido]-pyrrolidin-1-yl}-ethyl)-3-(2-methyl-quinolin-4-yl)-urea | 0.80 | 465.2 |
| 224. | 1-(2-{4-[3-(3-Fluoro-phenyl)-ureido]-piperidin-1-yl}-ethyl)-3-(2-methyl-quinolin-4-yl)-urea | 0.90 | 465.2 |
| 225. | 1-(2-{3-[3-(3-Fluoro-phenyl)-ureido]-pyrrolidin-1-yl}-ethyl)-3-(2-methyl-quinolin-4-yl)-urea | 0.81 | 451.1 |
| 226. | 1-(2-{3-[3-(3-Fluoro-phenyl)-1-methyl-ureido]-pyrrolidin-1-yl}-ethyl)-3-(2-methyl-quinolin-4-yl)-urea | 0.81 | 465.2 |
| 227. | 1-(2-{4-[3-(2-Methyl-benzyl)-ureido]-piperidin-1-yl}-ethyl)-3-(2-methyl-quinolin-4-yl)-urea | 0.89 | 475.2 |
| 228. | 1-(2-{3-[3-(2-Methyl-benzyl)-ureido]-pyrrolidin-1-yl}-ethyl)-3-(2-methyl-quinolin-4-yl)-urea | 0.85 | 461.2 |
| 229. | 1-(2-{3-[1-Methyl-3-(2-methyl-benzyl)-ureido]-pyrrolidin-1-yl}-ethyl)-3-(2-methyl-quinolin-4-yl)-urea | 0.85 | 475.2 |
| 230. | 1-(2-Methyl-quinolin-4-yl)-3-{2-[4-(3-phenethyl-ureido)-piperidin-1-yl]-ethyl}-urea | 0.88 | 475.2 |
| 231. | 1-(2-Methyl-quinolin-4-yl)-3-{2-[3-(3-phenethyl-ureido)-pyrrolidin-1-yl]-ethyl}-urea | 0.85 | 461.2 |
| 232. | 1-{2-[3-(1-Methyl-3-phenethyl-ureido)-pyrrolidin-1-yl]-ethyl}-3-(2-methyl-quinolin-4-yl)-urea | 0.86 | 475.2 |
| 233. | 1-(2-{4-[3-(3-Methoxy-phenyl)-ureido]-piperidin-1-yl}-ethyl)-3-(2-methyl-quinolin-4-yl)-urea | 0.86 | 477.3 |
| 234. | 1-(2-{3-[3-(3-Methoxy-phenyl)-ureido]-pyrrolidin-1-yl}-ethyl)-3-(2-methyl-quinolin-4-yl)-urea | 0.77 | 463.2 |
| 235. | 1-(2-{3-[3-(3-Methoxy-phenyl)-1-methyl-ureido]-pyrrolidin-1-yl}-ethyl)-3-(2-methyl-quinolin-4-yl)-urea | 0.78 | 477.2 |
| 236. | 1-(2-{4-[3-(4-Fluoro-benzyl)-ureido]-piperidin-1-yl}-ethyl)-3-(2-methyl-quinolin-4-yl)-urea | 0.87 | 479.2 |
| 237. | 1-(2-{3-[3-(4-Fluoro-benzyl)-ureido]-pyrrolidin-1-yl}-ethyl)-3-(2-methyl-quinolin-4-yl)-urea | 0.82 | 465.2 |
| 238. | 1-(2-{3-[3-(4-Fluoro-benzyl)-1-methyl-ureido]-pyrrolidin-1-yl}-ethyl)-3-(2-methyl-quinolin-4-yl)-urea | 0.82 | 479.2 |
| 239. | 1-(2-{4-[3-(2-Isopropyl-phenyl)-ureido]-piperidin-1-yl}-ethyl)-3-(2-methyl-quinolin-4-yl)-urea | 0.98 | 489.2 |
| 240. | 1-(2-{3-[3-(2-Isopropyl-phenyl)-ureido]-pyrrolidin-1-yl}-ethyl)-3-(2-methyl-quinolin-4-yl)-urea | 0.95 | 475.3 |
| 241. | 1-(2-{3-[3-(2-Isopropyl-phenyl)-1-methyl-ureido]-pyrrolidin-1-yl}-ethyl)-3-(2-methyl-quinolin-4-yl)-urea | 0.93 | 489.3 |
| 242. | 1-(2-{4-[3-(4-Isopropyl-phenyl)-ureido]-piperidin-1-yl}-ethyl)-3-(2-methyl-quinolin-4-yl)-urea | 1.05 | 489.2 |
| 243. | 1-(2-{3-[3-(4-Isopropyl-phenyl)-ureido]-pyrrolidin-1-yl}-ethyl)-3-(2-methyl-quinolin-4-yl)-urea | 1.00 | 475.2 |
| 244. | 1-(2-{3-[3-(4-Isopropyl-phenyl)-1-methyl-ureido]-pyrrolidin-1-yl}-ethyl)-3-(2-methyl-quinolin-4-yl)-urea | 0.99 | 489.3 |

-continued

| Example | | $t_r$ | MS (ES+) |
|---|---|---|---|
| 245. | 1-(2-{4-[3-(4-Bromo-phenyl)-ureido]-piperidin-1-yl}-ethyl)-3-(2-methyl-quinolin-4-yl)-urea | 1.00 | 525.1 |
| 246. | 1-(2-{3-[3-(4-Bromo-phenyl)-ureido]-pyrrolidin-1-yl}-ethyl)-3-(2-methyl-quinolin-4-yl)-urea | 0.89 | 511.1 |
| 247. | 1-(2-{3-[3-(4-Bromo-phenyl)-1-methyl-ureido]-pyrrolidin-1-yl}-ethyl)-3-(2-methyl-quinolin-4-yl)-urea | 0.88 | 525.1 |
| 248. | 1-(2-Methyl-quinolin-4-yl)-3-(2-{4-[3-(2-phenoxy-phenyl)-ureido]-piperidin-1-yl}-ethyl)-urea | 1.07 | 539.2 |
| 249. | 1-(2-Methyl-quinolin-4-yl)-3-(2-{3-[3-(2-phenoxy-phenyl)-ureido]-pyrrolidin-1-yl}-ethyl)-urea | 1.04 | 525.2 |
| 250. | 1-(2-{3-[1-Methyl-3-(2-phenoxy-phenyl)-ureido]-pyrrolidin-1-yl}-ethyl)-3-(2-methyl-quinolin-4-yl)-urea | 1.03 | 539.2 |
| 251. | 1-{2-[4-(3-tert-Butyl-ureido)-piperidin-1-yl]-ethyl}-3-(2-methyl-quinolin-4-yl)-urea | 0.76 | 427.2 |
| 252. | 1-{2-[3-(3-tert-Butyl-ureido)-pyrrolidin-1-yl]-ethyl}-3-(2-methyl-quinolin-4-yl)-urea | 0.75 | 413.2 |
| 253. | 1-{2-[3-(3-tert-Butyl-1-methyl-ureido)-pyrrolidin-1-yl]-ethyl}-3-(2-methyl-quinolin-4-yl)-urea | 0.79 | 427.2 |
| 254. | 1-(2-{4-[3-(4-Chloro-phenyl)-ureido]-piperidin-1-yl}-ethyl)-3-(2-methyl-quinolin-4-yl)-urea | 0.98 | 481.1 |
| 255. | 1-(2-{3-[3-(4-Chloro-phenyl)-ureido]-pyrrolidin-1-yl}-ethyl)-3-(2-methyl-quinolin-4-yl)-urea | 0.87 | 467.2 |
| 256. | 1-(2-{3-[3-(4-Chloro-phenyl)-1-methyl-ureido]-pyrrolidin-1-yl}-ethyl)-3-(2-methyl-quinolin-4-yl)-urea | 0.86 | 481.2 |

Example 257

Pyridine-2-carboxylic acid (1-{2-[3-(2-methyl-quinolin-4-yl)-ureido]-ethyl}-pyrrolidin-3-yl)-amide 257A. (1-{2-[3-(2-Methyl-quinolin-4-yl)-ureido]-ethyl}-pyrrolidin-3-yl)-carbamic acid tert-butyl ester

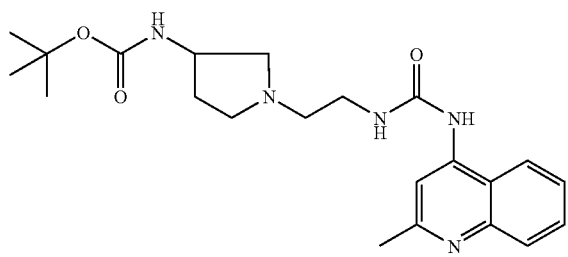

A mixture of pyrrolidin-3-yl-carbamic acid tert-butyl ester (10 mmol), 1-(2-chloro-ethyl)-3-(2-methyl-quinolin-4-yl)-urea (10 mmol), NaHCO$_3$ (20 mmol), NaI (0.5 mmol), and THF (70 mL) is stirred in a sealed vessel at 70° C. for 6 d. The reaction mixture is filtered, evaporated to dryness, and the residue is purified by preparative HPLC to provide the title compound.

257B. 1-[2-(3-Amino-pyrrolidin-1-yl)-ethyl]-3-(2-methyl-quinolin-4-yl)-urea

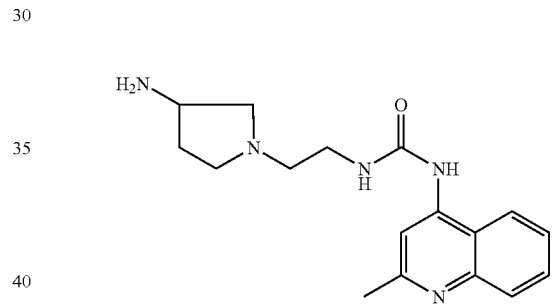

A solution of (1-{2-[3-(2-methyl-quinolin-4-yl)-ureido]-ethyl}-pyrrolidin-3-yl)-carbamic acid tert-butyl ester (5.5 mmol) in AcOH (35 mL) is treated with conc. HCl (3.5 mL). After 30 min, the reaction mixture is frozen and lyophilized to provide the title compound as the dihydrochloride salt.

257C. Pyridine-2-carboxylic acid (1-{2-[3-(2-methyl-quinolin-4-yl)-ureido]-ethyl}-pyrrolidin-3-yl)-amide

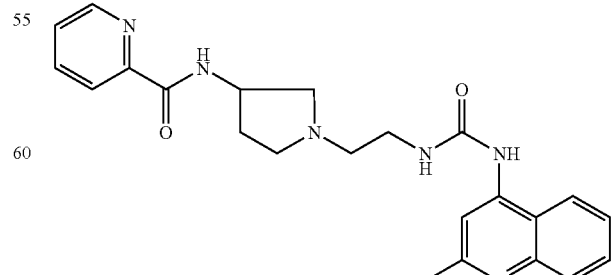

To a solution of 1-[2-(3-amino-pyrrolidin-1-yl)-ethyl]-3-(2-methyl-quinolin-4-yl)-urea (0.03 mmol) in DMF (0.3 mL) is added DIPEA (3 eq). The resulting solution is treated with a solution of pyridine-2-carboxylic acid (1.1 eq) in DMF (0.25 mL). A solution of TBTU (1.1 eq) in DMF (0.25 mL) is added. The reaction is stirred at 20 C for 45 min. The reaction mixture is evaporated to dryness. The residue is taken up in $CH_3CN/H_2O/TFA$ (6:10:1; 1 mL) and is purified by preparative HPLC.

The following compounds are prepared analogously:

| | Example | $t_r$ | MS (ES+) |
|---|---|---|---|
| 257. | Pyridine-2-carboxylic acid (1-{2-[3-(2-methyl-quinolin-4-yl)-ureido]-ethyl}-pyrrolidin-3-yl)-amide | 0.70 | 419.2 |
| 258. | 2-(4-Chloro-phenyl)-N-(1-{2-[3-(2-methyl-quinolin-4-yl)-ureido]-ethyl}-piperidin-4-yl)-acetamide | 0.92 | 480.2 |
| 259. | 2-(4-Chloro-phenyl)-N-(1-{2-[3-(2-methyl-quinolin-4-yl)-ureido]-ethyl}-pyrrolidin-3-yl)-acetamide | 0.91 | 466.2 |
| 260. | 2-(4-Chloro-phenyl)-N-methyl-N-(1-{2-[3-(2-methyl-quinolin-4-yl)-ureido]-ethyl}-pyrrolidin-3-yl)-acetamide | 0.92 | 480.2 |
| 261. | N-(1-{2-[3-(2-Methyl-quinolin-4-yl)-ureido]-ethyl}-piperidin-4-yl)-nicotinamide | 0.62 | 433.2 |
| 262. | N-(1-{2-[3-(2-Methyl-quinolin-4-yl)-ureido]-ethyl}-pyrrolidin-3-yl)-nicotinamide | 0.61 | 419.2 |
| 263. | N-Methyl-N-(1-{2-[3-(2-methyl-quinolin-4-yl)-ureido]-ethyl}-pyrrolidin-3-yl)-nicotinamide | 0.61 | 433.2 |
| 264. | Pyridine-2-carboxylic acid (1-{2-[3-(2-methyl-quinolin-4-yl)-ureido]-ethyl}-piperidin-4-yl)-amide | 0.73 | 433.2 |
| 265. | Pyridine-2-carboxylic acid methyl-(1-{2-[3-(2-methyl-quinolin-4-yl)-ureido]-ethyl}-pyrrolidin-3-yl)-amide | 0.66 | 433.2 |
| 266. | 2-(4-Methoxy-phenyl)-N-(1-{2-[3-(2-methyl-quinolin-4-yl)-ureido]-ethyl}-piperidin-4-yl)-acetamide | 0.82 | 476.2 |
| 267. | 2-(4-Methoxy-phenyl)-N-(1-{2-[3-(2-methyl-quinolin-4-yl)-ureido]-ethyl}-pyrrolidin-3-yl)-acetamide | 0.81 | 462.2 |
| 268. | 2-(4-Methoxy-phenyl)-N-methyl-N-(1-{2-[3-(2-methyl-quinolin-4-yl)-ureido]-ethyl}-pyrrolidin-3-yl)-acetamide | 0.84 | 476.2 |
| 269. | Naphthalene-2-carboxylic acid (1-{2-[3-(2-methyl-quinolin-4-yl)-ureido]-ethyl}-piperidin-4-yl)-amide | 0.98 | 482.2 |
| 270. | Naphthalene-2-carboxylic acid (1-{2-[3-(2-methyl-quinolin-4-yl)-ureido]-ethyl}-pyrrolidin-3-yl)-amide | 0.89 | 468.2 |
| 271. | Naphthalene-2-carboxylic acid methyl-(1-{2-[3-(2-methyl-quinolin-4-yl)-ureido]-ethyl}-pyrrolidin-3-yl)-amide | 0.89 | 482.3 |
| 272. | 2-(4-Isopropyl-phenyl)-N-(1-{2-[3-(2-methyl-quinolin-4-yl)-ureido]-ethyl}-piperidin-4-yl)-acetamide | 1.05 | 488.3 |
| 273. | 2-(4-Isopropyl-phenyl)-N-(1-{2-[3-(2-methyl-quinolin-4-yl)-ureido]-ethyl}-pyrrolidin-3-yl)-acetamide | 1.04 | 474.3 |
| 274. | 2-(4-Isopropyl-phenyl)-N-methyl-N-(1-{2-[3-(2-methyl-quinolin-4-yl)-ureido]-ethyl}-pyrrolidin-3-yl)-acetamide | 1.05 | 488.3 |
| 275. | N-(1-{2-[3-(2-Methyl-quinolin-4-yl)-ureido]-ethyl}-piperidin-4-yl)-2-naphthalen-1-yl-acetamide | 0.98 | 496.2 |
| 276. | N-(1-{2-[3-(2-Methyl-quinolin-4-yl)-ureido]-ethyl}-pyrrolidin-3-yl)-2-naphthalen-1-yl-acetamide | 0.94 | 482.2 |
| 277. | N-Methyl-N-(1-{2-[3-(2-methyl-quinolin-4-yl)-ureido]-ethyl}-pyrrolidin-3-yl)-2-naphthalen-1-yl-acetamide | 0.95 | 496.2 |
| 278. | Cyclopentanecarboxylic acid (1-{2-[3-(2-methyl-quinolin-4-yl)-ureido]-ethyl}-piperidin-4-yl)-amide | 0.77 | 424.2 |
| 279. | Cyclopentanecarboxylic acid (1-{2-[3-(2-methyl-quinolin-4-yl)-ureido]-ethyl}-pyrrolidin-3-yl)-amide | 0.76 | 410.2 |
| 280. | Cyclopentanecarboxylic acid methyl-(1-{2-[3-(2-methyl-quinolin-4-yl)-ureido]-ethyl}-pyrrolidin-3-yl)-amide | 0.82 | 424.2 |
| 281. | N-(1-{2-[3-(2-Methyl-quinolin-4-yl)-ureido]-ethyl}-piperidin-4-yl)-benzamide | 0.78 | 432.2 |
| 282. | N-(1-{2-[3-(2-Methyl-quinolin-4-yl)-ureido]-ethyl}-pyrrolidin-3-yl)-benzamide | 0.76 | 418.2 |
| 283. | N-Methyl-N-(1-{2-[3-(2-methyl-quinolin-4-yl)-ureido]-ethyl}-pyrrolidin-3-yl)-benzamide | 0.77 | 432.2 |
| 284. | N-(1-{2-[3-(2-Methyl-quinolin-4-yl)-ureido]-ethyl}-piperidin-4-yl)-2-o-tolyl-acetamide | 0.87 | 460.2 |
| 285. | N-(1-{2-[3-(2-Methyl-quinolin-4-yl)-ureido]-ethyl}-pyrrolidin-3-yl)-2-o-tolyl-acetamide | 0.85 | 446.2 |
| 286. | N-Methyl-N-(1-{2-[3-(2-methyl-quinolin-4-yl)-ureido]-ethyl}-pyrrolidin-3-yl)-2-o-tolyl-acetamide | 0.87 | 460.3 |
| 287. | 3-(4-Fluoro-phenyl)-N-(1-{2-[3-(2-methyl-quinolin-4-yl)-ureido]-ethyl}-piperidin-4-yl)-propionamide | 0.89 | 478.2 |
| 288. | 3-(4-Fluoro-phenyl)-N-(1-{2-[3-(2-methyl-quinolin-4-yl)-ureido]-ethyl}-pyrrolidin-3-yl)-propionamide | 0.88 | 464.2 |
| 289. | 3-(4-Fluoro-phenyl)-N-methyl-N-(1-{2-[3-(2-methyl-quinolin-4-yl)-ureido]-ethyl}-pyrrolidin-3-yl)-propionamide | 0.91 | 478.2 |

-continued

| | Example | $t_r$ | MS (ES+) |
|---|---|---|---|
| 290. | N-(1-{2-[3-(2-Methyl-quinolin-4-yl)-ureido]-ethyl}-piperidin-4-yl)-isonicotinamide | 0.61 | 433.2 |
| 291. | N-(1-{2-[3-(2-Methyl-quinolin-4-yl)-ureido]-ethyl}-pyrrolidin-3-yl)-isonicotinamide | 0.61 | 419.2 |
| 292. | N-Methyl-N-(1-{2-[3-(2-methyl-quinolin-4-yl)-ureido]-ethyl}-pyrrolidin-3-yl)-isonicotinamide | 0.59 | 433.2 |
| 293. | N-(1-{2-[3-(2-Methyl-quinolin-4-yl)-ureido]-ethyl}-piperidin-4-yl)-3-phenyl-propionamide | 0.86 | 460.3 |
| 294. | N-(1-{2-[3-(2-Methyl-quinolin-4-yl)-ureido]-ethyl}-pyrrolidin-3-yl)-3-phenyl-propionamide | 0.84 | 446.2 |
| 295. | N-Methyl-N-(1-{2-[3-(2-methyl-quinolin-4-yl)-ureido]-ethyl}-pyrrolidin-3-yl)-3-phenyl-propionamide | 0.88 | 460.2 |
| 296. | 2-(4-Fluoro-phenyl)-N-(1-{2-[3-(2-methyl-quinolin-4-yl)-ureido]-ethyl}-piperidin-4-yl)-acetamide | 0.83 | 464.2 |
| 297. | 2-(4-Fluoro-phenyl)-N-(1-{2-[3-(2-methyl-quinolin-4-yl)-ureido]-ethyl}-pyrrolidin-3-yl)-acetamide | 0.82 | 450.2 |
| 298. | 2-(4-Fluoro-phenyl)-N-methyl-N-(1-{2-[3-(2-methyl-quinolin-4-yl)-ureido]-ethyl}-pyrrolidin-3-yl)-acetamide | 0.86 | 464.2 |
| 299. | N-(1-{2-[3-(2-Methyl-quinolin-4-yl)-ureido]-ethyl}-piperidin-4-yl)-3-p-tolyl-propionamide | 0.94 | 474.3 |
| 300. | N-(1-{2-[3-(2-Methyl-quinolin-4-yl)-ureido]-ethyl}-pyrrolidin-3-yl)-3-p-tolyl-propionamide | 0.93 | 460.2 |
| 301. | N-Methyl-N-(1-{2-[3-(2-methyl-quinolin-4-yl)-ureido]-ethyl}-pyrrolidin-3-yl)-3-p-tolyl-propionamide | 0.97 | 474.3 |
| 302. | 3-(2-Methoxy-phenyl)-N-(1-{2-[3-(2-methyl-quinolin-4-yl)-ureido]-ethyl}-piperidin-4-yl)-propionamide | 0.91 | 490.3 |
| 303. | 3-(2-Methoxy-phenyl)-N-(1-{2-[3-(2-methyl-quinolin-4-yl)-ureido]-ethyl}-pyrrolidin-3-yl)-propionamide | 0.88 | 476.3 |
| 304. | 3-(2-Methoxy-phenyl)-N-methyl-N-(1-{2-[3-(2-methyl-quinolin-4-yl)-ureido]-ethyl}-pyrrolidin-3-yl)-propionamide | 0.91 | 490.3 |
| 305. | 3-(4-Methoxy-phenyl)-N-(1-{2-[3-(2-methyl-quinolin-4-yl)-ureido]-ethyl}-piperidin-4-yl)-propionamide | 0.87 | 490.3 |
| 306. | 3-(4-Methoxy-phenyl)-N-(1-{2-[3-(2-methyl-quinolin-4-yl)-ureido]-ethyl}-pyrrolidin-3-yl)-propionamide | 0.86 | 476.3 |
| 307. | 3-(4-Methoxy-phenyl)-N-methyl-N-(1-{2-[3-(2-methyl-quinolin-4-yl)-ureido]-ethyl}-pyrrolidin-3-yl)-propionamide | 0.89 | 490.3 |
| 308. | 3-(3-Methoxy-phenyl)-N-(1-{2-[3-(2-methyl-quinolin-4-yl)-ureido]-ethyl}-piperidin-4-yl)-propionamide | 0.88 | 490.2 |
| 309. | 3-(3-Methoxy-phenyl)-N-(1-{2-[3-(2-methyl-quinolin-4-yl)-ureido]-ethyl}-pyrrolidin-3-yl)-propionamide | 0.87 | 476.2 |
| 310. | 3-(3-Methoxy-phenyl)-N-methyl-N-(1-{2-[3-(2-methyl-quinolin-4-yl)-ureido]-ethyl}-pyrrolidin-3-yl)-propionamide | 0.89 | 490.2 |
| 311. | N-(1-{2-[3-(2-Methyl-quinolin-4-yl)-ureido]-ethyl}-piperidin-4-yl)-2-phenyl-acetamide | 0.80 | 446.2 |
| 312. | N-(1-{2-[3-(2-Methyl-quinolin-4-yl)-ureido]-ethyl}-pyrrolidin-3-yl)-2-phenyl-acetamide | 0.79 | 432.2 |
| 313. | N-Methyl-N-(1-{2-[3-(2-methyl-quinolin-4-yl)-ureido]-ethyl}-pyrrolidin-3-yl)-2-phenyl-acetamide | 0.82 | 446.2 |
| 314. | 4-Fluoro-N-(1-{2-[3-(2-methyl-quinolin-4-yl)-ureido]-ethyl}-piperidin-4-yl)-benzamide | 0.83 | 450.2 |
| 315. | 4-Fluoro-N-(1-{2-[3-(2-methyl-quinolin-4-yl)-ureido]-ethyl}-pyrrolidin-3-yl)-benzamide | 0.80 | 436.2 |
| 316. | 4-Fluoro-N-methyl-N-(1-{2-[3-(2-methyl-quinolin-4-yl)-ureido]-ethyl}-pyrrolidin-3-yl)-benzamide | 0.78 | 450.2 |
| 317. | N-(1-{2-[3-(2-Methyl-quinolin-4-yl)-ureido]-ethyl}-piperidin-4-yl)-2-m-tolyl-acetamide | 0.88 | 460.2 |
| 318. | N-(1-{2-[3-(2-Methyl-quinolin-4-yl)-ureido]-ethyl}-pyrrolidin-3-yl)-2-m-tolyl-acetamide | 0.87 | 446.2 |
| 319. | N-Methyl-N-(1-{2-[3-(2-methyl-quinolin-4-yl)-ureido]-ethyl}-pyrrolidin-3-yl)-2-m-tolyl-acetamide | 0.91 | 460.2 |
| 320. | N-(1-{2-[3-(2-Methyl-quinolin-4-yl)-ureido]-ethyl}-piperidin-4-yl)-2-p-tolyl-acetamide | 0.89 | 460.2 |
| 321. | N-(1-{2-[3-(2-Methyl-quinolin-4-yl)-ureido]-ethyl}-pyrrolidin-3-yl)-2-p-tolyl-acetamide | 0.87 | 446.3 |
| 322. | N-Methyl-N-(1-{2-[3-(2-methyl-quinolin-4-yl)-ureido]-ethyl}-pyrrolidin-3-yl)-2-p-tolyl-acetamide | 0.91 | 460.2 |
| 323. | 3-Chloro-N-(1-{2-[3-(2-methyl-quinolin-4-yl)-ureido]-ethyl}-piperidin-4-yl)-benzamide | 0.91 | 466.1 |
| 324. | 3-Chloro-N-(1-{2-[3-(2-methyl-quinolin-4-yl)-ureido]-ethyl}-pyrrolidin-3-yl)-benzamide | 0.85 | 452.1 |
| 325. | 3-Chloro-N-methyl-N-(1-{2-[3-(2-methyl-quinolin-4-yl)-ureido]-ethyl}-pyrrolidin-3-yl)-benzamide | 0.84 | 466.2 |

|  | Example | $t_r$ | MS (ES+) |
|---|---|---|---|
| 326. | Quinoline-6-carboxylic acid (1-{2-[3-(2-methyl-quinolin-4-yl)-ureido]-ethyl}-piperidin-4-yl)-amide | 0.67 | 483.2 |
| 327. | Quinoline-6-carboxylic acid (1-{2-[3-(2-methyl-quinolin-4-yl)-ureido]-ethyl}-pyrrolidin-3-yl)-amide | 0.66 | 469.2 |
| 328. | Quinoline-6-carboxylic acid methyl-(1-{2-[3-(2-methyl-quinolin-4-yl)-ureido]-ethyl}-pyrrolidin-3-yl)-amide | 0.63 | 483.2 |
| 329. | 4-tert-Butyl-N-(1-{2-[3-(2-methyl-quinolin-4-yl)-ureido]-ethyl}-piperidin-4-yl)-benzamide | 1.06 | 488.3 |
| 330. | 4-tert-Butyl-N-(1-{2-[3-(2-methyl-quinolin-4-yl)-ureido]-ethyl}-pyrrolidin-3-yl)-benzamide | 1.04 | 474.2 |
| 331. | 4-tert-Butyl-N-methyl-N-(1-{2-[3-(2-methyl-quinolin-4-yl)-ureido]-ethyl}-pyrrolidin-3-yl)-benzamide | 1.05 | 488.3 |
| 332. | 2-(4-Dimethylamino-phenyl)-N-(1-{2-[3-(2-methyl-quinolin-4-yl)-ureido]-ethyl}-piperidin-4-yl)-acetamide | 0.64 | 489.3 |
| 333. | 2-(4-Dimethylamino-phenyl)-N-(1-{2-[3-(2-methyl-quinolin-4-yl)-ureido]-ethyl}-pyrrolidin-3-yl)-acetamide | 0.62 | 475.2 |
| 334. | 2-(4-Dimethylamino-phenyl)-N-methyl-N-(1-{2-[3-(2-methyl-quinolin-4-yl)-ureido]-ethyl}-pyrrolidin-3-yl)-acetamide | 0.65 | 489.3 |
| 335. | 2,4-Dimethoxy-N-(1-{2-[3-(2-methyl-quinolin-4-yl)-ureido]-ethyl}-piperidin-4-yl)-benzamide | 0.89 | 492.2 |
| 336. | 2,4-Dimethoxy-N-(1-{2-[3-(2-methyl-quinolin-4-yl)-ureido]-ethyl}-pyrrolidin-3-yl)-benzamide | 0.83 | 478.2 |
| 337. | 2,4-Dimethoxy-N-methyl-N-(1-{2-[3-(2-methyl-quinolin-4-yl)-ureido]-ethyl}-pyrrolidin-3-yl)-benzamide | 0.81 | 492.2 |
| 338. | N-(1-{2-[3-(2-Methyl-quinolin-4-yl)-ureido]-ethyl}-piperidin-4-yl)-4-pyrrol-1-yl-benzamide | 1.00 | 497.2 |
| 339. | N-(1-{2-[3-(2-Methyl-quinolin-4-yl)-ureido]-ethyl}-pyrrolidin-3-yl)-4-pyrrol-1-yl-benzamide | 0.95 | 483.2 |
| 340. | N-Methyl-N-(1-{2-[3-(2-methyl-quinolin-4-yl)-ureido]-ethyl}-pyrrolidin-3-yl)-4-pyrrol-1-yl-benzamide | 0.95 | 497.2 |
| 341. | 2-(4-Bromo-phenyl)-N-(1-{2-[3-(2-methyl-quinolin-4-yl)-ureido]-ethyl}-piperidin-4-yl)-acetamide | 0.95 | 524.1 |
| 342. | 2-(4-Bromo-phenyl)-N-(1-{2-[3-(2-methyl-quinolin-4-yl)-ureido]-ethyl}-pyrrolidin-3-yl)-acetamide | 0.93 | 510.1 |
| 343. | 2-(4-Bromo-phenyl)-N-methyl-N-(1-{2-[3-(2-methyl-quinolin-4-yl)-ureido]-ethyl}-pyrrolidin-3-yl)-acetamide | 0.94 | 524.1 |
| 344. | 4-Benzoyl-N-(1-{2-[3-(2-methyl-quinolin-4-yl)-ureido]-ethyl}-piperidin-4-yl)-benzamide | 1.03 | 536.2 |
| 345. | 4-Benzoyl-N-(1-{2-[3-(2-methyl-quinolin-4-yl)-ureido]-ethyl}-pyrrolidin-3-yl)-benzamide | 0.99 | 522.2 |
| 346. | 4-Benzoyl-N-methyl-N-(1-{2-[3-(2-methyl-quinolin-4-yl)-ureido]-ethyl}-pyrrolidin-3-yl)-benzamide | 0.98 | 536.2 |
| 347. | N-(1-{2-[3-(2-Methyl-quinolin-4-yl)-ureido]-ethyl}-piperidin-4-yl)-acetamide | 0.60 | 370.2 |
| 348. | N-(1-{2-[3-(2-Methyl-quinolin-4-yl)-ureido]-ethyl}-pyrrolidin-3-yl)-acetamide | 0.59 | 356.2 |
| 349. | N-Methyl-N-(1-{2-[3-(2-methyl-quinolin-4-yl)-ureido]-ethyl}-pyrrolidin-3-yl)-acetamide | 0.62 | 370.2 |
| 350. | 4-Methoxy-cyclohexanecarboxylic acid (1-{2-[3-(2-methyl-quinolin-4-yl)-ureido]-ethyl}-piperidin-4-yl)-amide | 0.74 | 468.3 |
| 351. | 4-Methoxy-cyclohexanecarboxylic acid (1-{2-[3-(2-methyl-quinolin-4-yl)-ureido]-ethyl}-piperidin-4-yl)-amide | 0.75 | 468.3 |
| 352. | 1-[2-(4-Benzyl-piperidin-1-yl)-ethyl]-3-(2-methyl-quinolin-4-yl)-urea | 0.7 | 403.3 |
| 353. | 4-Methoxy-cyclohexanecarboxylic acid (1-{2-[3-(2-methyl-quinolin-4-yl)-ureido]-ethyl}-pyrrolidin-3-yl)-amide | 0.72 | 454.2 |
| 354. | 4-Methoxy-cyclohexanecarboxylic acid (1-{2-[3-(2-methyl-quinolin-4-yl)-ureido]-ethyl}-pyrrolidin-3-yl)-amide | 0.75 | 454.2 |
| 355. | 4-Methoxy-cyclohexanecarboxylic acid methyl-(1-{2-[3-(2-methyl-quinolin-4-yl)-ureido]-ethyl}-pyrrolidin-3-yl)-amide | 0.73 | 468.2 |
| 356. | 4-Methoxy-cyclohexanecarboxylic acid methyl-(1-{2-[3-(2-methyl-quinolin-4-yl)-ureido]-ethyl}-pyrrolidin-3-yl)-amide | 0.78 | 468.3 |

Example 357

1-[2-(4-Phenoxy-piperidin-1-yl)-ethyl]-3-quinolin-4-yl-urea

357A. 1-(2-Chloroethyl)-3-quinolin-4-yl-urea

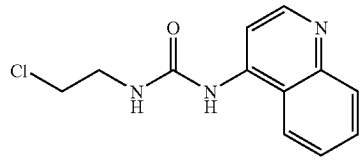

To a solution of 4-aminoquinoline (3.46 g, 24 mmol) in dry THF is added chloroethylisocyanate (3.1 mL, 36 mmol). The reaction mixture is stirred for 18 h. MeOH (10 mL) is added, and stirring is continued for an additional hour. The reaction mixture is evaporated, and partitioned between DCM and aqueous 5% citric acid (150 mL). The aqueous layer is carefully adjusted to pH 9 with solid $NaHCO_3$. The precipitate is filtered, washed with $H_2O$ (5×20 mL) and $Et_2O$ (2×20 mL), and dried in vacuo at 45° C. to provide the title compound.

357B. 1-Benzyl-4-phenoxy-piperidine

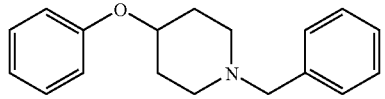

To a cold (0° C.) mixture of phenol (190 mg, 2.02 mmol) and triphenylphosphine (680 mg, 2.6 mmol) in dry THF (6.4 mL) is added dropwise over 30 min a solution of 1-benzyl-piperidin-4-ol (490 mg, 2.6 mmol) and diethylazadicarboxylate (0.41 mL, 2.6 mmol) in dry THF (4.8 mL). The mixture is stirred at room temperature under nitrogen for 20 h. The mixture is dissolved in EtOAc, washed with sat. $NaHCO_3$ (2×20 mL), dried ($MgSO_4$), filtered and concentrated to provide a crude oil. Flash chromatography (EtOAc/Hex: 3/7) provides the title compound.

357C. 4-Phenoxy-piperidine

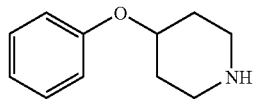

A mixture of 1-benzyl-4-phenoxy-piperidine (420 mg, 1.6 mmol), Pd—C 10% (10 mg) and TFA (0.18 mL, 1,6 mmol) in MeOH (5 mL) is hydrogenated at room temperature and atmospheric pressure for 20 h. The mixture is filtered over Celite and the filtrate is concentrated under reduced pressure. The residue is dissolved in $CH_2Cl_2$, washed with sat. $NaHCO_3$, filtered and concentrated to provide the title compound.

357D. 1-[2-(4-Phenoxy-piperidin-1-yl)-ethyl]-3-quinolin-4-yl-urea

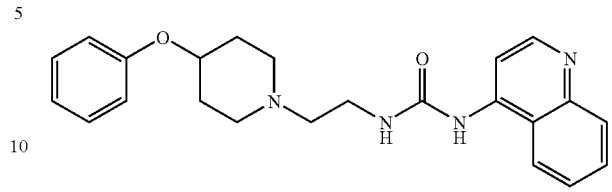

To a solution of 4-phenoxy-piperidine (0.03 mmol) in dry THF (1 mL) is added 1-(2-chloro-ethyl)-3-quinolin-4-yl-urea (0.03 mmol), solid $NaHCO_3$ (2.5 mg), and NaI (1 mg). The flask is tightly sealed, and shaken at 70° C. for 6 days. The reaction mixture is evaporated, taken up in aqueous formic acid, and purified by preparative HPLC to provide the title compound.

The following compounds are prepared in an analogous fashion. Values in parentheses are obtained by analytical Method B as described in the Experimental Section above.

| Example | | $t_r$ | MS (ES+) |
|---|---|---|---|
| 357. | 1-[2-(4-Phenoxy-piperidin-1-yl)-ethyl]-3-quinolin-4-yl-urea | (2.58) | 391 |
| 358. | 1-{2-[4-(2-Methoxy-phenoxy)-piperidin-1-yl]-ethyl}-3-quinolin-4-yl-urea | (2.66) | 421 |
| 359. | 1-Quinolin-4-yl-3-[2-(4-o-tolyloxy-piperidin-1-yl)-ethyl]-urea | (3.68) | 405 |
| 360. | 1-{2-[4-(2-Methoxy-phenoxy)-piperidin-1-yl]-ethyl}-3-(2-methyl-quinolin-4-yl)-urea | (2.70) | 435 |
| 361. | 1-(2-Methyl-quinolin-4-yl)-3-[2-(4-phenoxy-piperidin-1-yl)-ethyl]-urea | (2.58) | 405 |
| 362. | 1-(2-Methyl-quinolin-4-yl)-3-[2-(4-o-tolyloxy-piperidin-1-yl)-ethyl]-urea | (3.65) | 419 |

Example 363

1-{2-[4-(2-Methoxy-phenyl)-piperidin-1-yl]-ethyl}-3-(2-methyl-quinolin-4-y)-urea

363A. 4-Trifluoromethanesulfonyl-3,6-dihydro-2H-pyridine-1-carboxylic acid tert-butyl ester

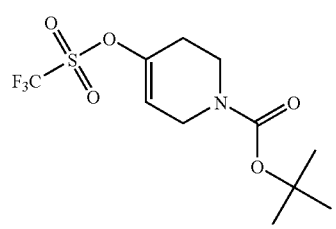

To a cooled (−78° C.) solution of LDA (2.76 mL, 5.52 mmol) in anhydrous THF (6 mL), is added dropwise a solution of 4-oxo-piperidine-1-carboxylic acid tert-butyl ester (1 g, 5.02 mmol) in anhydrous THF (6 mL). After stirring at −78° C. for 20 min, a solution of N-phenyltrifluoromethanesulfonimide (1.91 g, 5.34 mmol) in anhydrous THF (6 mL) is added dropwise. The mixture is stirred at 0°

C. for 3 h and then concentrated in vacuo. The resulting oil is dissolved in CH₂Cl₂ (3 mL) and loaded onto a pad of neutral alumina and eluted with (Hex/EtOAc, 9/1) to provide the title compound.

363B. 4-(2-Methoxy-phenyl)-3,6-dihydro-2H-pyridine-1-carboxylic acid tert-butyl ester

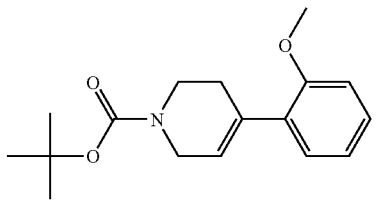

A three necked flask purged with nitrogen is charged with aqueous 2N Na₂CO₃ (1.4 mL), 1,2-dimethoxyethane (3.7 mL), 2-methoxyphenyl boronic acid (206 mg, 1.35 mmol), anhydrous lithium chloride (123 mg, 2.9 mmol), 4-trifluoromethanesulfonyl-3,6-dihydro-2H-pyridine-1-carboxylic acid tert-butyl ester (321 mg, 0.96 mmol) and tetrakis(triphenylphosphine)palladium (56 mg, 0.048 mmol). The mixture is stirred at reflux for 2 h under nitrogen, cooled and concentrated under reduced pressure. The residue is partitioned between CH₂Cl₂ (10 mL), aqueous 2N Na₂CO₃ (10 mL), and concentrated NH₄OH (1 mL). The aqueous layer is extracted twice with CH₂Cl₂. The combined organic layers are dried (MgSO₄), filtered and concentrated to provide a crude oil. Flash chromatography (Hex/AcOEt/CH₂Cl₂: 5/1/1) provides the title compound.

363C. 4-(2-Methoxy-phenyl)-piperidine-1-carboxylic acid tert-butyl ester

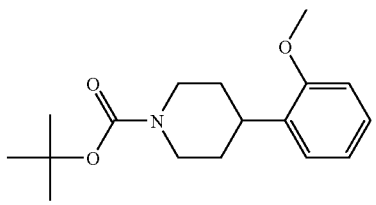

A mixture of 4-(2-methoxy-phenyl)-3,6-dihydro-2H-pyridine-1-carboxylic acid tert-butyl ester (200 mg, 0.69 mmol), Pd—C 10% (30 mg) in EtOAc (5 mL) is hydrogenated at room temperature and atmospheric pressure for 20 h. The mixture is filtered over Celite, and the filtrate is evaporated to provide the title compound.

363D. 4-(2-Methoxy-phenyl)-piperidine

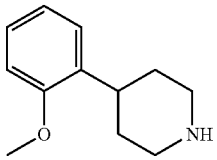

A mixture of 4-(2-methoxy-phenyl)-piperidine-1-carboxylic acid tert-butyl ester (190 mg, 0.65 mmol), and TFA (0.35 mL, 4.8 mmol) in dry CH₂Cl₂ (5 mL) is stirred at room temperature under nitrogen for 2 h. The mixture is concentrated under reduced pressure, and the residue is combined with CH₂Cl₂/sat. aqueous NaHCO₃. The aqueous layer is extracted twice with CH₂Cl₂, the combined organic extracts are washed with brine, dried (MgSO₄), filtered and concentrated to provide the title compound.

363E. 1-{2-[4-(2-Methoxy-phenyl)-piperidin-1-yl]-ethyl}3-(2-methyl-quinolin-4-yl)-urea

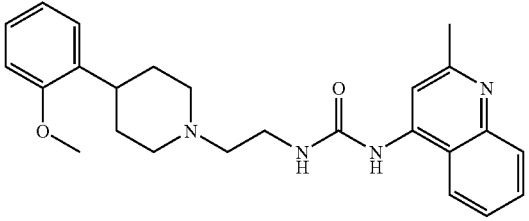

To a solution of 4-(2-methoxy-phenyl)-piperidine (0.03 mmol) in dry THF (1 mL) is added 1-(2-chloro-ethyl)-3-quinolin-4-yl-urea (0.03 mmol), solid NaHCO₃ (2.5 mg), and NaI (1 mg). The flask is tightly sealed, and shaken at 70° C. for 6 days. The reaction mixture is evaporated, taken up in aqueous formic acid, and purified by preparative HPLC to provide the title compound.

The following compounds are prepared in an analogous fashion. Values in parentheses are obtained by analytical Method B as described in the Experimental Section above.

| Example | | $t_r$ | MS (ES+) |
|---|---|---|---|
| 363. | 1-{2-[4-(2-Methoxy-phenyl)-piperidin-1-yl]-ethyl}-3-(2-methyl-quinolin-4-yl)-urea | (3.68) | 419 |
| 364. | 1-[2-(4-Phenyl-piperidin-1-yl)-ethyl]-3-quinolin-4-yl-urea | (3.49) | 375 |
| 365. | 1-(2-Methyl-quinolin-4-yl)-3-[2-(4-phenyl-piperidin-1-yl)-ethyl]-urea | (3.56) | 389 |
| 366. | 1-Quinolin-4-yl-3-[2-(4-o-tolyl-piperidin-1-yl)-ethyl]-urea | (3.63) | 389 |
| 367. | 1-(2-Methyl-quinolin-4-yl)-3-[2-(4-o-tolyl-piperidin-1-yl)-ethyl]-urea | (3.72) | 403 |

Example 368

1-[2-(4-Hydroxy-4-p-tolyl-piperidin-1-yl)-ethyl]-3-(2-methyl-quinolin-4-yl)-urea

368A. 1-Benzyl-4-p-tolyl-piperidin-4-ol

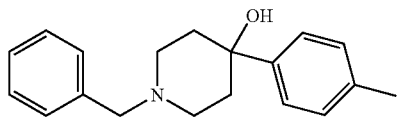

A solution of 4-bromotoluene (1.017 g, 5.94 mmol) in anhydrous Et₂O (6 mL), is added dropwise to a mixture of Mg (0.159 g, 6.54 mmol) and a catalytic amount of I₂ (0.015 g, 0.26 mmol) in anhydrous Et₂O (10 mL). The mixture is stirred at reflux for 5 h under nitrogen. To this cloudy solution is added dropwise at 0° C., a solution of N-benzyl-4-piperidone (1.063 mL, 5.94 mmol) in anhydrous Et₂O (6 mL) and the mixture is stirred at reflux for 1.5 h. After cooling, the mixture is poured into sat. NH₄Cl (20 mL) and extracted with EtOAc (3×30 mL). The combined organic extracts are washed with brine, dried (MgSO₄), filtered and concentrated to provide a crude oil. Flash chromatography (EtOAc/Hex: 3/7) affords the title compound.

368B. 4-p-Tolyl-piperidin-4-ol

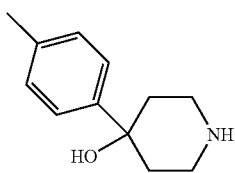

A mixture of 1-benzyl-4-p-tolyl-piperidin-4-ol (350 mg, 1.243 mmol), and Pd—C 10% (55 mg) in EtOAc (7 mL) is hydrogenated at room temperature and atmospheric pressure for 20 h. The mixture is filtered over Celite, and the filtrate is evaporated to provide the title compound.

368C. 1-[2-(4-Hydroxy-4-p-tolyl-piperidin-1-yl)-ethyl]-3-(2-methyl-quinolin-4-yl)-urea

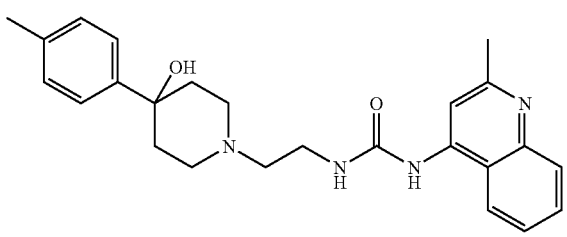

To a solution of 4-p-tolyl-piperidin-4-ol (0.03 mmol) in dry THF (1 mL) is added 1-(2-chloro-ethyl)-3-(2-methyl-quinolin-4-yl)-urea (0.03 mmol), solid NaHCO₃ (2.5 mg), and NaI (1 mg). The flask is tightly sealed, and shaken at 70° C. for 6 days. The reaction mixture is evaporated, taken up in aqueous formic acid, and purified by preparative HPLC to provide the title compound.

| Example | | $t_r$ | MS (ES+) |
|---|---|---|---|
| 368. | 1-[2-(4-Hydroxy-4-p-tolyl-piperidin-1-yl)-ethyl]-3-(2-methyl-quinolin-4-yl)-urea | 0.95 | 419.5 |

Example 369

1-[2-(4-Benzyl-4-hydroxy-piperidin-1-yl)-ethyl]-3-(2-methyl-quinolin-4-yl)-urea

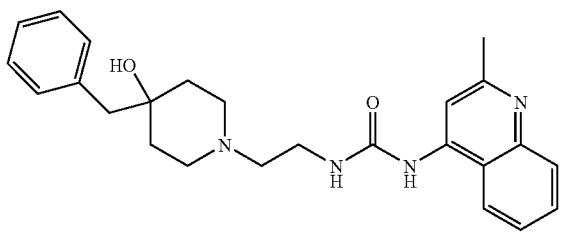

To a solution of 4-hydroxy-4-benzyl-piperidine (380.6 mg, 2 mmol) in dry THF (10 mL) is added 1-(2-chloro-ethyl)-3-(2-methyl-quinolin-4-yl)-urea (263.7 mg, 1 mmol) and solid NaHCO₃ (672 mg, 8 mmol). The reaction mixture is stirred at 45° C. for 6 days. The reaction mixture is diluted with CH₂Cl₂ (100 mL) and washed with sat. Na₂CO₃ (2×30 mL). The aqueous phase is re-extracted with CH₂Cl₂ (2×25 mL), the combined organic phases are washed with brine (20 mL), dried (Na₂SO₄), filtered and evaporated. The residue is purified by preparative HPLC to provide the title compound.

The following compounds are prepared in an analogous fashion. Values in parentheses are obtained by analytical Method B as described in the Experimental Section above.

| Example | | $t_r$ | MS (ES+) |
|---|---|---|---|
| 369. | 1-[2-(4-Benzyl-4-hydroxy-piperidin-1-yl)-ethyl]-3-(2-methyl-quinolin-4-yl)-urea | 0.89 | 419.2 |
| 370. | 1-[2-(4-Hydroxy-4-phenyl-piperidin-1-yl)-ethyl]-3-(2-methyl-quinolin-4-yl)-urea | 1.09 | 405.2 |
| 371. | 1-{2-[4-(4-Chloro-phenyl)-4-hydroxy-piperidin-1-yl]-ethyl}-3-quinolin-4-yl-urea | (2.54) | 425 |
| 372. | 1-{2-[4-(4-Chloro-phenyl)-4-hydroxy-piperidin-1-yl]-ethyl}-3-(2-methyl-quinolin-4-yl)-urea | (2.79) | 439 |
| 373. | 1-{2-[4-(4-Bromo-phenyl)-4-hydroxy-piperidin-1-yl]-ethyl}-3-quinolin-4-yl-urea | (2.68) | 470 |
| 374. | 1-{2-[4-(4-Bromo-phenyl)-4-hydroxy-piperidin-1-yl]-ethyl}-3-(2-methyl-quinolin-4-yl)-urea | (2.58) | 484 |
| 375. | 1-[2-(4-Benzyl-piperidin-1-yl)-ethyl]-3-quinolin-4-yl-urea | 1.02 | 389.2 |
| 376. | 1-[2-(4-Benzyl-piperidin-1-yl)-ethyl]-3-(2-methyl-quinolin-4-yl)-urea | 0.7 | 403.3 |
| 377. | 1-[2-(4-Benzyl-4-hydroxy-piperidin-1-yl)-ethyl]-3-quinolin-4-yl-urea | 0.87 | 405.2 |
| 378. | 1-{2-[4-(Hydroxy-diphenyl-methyl)-piperidin-1-yl]-ethyl}-3-quinolin-4-yl-urea | 1.02 | 481.6 |
| 379. | 1-[2-(4-Benzoyl-piperidin-1-yl)-ethyl]-3-quinolin-4-yl-urea | (2.73) | 401.6 |

| Example | | $t_r$ | MS (ES+) |
|---|---|---|---|
| 380. | 1-[2-(4-Benzoyl-piperidin-1-yl)-ethyl]-3-(2-methyl-quinolin-4-yl)-urea | (3.44) | 417.3 |

Example 381

3-[2-(4-Benzyl-piperidin-1-yl)-ethyl]-1-methyl-1-(2-methyl-quinolin-4-yl)-urea 381A. (2-Bromo-ethyl)-carbamic acid tert-butyl ester

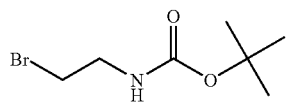

To 1 N aqueous NaOH (200 mL) is added MeOH (400 mL) and the resulting solution is cooled to 20° C. 2-Bromoethylamine hydrobromide (25.0 g, 122 mmol) is added in a single portion, followed by di-tert-butyl dicarbonate (26.6 g, 122 mmol). The reaction mixture is stirred for 2.5 h. The MeOH is removed on a rotary evaporator, and the aqueous suspension is extracted with $CH_2Cl_2$ (2×175 mL). The combined organic extracts are extracted with 5% aqueous citric acid (300 mL), dried ($MgSO_4$), filtered, and evaporated to provide the title compound.

381B. [2-(4-Benzyl-piperidin-1-yl)-ethyl]-carbamic acid tert-butyl ester

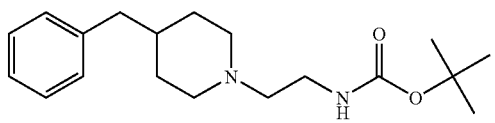

A mixture of 4-benzyl-piperidine (876 mg, 5.0 mmol), (2-bromo-ethyl)-carbamic acid tert-butyl ester (1.12 g, 5.0 mmol) and DIPEA (650 mg, 5 mmol) in THF (30 mL) is heated at reflux for 15 h. The solution is poured into ether (150 mL) and extracted with saturated $Na_2CO_3$ (2×50 mL) and brine (30 mL), dried ($Na_2SO_4$), filtered and concentrated to provide a crude oil. Flash chromatography (EtOAc/heptane: 3/2) provides the title compound.

381C. 2-(4-Benzyl-piperidin-1-yl)-ethylamine

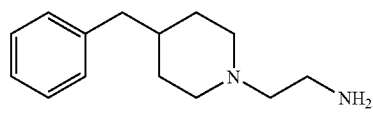

[2-(4-Benzyl-piperidin-1-yl)-ethyl]-carbamic acid tert-butyl ester (1.34 g, 4.2 mmol) is dissolved in $CHCl_3$ (3 mL) and treated with TFA (3 mL) for 2 h at 20° C. The solvent is evaporated, the residue dissolved $CH_2Cl_2$ (100 mL) and washed with 1M aqueous NaOH (2×30 mL). The organic layer is dried ($Na_2SO_4$), filtered and concentrated to provide the title compound.

381D. Methyl-(2-methyl-quinolin-4-yl)-amine

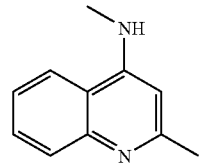

A mixture of 4-chloro-2-methyl-quinoline (4.36 g, 24.5 mmol) and benzylmethylamine (3.13 g, 25.8 mmol) is heated under $N_2$ at 120° C. for 12 h. The residue is dissolved in $CH_2Cl_2$ (50 ml) and washed successively with aqueous saturated $Na_2CO_3$ (50 mL) and 1M aqueous NaOH (50 ml). The $CH_2Cl_2$ layer is evaporated, and the residue is dissolved in MeOH (400 mL) and 4M HCl in dioxane (12 mL). 10% Pd—C (410 mg) are added and the suspension is hydrogenated for 15 h under ambient pressure. The reaction mixture is filtered through a pad of Celite. 1M aqueous NaOH (100 mL) is added and the filtrate is evaporated. The residue is dissolved in water and extracted with $CH_2Cl_2$ (3×50 mL). The combined organic extracts are dried and evaporated to provide the title compound.

381E. 3-[2-(4-Benzyl-piperidin-1-yl)-ethyl]-1-methyl-1-(2-methyl-quinolin-4-yl)-urea

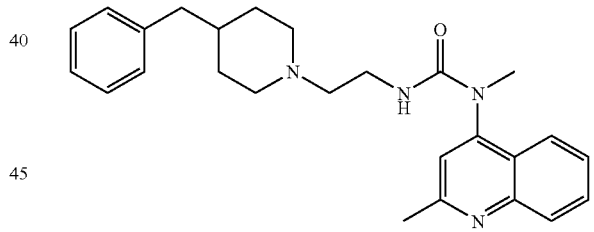

To a stirred solution of CDI (178 mg, 1.1 mmol) in DMSO (5 mL) is added a solution of 2-(4-benzyl-piperidin-1-yl)-ethylamine (218 mg, 1 mmol) in DMSO (1 mL). The reaction mixture is stirred at 20° C. for 3 h. Methyl-(2-methyl-quinolin-4-yl)-amine (173 mg, 1 mmol) is added. To the resulting solution is added in a single portion NaHMDS (2 M in THF, 1.25 mL, 2.5 mmol). The reaction mixture is stirred at 20° C. for 24 h, then $H_2O$ (0.4 mL) is added. The reaction mixture is evaporated and the residue purified by preparative HPLC to provide the title compound.

| Example | | $t_r$ | MS (ES+) |
|---|---|---|---|
| 381. | 3-[2-(4-Benzyl-piperidin-1-yl)-ethyl]-1-methyl-1-(2-methyl-quinolin-4-yl)-urea | 0.58 | 417.12 |

Example 382

1-[3-(4-Benzyl-4-hydroxy-piperidin-1-yl)-propyl]-3-(2-methyl-quinolin-4-yl)-urea 382A. 1-(3-Chloro-propyl)-3-(2-methyl-quinolin-4-yl)-urea

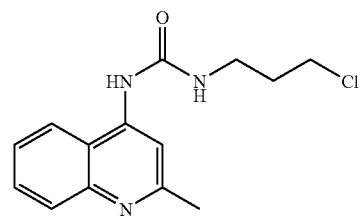

The title compound is prepared from 4-amino-2-methylquinoline and 3-chloropropylisocyanate by the method used in the preparation of Example 1A, 1-(2-chloroethyl)-3-(2-methyl-quinol-4-yl)-urea.

382B. 1-[3-(4-Benzyl-4-hydroxy-piperidin-1-yl)-propyl]-3-(2-methyl-quinolin-4-yl)-urea

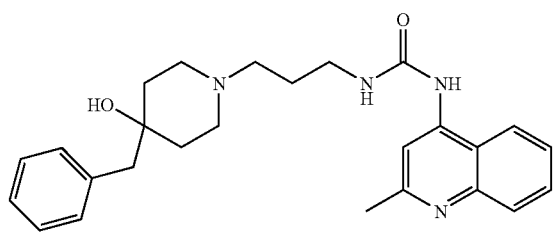

Prepared from 4-hydroxy-4-benzyl-piperidine and 1-(3-chloro-propyl)-3-(2-methyl-quinolin-4-yl)-urea using the method exemplified with Example 341, 1-[2-(4-hydroxy-4-p-tolyl-piperidin-1-yl)-ethyl]-3-(2-methyl-quinolin-4-yl)-urea.

The following compounds are prepared in an analogous fashion.

| Example | | $t_r$ | MS (ES+) |
|---|---|---|---|
| 382. | 1-[3-(4-Benzyl-4-hydroxy-piperidin-1-yl)-propyl]-3-(2-methyl-quinolin-4-yl)-urea | 0.90 | 433.2 |
| 383. | 1-[3-(4-Benzyl-4-hydroxy-piperidin-1-yl)-propyl]-3-quinolin-4-yl-urea | 0.86 | 419.2 |

Example 384

1-[(S)-1-(4-Benzyl-piperidin-1-ylmethyl)-2-methyl-propyl]-3-(2-methyl-quinolin-4-yl)-urea 384A. 1,3-Bis-(2-methyl-quinolin-4-yl)-urea

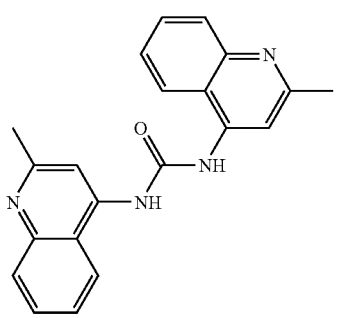

To a suspension of 4-amino-2-methylquinoline (20.24 g, 128 mmol) in THF (100 mL) is added CDI (13.9 g, 85 mmol). The mixture is heated at reflux for 15 h. The resulting precipitate is filtered, stirred with water (100 mL) for 6 h and filtered again. The filtercake is washed with water (20 mL), THF (20 mL) and dried to provide the title compound.

384B. (S)-3-Methyl-2-[3-(2-methyl-quinolin-4-yl)-ureido]-butyric acid

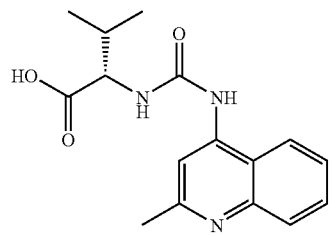

A suspension of 1,3-bis-(2-methyl-quinolin-4-yl)-urea (342.4 mg, 1 mmol), valin methyl ester hydrochloride (167.6 mg, 1 mmol) and DIPEA (0.34 mL, 2 mmol) in MeOH (10 mL) is heated at 80° C. for 15 h. The solvent is evaporated and the residue is dissolved in 6N aqueous HCl (6 mL). The reaction mixture is heated at 90° C. for 12 h. Evaporation and purification by preparative HPLC provides the title compound.

384C. 1-[(S)-1-(4-Benzyl-piperidine-1-carbonyl)-2-methyl-propyl]-3-(2-methyl-quinolin-4-yl)-urea

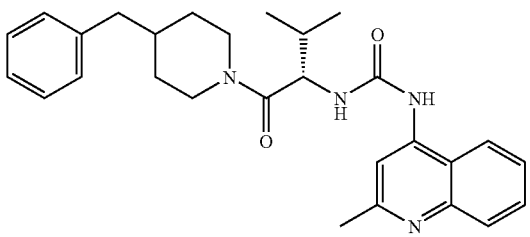

To a solution of (S)-3-methyl-2-[3-(2-methyl-quinolin-4-yl)-ureido]-butyric acid hydrochloride (337.8 mg, 1 mmol), 4-benzylpiperidine (175.3 mg, 1 mmol), HOBt (183 mg, 1.2 mmol) and TEA (0.35 mL, 2.5 mmol) in DMF (10 mL) is added EDC (230.0 mg, 1.2 mmol). The mixture is stirred for 15 h at room temperature and then quenched with sat. aqueous $Na_2CO_3$ (30 mL). The aqueous phase is extracted with $CH_2Cl_2$ (3×20 mL). The combined extracts are dried ($Na_2SO_4$), filtered and evaporated. The residue is purified by flash chromatography ($SiO_2$, $CH_2Cl_2$/MeOH, 5/1) to provide the title compound.

384D. 1-[(S)-1-(4-Benzyl-piperidin-1-ylmethyl)-2-methyl-propyl]-3-(2-methyl-quinolin-4-yl)-urea

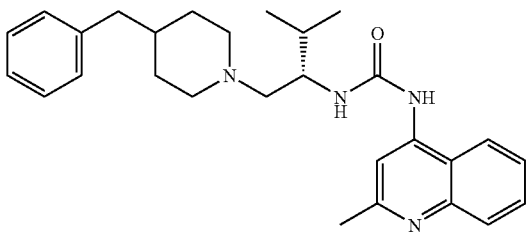

To a solution of 1-[(S)-1-(4-benzyl-piperidine-1-carbonyl)-2-methyl-propyl]-3-(2-methyl-quinolin-4-yl)-urea in THF (10 mL) is added at 0° C. $LiAlH_4$ (40 mg, 1 mmol). The reaction mixture is stirred at room temperature for 15 h and then quenched with EtOAc (1 mL) and sat. $NaHCO_3$ (0.2 mL). The resulting precipitate is removed by filtration and the filtercake washed with MeOH (2×5 mL). The mixture is evaporated and the residue purified by TLC ($SiO_2$, $CH_2Cl_2$/MeOH, 5/1) to provide the title compound.

The following compounds are prepared in an analogous fashion.

| Example | | $t_r$ | MS (ES+) |
|---|---|---|---|
| 384. | 1-[(S)-1-(4-Benzyl-piperidin-1-ylmethyl)-2-methyl-propyl]-3-(2-methyl-quinolin-4-yl)-urea | 0.78 | 445.25 |
| 385. | 1-[(S)-1-Benzyl-2-(4-benzyl-piperidin-1-yl)-ethyl]-3-(2-methyl-quinolin-4-yl)-urea | 0.82 | 493.24 |
| 386. | 1-[(S)-1-(4-Benzyl-piperidin-1-ylmethyl)-3-methyl-butyl]-3-(2-methyl-quinolin-4-yl)-urea | 0.81 | 459.27 |
| 387. | 1-[(S)-2-(4-Benzyl-piperidin-1-yl)-1-methyl-ethyl]-3-(2-methyl-quinolin-4-yl)-urea | 0.75 | 417.19 |

Example 388

1-[2-(4-Benzyl-4-hydroxy-piperidin-1-yl)-2-phenyl-ethyl]-3-(2-methyl-quinolin-4-yl)-urea

388A. 1-(2-Amino-1-phenyl-ethyl)-4-benzyl-piperidin-4-ol

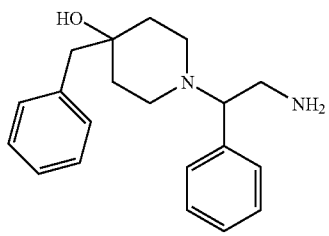

To a suspension of 4-benzyl-piperidin-4-ol (1.0 g, 5.2 mmol), benzaldehyde (0.83 g, 7.8 mmol) and $MgSO_4$ (0.31 g, 2.6 mmol) in 1-methyl-2-pyrrolidone (5 mL) is added acetone cyanohydrine (0.45 g, 5.2 mmol). The reaction mixture is heated at 50° C. for 2 h, then cooled to room temperature and quenched with ice (20 g) and sat. $NaHCO_3$ (50 mL). The aqueous phase is extracted with $Et_2O$ (3×100 mL), the combined organic extracts are washed with sat. NaCl (20 mL), dried ($Na_2SO_4$), filtered and evaporated. The residue is dissolved in THF (20 mL) and added to a suspension of $LiAlH_4$ (1.1 g, 27.6 mmol) in THF (80 mL) at 0° C. The reaction mixture is stirred for 15 h at room temperature and quenched with EtOAc (250 mL), MeOH (20 mL) and sat. $NaHCO_3$ (5 mL). The precipitate is filtered off, washed with MeOH (20 mL) and the filtrate evaporated. Purification by preparative HPLC provides the title compound.

388B. 2-Methyl-quinoline-4-carboxylic acid

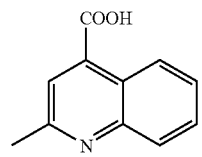

The compound is prepared from isatin and acetone using the method of Keneko C. et al., Chem. Pharm. Bull. (1980) 28, 1157-1171.

388C. 4-Isocyanato-2-methyl-quinoline

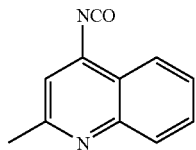

To a solution of 2-methyl-quinoline-4-carboxylic acid (276 mg, 1.2 mmol) in DMF (4 mL) at 0° C. is added triethylamine (1.22 mg, 1.2 mmol) and slowly (30 min) DPPA (332 mg, 1.2 mmol). The reaction mixture is stirred for 2 h at 0° C. and 12 h at 20° C. The reaction is quenched with ice (10 g) and extracted with Et₂O (6×30 mL). The combined organic extracts are washed successively with saturated NaHCO₃ (2×15 mL) and water (2×10 mL), and are evaporated without heating in vacuo. The residue is dissolved in dry toluene and heated at reflux for 2 h. The resulting solution is carried forward without further isolation of the title compound.

388D. 1-[2-(4-Benzyl-4-hydroxy-piperidin-1-yl)-2-phenyl-ethyl]-3-(2-methyl-quinolin-4-yl)-urea

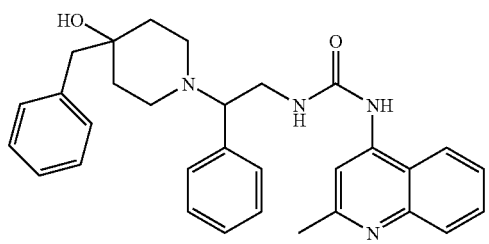

To a solution of 1-(2-amino-1-phenyl-ethyl)₄-benzyl-piperidin-4-ol (54.3 mg, 0.18 mmol) in CH₂Cl₂ is added a freshly prepared solution of 4-isocyanato-2-methyl-quinoline (33.8 mg, 0.16 mmol) in toluene (2 mL). The mixture is stirred for 15 h at 20° C. Evaporation of the solvent and purification by HPLC provides the title compound.

| Example | | $t_r$ | MS (ES+) |
|---|---|---|---|
| 388. | 1-[2-(4-Benzyl-4-hydroxy-piperidin-1-yl)-2-phenyl-ethyl]-3-(2-methyl-quinolin-4-yl)-urea | 0.67 | 495.41 |

Example 389

1-[2-(4-Benzyl-4-hydroxy-piperidin-1-yl)-ethyl]-3-(2-cyclopropyl-quinolin-4-yl)-urea

389A. 1-(2-Amino-ethyl)-4-benzyl-piperidin-4-ol

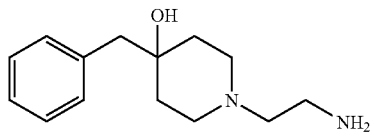

The title compound is prepared from 4-hydroxy-4-benzyl-piperidine using the method for the preparation of Example 381C.

389B. 2-Cyclopropyl-quinoline-4-carboxylic acid

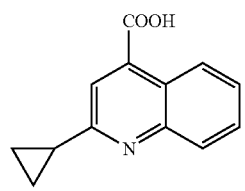

The compound is prepared from isatin and cyclopropyl-methylketone using the method of Keneko C. et al., Chem. Pharm. Bull. (1980) 28, 1157-1171.

389C. 1-[2-(4-Benzyl-4-hydroxy-piperidin-1-yl)-ethyl]-3-(2-cyclopropyl-quinolin-4-yl)-urea

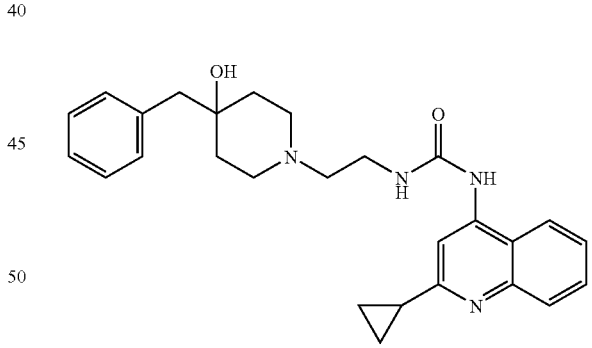

The compound is prepared from 1-(2-amino-ethyl)-4-benzyl-piperidin-4-ol and 2-cyclopropyl-quinoline-4-carboxylic acid according to the method described for Example 388D.

| Example | | $t_r$ | MS (ES+) |
|---|---|---|---|
| 389. | 1-[2-(4-Benzyl-4-hydroxy-piperidin-1-yl)-ethyl]-3-(2-cyclopropyl-quinolin-4-yl)-urea | 1.16 | 445.2 |

Example 390

1-[2-(4-Benzyl-4-hydroxy-piperidin-1-yl)-ethyl]-3-(8-benzyl-2-methyl-quinolin-4-yl)-urea

390A. 8-Benzyl-2-methyl-quinoline-4-carboxylic acid

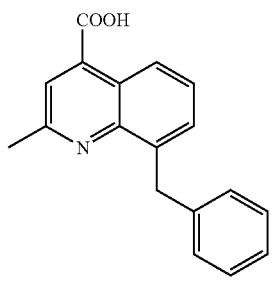

The compound is prepared from 2-benzylaniline, acetaldehyde and pyruvic acid using the method of Irving, Clifton, J. Chem. Soc. (1959) 288.

390B. 1-[2-(4-Benzyl-4-hydroxy-piperidin-1-yl)-ethyl]-3-(8-benzyl-2-methyl-quinolin-4-yl)-urea

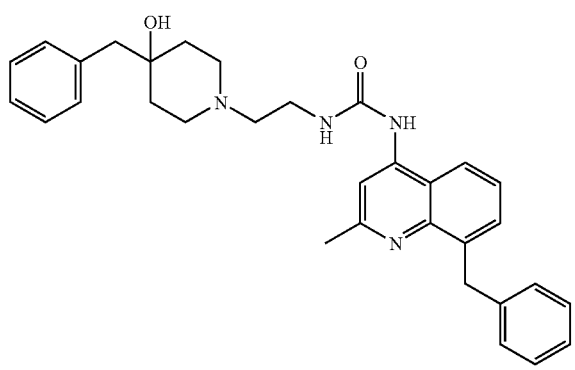

The compound is prepared from 1-(2-amino-ethyl)-4-benzyl-piperidin-4-ol and 8-benzyl-2-methyl-quinoline-4-carboxylic acid according to the method described for Example 388D.

| Example | | $t_r$ | MS (ES+) |
|---|---|---|---|
| 390. | 1-[2-(4-Benzyl-4-hydroxy-piperidin-1-yl)-ethyl]-3-(8-benzyl-2-methyl-quinolin-4-yl)-urea | 0.78 | 509.13 |

Example 391

1-[2-(4-Benzyl-4-hydroxy-piperidin-1-yl)-ethyl]-3-(7-methyl-[1,8]naphthyridin-4-yl)-urea

391 A. 1-(2-Chloro-ethyl)-3-(2-methyl-[1,8]naphthyridin-4-yl)-urea

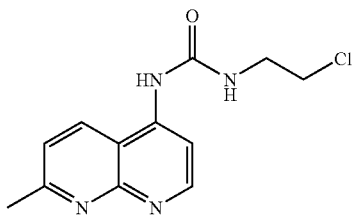

Prepared from 2-methyl-[1,8]napthyrid-4-yl amine (Barlin G B, Tan W L, "Potential Antimalarials. I 1,8-naphthyridines", Aust J Chem (1984) 37, 1065-1073. Radivov R, Haimova M, Simova E "Synthesis of 4-Amino-3-Pyridiyl and 4-Amino-5-Pyrimidyl Aryl Ketones and Related Compounds via an ortho-Lithiation Reaction", Synthesis (1986), 886-891), using the method for the preparation of 1-(2-chloroethyl)-3-quinolin-4-yl-urea.

391 B. 1-[2-(4-Benzyl-4-hydroxy-piperidin-1-yl)-ethyl]-3-(7-methyl-[1,8]naphthyridin-4-yl)-urea

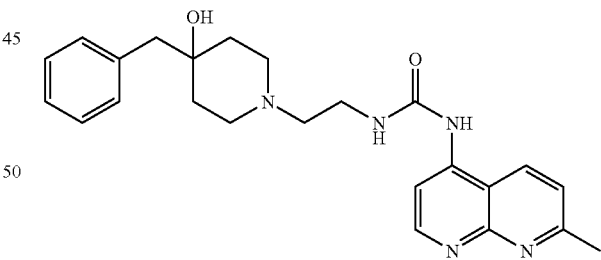

Prepared from 4-benzyl-4-hydroxypiperidine and 1-(2-chloro-ethyl)-3-(2-methyl-[1,8]naphthyridin-4-yl)-urea according to the method used in the preparation of Example 368C.

| Example | | $t_r$ | MS (ES+) |
|---|---|---|---|
| 391. | 1-[2-(4-Benzyl-4-hydroxy-piperidin-1-yl)-ethyl]-3-(7-methyl-[1,8]naphthyridin-4-yl)-urea | 0.79 | 420.2 |

Example 392

1-{2-[4-(3-Methyl-benzylidene)-piperidin-1-yl]-ethyl}-3-(2-methyl-quinolin-4-yl)-urea

392A. 4-(3-Methyl-benzylidene)-piperidine-1-carboxylic acid tert-butyl ester

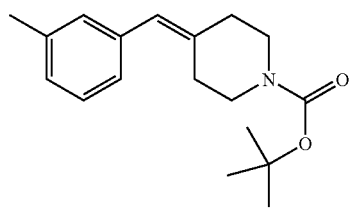

Sodium hydride (0.4 g, 16.6 mmol) is added to dry DMSO (30 mL) and the mixture is heated at 80° C. for 1 h. After cooling to 20° C. 4-fluorophenylmethyl triphenylphosphonium chloride (4.46 g, 11 mmol) is added portionwise under nitrogen, and the mixture is stirred for 15 min. Then 4-piperidone-1-carboxylic acid tert-butyl ester (2 g, 10 mmol) is added and the mixture is stirred for 15 h at room temperature followed by heating to 80° C. for 8 h. The reaction mixture is cooled to room temperature and poured onto ice (75 g). The resulting mixture is extracted with ether (3×120 mL). The organic extracts are dried over sodium sulfate and evaporated. The resulting oil is purified by flash chromatography ($SiO_2$, EtOAc/heptane 1/5) to provide the title compound.

392B. 4-(3-Methyl-benzylidene)-piperidine

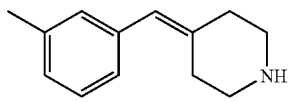

To a solution of 4-(3-methyl-benzylidene)-piperidine-1-carboxylic acid tert-butyl ester (287.4 mg, 1 mmol) in $CH_2Cl_2$ (1 mL) TFA (1 mL) is added. The solution is stirred for 2 h at 20° C. The solvent is evaporated, the residue dissolved $CH_2Cl_2$ (75 mL) and washed with 1 M aqueous NaOH (2×20 mL). The organic layer is dried ($Na_2SO_4$), filtered and concentrated to provide the title compound.

392C. [3-(2-Methyl-quinolin-4-yl)-ureido]-acetic acid ethyl ester

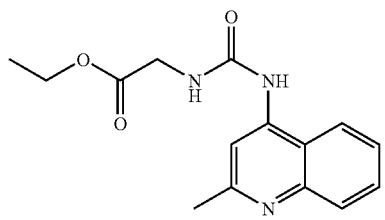

A suspension of 4-amino-2-methylchinoline (4.0 g, 25.3 mmol) in dry THF (80 mL) is cooled to −14° C. and ethyl isocyanatoacetate (3.3 mL, 27.4 mmol) is added dropwise under vigourous stirring. The reaction is warmed to room temperature and stirred for 4 h. Further ethyl isocyanatoacetate (0.6 mL, 5 mmol) is added and the reaction mixture stirred for 15 h. The solvent is evaporated and the residue crystallized from $CHCl_3$-heptane (1/5) to provide the title compound.

392D. (3-Quinolin-4-yl-ureido)-acetic acid

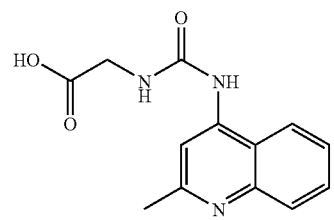

[3-(2-Methyl-quinolin-4-yl)-ureido]-acetic acid ethyl ester (7.2 g, 25 mmol) is suspended in 6N aqueous HCl (250 mL), and the mixture is heated at 80° C. for 15 h. The mixture is cooled, filtered from the resulting precipitate and the solid dried to provide the title compound as hydrochloride salt.

392E. 1-{2-[4-(3-Methyl-benzylidene)-piperidin-1-yl]-2-oxo-ethyl}-3-(2-methyl-quinolin-4-yl)-urea

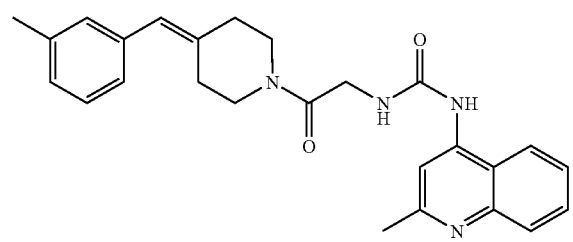

A suspension of (3-quinolin-4-yl-ureido)-acetic acid hydrochloride (281.7 mg, 1 mmol), 4-(3-methyl-benzylidene)-piperidine (187.3 mg, 1 mmol), TEA (1 mL, 7 mmol) in DMF (4 mL) and $T_3P$ (50% in EtOAc, 1 mL, 1.7 mmol) is stirred for 2 h at room temperature. The DMF is evaporated, the residue dissolved in $CH_2Cl_2$ (150 mL) and washed with 1M aqueous NaOH (50 mL) and brine (30 mL). The organic phase is dried ($Na_2SO_4$), filtered and evaporated to provide the crude title compound.

392F. 1-{2-[4-(3-Methyl-benzylidene)-piperidin-1-yl]-ethyl}-3-(2-methyl-quinolin-4-yl)-urea

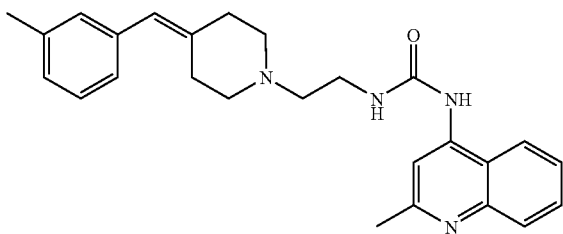

To a suspension of LiAlH$_4$ (100 mg, 2.6 mmol) in THF (40 mL) is added a solution of crude 1-{2-[4-(3-methyl-benzylidene)-piperidin-1-yl]-2-oxo-ethyl}$_3$-(2-methyl-quinolin-4-yl)-urea (1 mmol) in THF (10 mL) and the mixture is stirred at room temperature for 15 h. The suspension is poured slowly into EtOAc (200 mL) and MeOH (10 mL) and, subsequently, sat. NaHCO$_3$ (dropwise, total of 1.5 mL) is added. The precipitate is filtered off and washed with MeOH (2×20 mL). The filtrate is dried (Na$_2$SO$_4$), filtered and evaporated. The residue is purified by flash chromatography (SiO$_2$, CH$_2$Cl$_2$-MeOH, 10:1) to provide the title compound.

The following compounds are prepared in an analogous fashion.

| | Example | t$_r$ | MS (ES+) |
|---|---|---|---|
| 392. | 1-{2-[4-(3-Methyl-benzylidene)-piperidin-1-yl]-ethyl}-3-(2-methyl-quinolin-4-yl)-urea | 0.77 | 415.18 |
| 393. | 1-{2-[4-(4-Methyl-benzylidene)-piperidin-1-yl]-ethyl}-3-(2-methyl-quinolin-4-yl)-urea | 0.77 | 415.19 |
| 394. | 1-{2-[4-(2-Methyl-benzylidene)-piperidin-1-yl]-ethyl}-3-(2-methyl-quinolin-4-yl)-urea | 0.76 | 415.21 |
| 395. | 1-{2-[4-(4-Methoxy-benzylidene)-piperidin-1-yl]-ethyl}-3-(2-methyl-quinolin-4-yl)-urea | 0.74 | 431.25 |
| 396. | 1-{2-[4-(4-Fluoro-benzylidene)-piperidin-1-yl]-ethyl}-3-(2-methyl-quinolin-4-yl)-urea | 0.75 | 419.21 |
| 397. | 1-{2-[4-(4-Bromo-benzylidene)-piperidin-1-yl]-ethyl}-3-(2-methyl-quinolin-4-yl)-urea | 1.02 | 479.33 |

Example 398

1-{2-[4-(3-Methyl-benzyl)-piperidin-1-yl]-ethyl}-3-(2-methyl-quinolin-4-yl)-urea

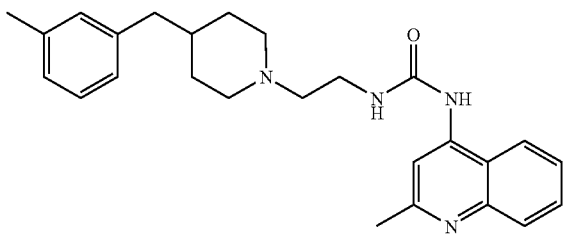

A suspension of 1-{2-[4-(3-methyl-benzylidene)-piperidin-1-yl]-ethyl}-3-(2-methyl-quinolin-4-yl)-urea (21 mg, 0.05 mmol), 2M aqueous HCl (0.5 mL, 1 mmol) and Pd—C (10%, 5 mg) in MeOH (2 mL) is stirred under hydrogen atmosphere for 6 h. The catalyst is filtered off and the filtrate evaporated to provide the title compound as hydrochloride salt.

The following compounds are prepared in an analogous fashion.

| | Example | t$_r$ | MS (ES+) |
|---|---|---|---|
| 398. | 1-{2-[4-(3-Methyl-benzyl)-piperidin-1-yl]-ethyl}-3-(2-methyl-quinolin-4-yl)-urea | 0.77 | 417.26 |
| 399. | 1-{2-[4-(2-Methyl-benzyl)-piperidin-1-yl]-ethyl}-3-(2-methyl-quinolin-4-yl)-urea | 0.77 | 417.26 |
| 400. | 1-{2-[4-(4-Methoxy-benzyl)-piperidin-1-yl]-ethyl}-3-(2-methyl-quinolin-4-yl)-urea | 0.74 | 433.25 |
| 401. | 1-{2-[4-(4-Fluoro-benzyl)-piperidin-1-yl]-ethyl}-3-(2-methyl-quinolin-4-yl)-urea | 0.75 | 421.23 |
| 402. | 1-{2-[4-(4-Methyl-benzyl)-piperidin-1-yl]-ethyl}-3-(2-methyl-quinolin-4-yl)-urea | 0.76 | 417.27 |

Example 403

1-{2-[3-(2-Methyl-quinolin-4-yl)-ureido]-ethyl}-piperidine-4-carboxylic acid ethyl ester The compound is prepared from 1-(2-chloro-ethyl)-3-(2-methyl-quinolin-4-yl)-urea (Example 1A, 1.32 g, 5 mmol)) and ethyl nipecotate (1.57 g, 10 mmol) using the method of Example 1.

| | Example | t$_r$ | MS (ES+) |
|---|---|---|---|
| 403. | 1-{2-[3-(2-Methyl-quinolin-4-yl)-ureido]-ethyl}-piperidine-4-carboxylic acid ethyl ester | 0.69 | 385.21 |

Example 404

1-{2-[3-(2-Methyl-quinolin-4-yl)-ureido]-ethyl}-piperidine-4-carboxylic acid methyl-phenyl-amide

404A. 1-{2-[3-(2-Methyl-quinolin-4-yl)-ureido]-ethyl}-piperidine-4-carboxylic acid dihydrochloride

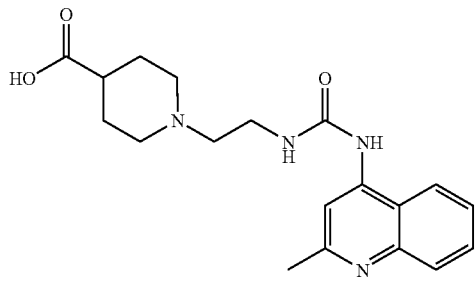

1-{2-[3-(2-Methyl-quinolin-4-yl)-ureido]-ethyl}-piperidine-4-carboxylic acid ethyl ester (0.9 g, 2.3 mmol) is dissolved in 6N aqueous HCl (10 mL) and the mixture is heated at 50° C. for 48 h. The reaction mixture is evaporated and the residue is dried to provide the title compound as hydrochloride salt.

404B. 1-{2-[3-(2-Methyl-quinolin-4-y)-ureido]-ethyl}-piperidine-4-carboxylic acid methyl-phenyl-amide

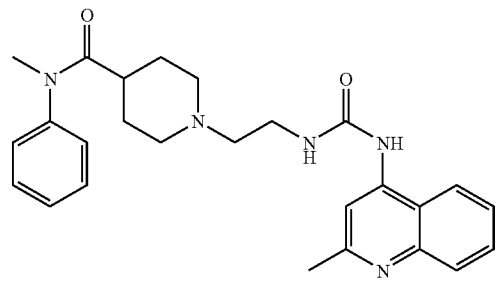

To a suspension of 1-{2-[3-(2-methyl-quinolin-4-yl)-ureido]-ethyl}-piperidine-4-carboxylic acid dihydrochloride (64.25 mg, 0.15 mmol), TEA (0.07 mL, 0.5 mmol) and N-methylaniline (11 mg, 0.1 mmol) in DMF (0.6 mL) is is added $T_3P$ (50% in EtOAc, 0.07 mL, 0.12 mmol) at room temperature. The mixture is stirred for 15 h, quenched with sat. $Na_2CO_3$ (5 mL) and extracted with $CH_2Cl_2$ (3×10 mL). The organic phases are dried ($Na_2SO_4$), filtered, evaporated and the residue purified by preparative HPLC to provide the title compound.

The following compounds are prepared in an analogous fashion.

| Example | | $t_r$ | MS (ES+) |
|---|---|---|---|
| 404. | 1-{2-[3-(2-Methyl-quinolin-4-yl)-ureido]-ethyl}-piperidine-4-carboxylic acid methyl-phenyl-amide | 0.55 | 446.09 |
| 405. | 1-{2-[3-(2-Methyl-quinolin-4-yl)-ureido]-ethyl}-piperidine-4-carboxylic acid naphthalen-2-ylamide | 0.62 | 482.10 |
| 406. | 1-{2-[3-(2-Methyl-quinolin-4-yl)-ureido]-ethyl}-piperidine-4-carboxylic acid naphthalen-1-ylamide | 0.60 | 482.08 |
| 407. | 1-{2-[3-(2-Methyl-quinolin-4-yl)-ureido]-ethyl}-piperidine-4-carboxylic acid benzylamide | 0.54 | 446.11 |
| 408. | 1-{2-[3-(2-Methyl-quinolin-4-yl)-ureido]-ethyl}-piperidine-4-carboxylic acid phenethyl-amide | 0.56 | 460.12 |
| 409. | 1-{2-[3-(2-Methyl-quinolin-4-yl)-ureido]-ethyl}-piperidine-4-carboxylic acid benzyl-methyl-amide | 0.56 | 460.09 |
| 410. | 1-{2-[3-(2-Methyl-quinolin-4-yl)-ureido]-ethyl}-piperidine-4-carboxylic acid methyl-phenethyl-amide | 0.58 | 474.12 |
| 411. | 1-{2-[3-(2-Methyl-quinolin-4-yl)-ureido]-ethyl}-piperidine-4-carboxylic acid (4-phenyl-butyl)-amide | 0.63 | 488.12 |
| 412. | 1-{2-[3-(2-Methyl-quinolin-4-yl)-ureido]-ethyl}-piperidine-4-carboxylic acid benzyl-phenyl-amide | 0.66 | 522.11 |
| 413. | 1-{2-[3-(2-Methyl-quinolin-4-yl)-ureido]-ethyl}-piperidine-4-carboxylic acid (4-chloro-phenyl)-methyl-amide | 0.60 | 480.05 |
| 414. | 1-{2-[3-(2-Methyl-quinolin-4-yl)-ureido]-ethyl}-piperidine-4-carboxylic acid (4-bromo-phenyl)-amide | 0.62 | 509.98 |
| 415. | 1-{2-[3-(2-Methyl-quinolin-4-yl)-ureido]-ethyl}-piperidine-4-carboxylic acid (3-chloro-phenyl)-amide | 0.60 | 466.03 |
| 416. | 1-{2-[3-(2-Methyl-quinolin-4-yl)-ureido]-ethyl}-piperidine-4-carboxylic acid (2-chloro-phenyl)-methyl-amide | 0.58 | 480.05 |
| 417. | 1-{2-[4-(4-Benzyl-piperidine-1-carbonyl)-piperidin-1-yl]-ethyl}-3-(2-methyl-quinolin-4-yl)-urea | 0.66 | 514.12 |
| 418. | 1-{2-[3-(2-Methyl-quinolin-4-yl)-ureido]-ethyl}-piperidine-4-carboxylic acid benzyl-phenethyl-amide | 0.69 | 550.13 |
| 419. | 1-{2-[3-(2-Methyl-quinolin-4-yl)-ureido]-ethyl}-piperidine-4-carboxylic acid 4-bromo-benzylamide | 0.60 | 523.95 |
| 420. | 1-{2-[3-(2-Methyl-quinolin-4-yl)-ureido]-ethyl}-piperidine-4-carboxylic acid (3-phenyl-propyl)-amide | 0.60 | 474.12 |
| 421. | 1-{2-[3-(2-Methyl-quinolin-4-yl)-ureido]-ethyl}-piperidine-4-carboxylic acid benzyl-ethyl-amide | 0.65 | 474.49 |
| 422. | 1-{2-[3-(2-Methyl-quinolin-4-yl)-ureido]-ethyl}-piperidine-4-carboxylic acid methyl ester | 0.54 | 371.35 |

Example 423

1-{2-[3-(2-Methyl-quinolin-4-yl)-ureido]-ethyl}-4-phenyl-piperidine-4-carboxylic acid methyl ester 423A. 4-Phenyl-piperidine-4-carboxylic acid methyl ester

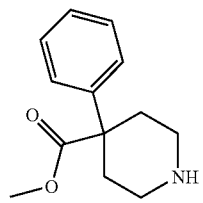

To a solution of 4-phenyl-piperidine-4-carboxylic acid tosylate (4.6 g, 20 mmol) in MeOH (25 mL) is added TMSCl (10 mL) and the reaction mixture is stirred at 50° C. for 15 h. The reaction mixture is cooled and evaporated. The residue is taken up in MeOH (5 mL), poured into sat. $Na_2CO_3$ (100 mL) and extracted with $CH_2Cl_2$ (3×50 mL). The combined organic extracts are dried ($Na_2SO_4$), filtered and evaporated to provide the title compound.

423B. 1-{2-[3-(2-Methyl-quinolin-4-yl)-ureido]-ethyl}-4-phenyl-piperidine-4-carboxylic acid methyl ester

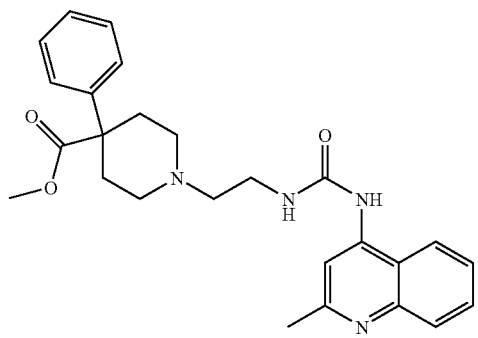

The compound is prepared from 1-(2-chloro-ethyl)-3-(2-methyl-quinolin-4-yl)-urea (Example 1A, 2.6 g, 10 mmol)) and 4-phenyl-piperidine-4-carboxylic acid methyl ester (4.38 g, 20 mmol) using the method of Example 1.

| | Example | $t_r$ | MS (ES+) |
|---|---|---|---|
| 423. | 1-{2-[3-(2-Methyl-quinolin-4-yl)-ureido]-ethyl}-4-phenyl-piperidine-4-carboxylic acid methyl ester | 0.59 | 447.07 |

Example 424

1-{2-[3-(2-Methyl-quinolin-4-yl)-ureido]-ethyl}-4-phenyl-piperidine-4-carboxylic acid

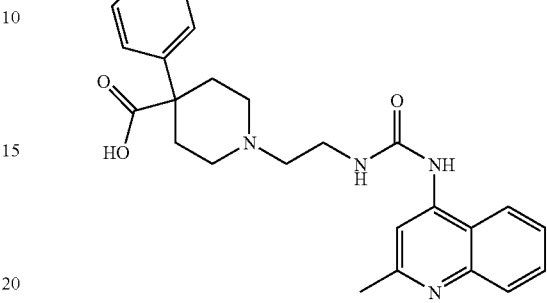

A solution of 1-{2-[3-(2-Methyl-quinolin-4-yl)-ureido]-ethyl}-4-phenyl-piperidine-4-carboxylic acid methyl ester (1.25 g, 2.8 mmol) in 6N aqueous HCl (10 mL) is heated at 90° C. for 48 h. The reaction mixture is evaporated to provide the title compound as dihydrochloride salt.

| | Example | $t_r$ | MS (ES+) |
|---|---|---|---|
| 424. | 1-{2-[3-(2-Methyl-quinolin-4-yl)-ureido]-ethyl}-4-phenyl-piperidine-4-carboxylic acid | 0.60 | 433.38 |

Example 425

1-{2-[3-(2-Methyl-quinolin-4-yl)-ureido]-ethyl}-4-phenyl-piperidine-4-carboxylic acid benzyl-methyl-amid

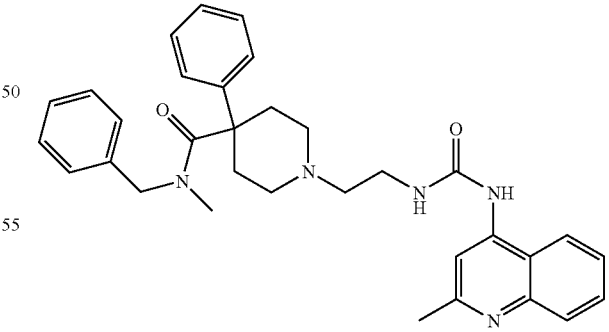

The compound is prepared from 1-{2-[3-(2-methyl-quinolin-4-yl)-ureido]-ethyl}-4-phenyl-piperidine-4-carboxylic acid dihydrochloride and benzylmethylamine using the method of Example 404B.

The following compounds are prepared in an analogous fashion.

| Example | | $t_r$ | MS (ES+) |
|---|---|---|---|
| 425. | 1-{2-[3-(2-Methyl-quinolin-4-yl)-ureido]-ethyl}-4-phenyl-piperidine-4-carboxylic acid benzyl-methyl-amide | 0.69 | 536.10 |
| 426. | 1-{2-[3-(2-Methyl-quinolin-4-yl)-ureido]-ethyl}-4-phenyl-piperidine-4-carboxylic acid naphthalen-2-ylamide | 0.78 | 558.11 |
| 427. | 1-{2-[3-(2-Methyl-quinolin-4-yl)-ureido]-ethyl}-4-phenyl-piperidine-4-carboxylic acid methyl-phenethyl-amide | 0.70 | 550.15 |
| 428. | 1-{2-[3-(2-Methyl-quinolin-4-yl)-ureido]-ethyl}-4-phenyl-piperidine-4-carboxylic acid benzyl-ethyl-amide | 0.74 | 550.52 |
| 429. | 1-{2-[3-(2-Methyl-quinolin-4-yl)-ureido]-ethyl}-4-phenyl-piperidine-4-carboxylic acid dimethylamide | 0.63 | 460.40 |
| 430. | 1-{2-[3-(2-Methyl-quinolin-4-yl)-ureido]-ethyl}-4-phenyl-piperidine-4-carboxylic acid diethylamide | 0.68 | 488.49 |

Example 431

4-Benzyl-1-{2-[3-(2-methyl-quinolin-4-yl)-ureido]-ethyl}-piperidine-4-carboxylic acid

431A. 1,4-Dibenzyl-piperidine-4-carboxylic acid ethyl ester

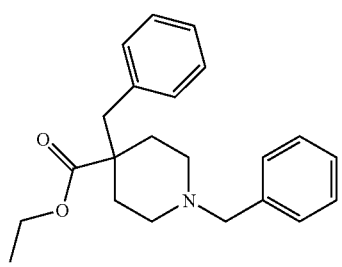

To a solution of NaHMDS in THF (1M, 80 mL, 80 mmol) at −78° C. is added a solution of ethyl nipecotate (5.5 g, 35 mmol) in THF (20 mL). The mixture is stirred at −78° C. for 30 min and then warmed to room temperature. A solution of benzylbromide (9.5 mL, 80 mmol) in THF (40 mL) is added (15 min) to the solution and stirring is continued for 15 h. The mixture is poured into ether (200 mL) and extracted with 1M aqueous HCl (3×50 mL). The aqueous extracts are washed with ether (50 mL) and adjusted to pH 14 with solid $Na_2CO_3$ and 33% NaOH and then extracted with $CH_2Cl_2$ (3×100 mL). The organic extracts are dried ($Na_2SO_4$), filtered and evaporated, the residue purified by flash chromatography ($CH_2Cl_2$-MeOH 10:1) to provide the title compound.

431B. 4-Benzyl-piperidine-4-carboxylic acid ethyl ester

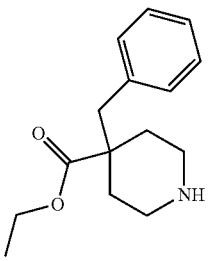

1,4-Dibenzyl-piperidine-4-carboxylic acid ethyl ester (11.8 g, 35 mmol) is dissolved in MeOH (200 mL) and 1M aqueous HCl (40 mL) and Pd—C (10%, 1 g) are added. The mixture is hydrogenated (7 bar, 70° C.) for 15 h. The catalyst is filtered off and the solvent evaporated to provide the title compound.

431C. (2-Bromo-ethyl)-carbamic acid benzyl ester

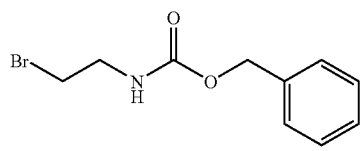

2-Bromoethylamine hydrobromide (15 g, 73 mmol) and N-(benzyloxycarbonyloxy)succinimide (15.5 g, 62 mmol) are suspended in $CH_2Cl_2$ (150 mL) at 0° C. TEA (9 mL, 65 mmol) is added slowly keeping the temperature at 0° C. After 1 h the mixture is washed with 0.5M aqueous $KHSO_4$ (50 mL) and brine (50 mL), the organic phase is dried ($Na_2SO_4$), filtered and evaporated to provide the title compound.

431D. 4-Benzyl-1-(2-benzyloxycarbonylamino-ethyl)-piperidine-4-carboxylic acid ethyl ester

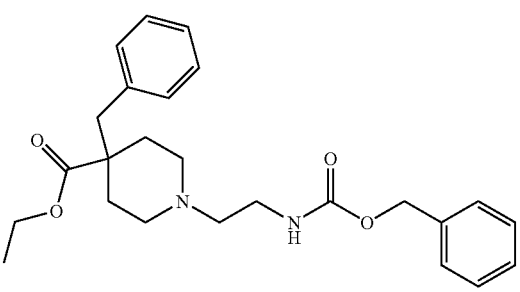

4-Benzyl-piperidine-4-carboxylic acid ethyl ester (2.5 g, 10 mmol), (2-bromo-ethyl)-carbamic acid benzyl ester (2.58 g, 10 mmol) and DIPEA (1.7 mL, 10 mmol) are dissolved in THF (50 mL) and heated at 80° C. for 15 h. The mixture is poured into $Et_2O$ (200 mL) and washed with sat. $Na_2CO_3$ (50 mL). The ether phase is extracted with 1M aqueous HCl (3×50 mL), the aqueous extracts washed with ether (50 mL)

and adjusted to pH 14 with cooled 33% aqueous NaOH. The aqueous phase is extracted with CH$_2$Cl$_2$ (4×50 mL). The organic extracts are dried (Na$_2$SO$_4$), filtered and evaporated to provide the title compound.

431E.
1-(2-Amino-ethyl)-4-benzyl-piperidine-4-carboxylic acid ethyl ester

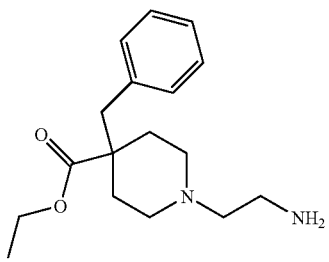

4-Benzyl-1-(2-benzyloxycarbonylamino-ethyl)-piperidine-4-carboxylic acid ethyl ester (4.25 g, 10 mmol) is dissolved in MeOH (100 mL) and Pd—C (10%, 0.5 g) is added. The mixture is hydrogenated (7 bar, 20° C.) for 2 h. The catalyst is filtered off and the solvent evaporated to provide the title compound.

431F.
1-(2-Amino-ethyl)-4-benzyl-piperidine-4-carboxylic acid

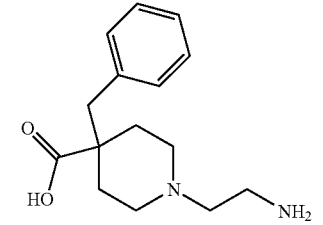

1-(2-Amino-ethyl)-4-benzyl-piperidine-4-carboxylic acid ethyl ester (2.5 g, 10 mmol) is dissolved in 6N aqueous HCl (40 mL) and the mixture heated at 90° C. for 96 h. The reaction mixture is evaporated to provide the title compound as hydrochloride salt.

431G. 4-Benzyl-1-{2-[3-(2-methyl-quinolin-4-yl)-ureido]-ethyl}-piperidine-4-carboxylic acid

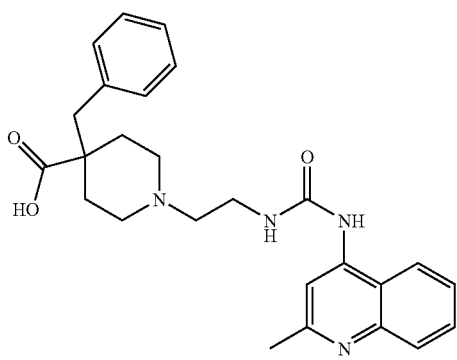

1-(2-Amino-ethyl)-4-benzyl-piperidine-4-carboxylic acid dihydrochloride (3.35 g, 10 mmol), 1,3-bis-(2-methyl-quinolin-4-yl)-urea (3.43 g, 10 mmol) and TEA (5 mL, 36 mmol) are suspended in THF (50 mL) and heated at reflux for 48 h. The solvent is evaporated and the residue purified by HPLC to provide the title compound.

| Example | | t$_r$ | MS (ES+) |
|---|---|---|---|
| 431. | 4-Benzyl-1-{2-[3-(2-methyl-quinolin-4-yl)-ureido]-ethyl}-piperidine-4-carboxylic acid | 0.62 | 477.39 |

Example 432

4-Benzyl-1-{2-[3-(2-methyl-quinolin-4-yl)-ureido]-ethyl}-piperidine-4-carboxylic acid benzyl-ethyl-amide

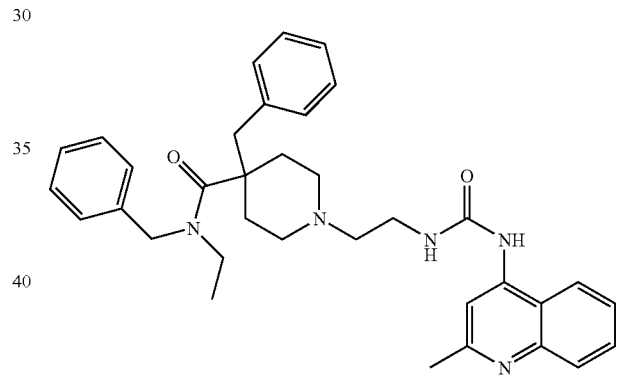

The compound is prepared from 4-benzyl-1-{2-[3-(2-methyl-quinolin-4-yl)-ureido]-ethyl}-piperidine-4-carboxylic acid and benzylethylamine using the method of Example 257C.

| Example | | t$_r$ | MS (ES+) |
|---|---|---|---|
| 432. | 4-Benzyl-1-{2-[3-(2-methyl-quinolin-4-yl)-ureido]-ethyl}-piperidine-4-carboxylic acid benzyl-ethyl-amide | 0.75 | 564.45 |
| 433. | 4-Benzyl-1-{2-[3-(2-methyl-quinolin-4-yl)-ureido]-ethyl}-piperidine-4-carboxylic acid methyl ester | 0.67 | 461.46 |

Example 434

1-[2-(4-Benzyl-4-hydroxy-piperidin-1-yl)-ethyl]-3-
[2-(benzyl-methyl-amino)-Pyridin-4-yl]-urea

434A. 2-(Benzyl-methyl-amino)-isonicotinic acid

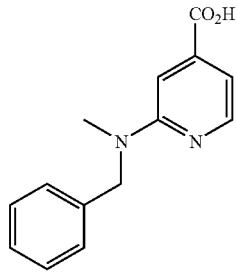

A mixture of 2-chloro-pyridine-4-carboxylic acid (300 mg, 1.9 mmol), benzylmethylamine (230 mg, 1.9 mmol) and triethylamine (192 mg, 1.9 mmol) is heated at 120° C. for 12 h. The residue is dissolved in $CH_2Cl_2$ (30 mL) and extracted with 1M aqueous NaOH (3×5 mL). The aqueous layer is adjusted to pH 1-2 with 12N aqueous HCl and extracted with EtOAc (6×5 mL). The organic extracts are combined, dried ($MgSO_4$), and evaporated to provide the title compound.

434B. 2-(Benzyl-methyl-amino)-4-isocyanato-pyridine

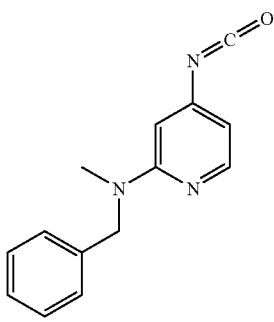

The compound is prepared from 2-(benzyl-methyl-amino)-pyridine-4-carboxylic acid (780 mg, 3.2 mmol) using the method described for Example 388C.

434C. 1-[2-(4-Benzyl-4-hydroxy-piperidin-1-yl)-ethyl]-3-[2-(benzyl-methyl-amino)-pyridin-4-yl]-urea

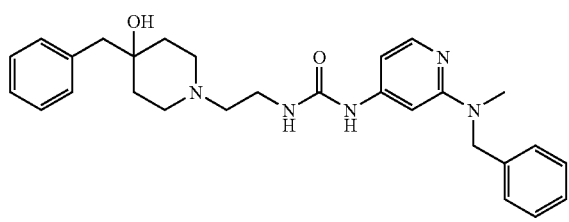

The compound is prepared from 1-(2-amino-ethyl)-4-benzyl-piperidin-4-ol (93 mg, 0.40 mmol) and 2-(benzyl-methyl-amino)-4-isocyanato-pyridine (95.7 mg, 0.40 mmol) using the method described for Example 388D.

The following compounds are prepared in an analogous fashion.

| Example | | $t_r$ | MS (ES+) |
|---|---|---|---|
| 434. | 1-[2-(4-Benzyl-4-hydroxy-piperidin-1-yl)-ethyl]-3-[2-(benzyl-methyl-amino)-pyridin-4-yl]-urea | 0.74 | 474.2 |
| 435. | 1-[2-(4-Benzyl-4-hydroxy-piperidin-1-yl)-ethyl]-3-[2-(benzyl-methyl-amino)-6-methyl-pyridin-4-yl]-urea | 0.69 | 488.4 |
| 436. | 1-[2-(Benzyl-methyl-amino)-6-methyl-pyridin-4-yl]-3-[2-(4-benzyl-piperidin-1-yl)-ethyl]-urea | 0.75 | 472.27 |
| 437. | 1-[2-(Benzyl-methyl-amino)-pyridin-4-yl]-3-[2-(4-benzyl-piperidin-1-yl)-ethyl]-urea | 0.73 | 458.24 |
| 438. | 1-[2-(4-Benzyl-piperidin-1-yl)-ethyl]-3-[2-(methyl-phenyl-amino)-pyridin-4-yl]-urea | 0.78 | 444.26 |
| 439. | 1-[2-(4-Benzyl-piperidin-1-yl)-ethyl]-3-(2-pyrrolidin-1-yl-pyridin-4-yl)-urea | 0.76 | 408.10 |
| 440. | 1-[2-(Benzyl-phenethyl-amino)-pyridin-4-yl]-3-[2-(4-benzyl-piperidin-1-yl)-ethyl]-urea | 0.76 | 548.16 |
| 441. | 1-[2-(4-Benzyl-4-hydroxy-piperidin-1-yl)-ethyl]-3-(2-dimethylamino-pyridin-4-yl)-urea | 0.68 | 398.26 |
| 442. | 1-[2-(4-Benzyl-piperidin-1-yl)-ethyl]-3-(2-dimethylamino-pyridin-4-yl)-urea | 0.72 | 382.29 |
| 443. | 1-[2-(Benzyl-ethyl-amino)-pyridin-4-yl]-3-[2-(4-benzyl-4-hydroxy-piperidin-1-yl)-ethyl]-urea | 0.67 | 488.46 |
| 444. | 1-[2-(4-Benzyl-4-hydroxy-piperidin-1-yl)-ethyl]-3-[2-(ethyl-methyl-amino)-pyridin-4-yl]-urea | 0.70 | 412.24 |
| 445. | 1-[2-(4-Benzyl-4-hydroxy-piperidin-1-yl)-ethyl]-3-(2-diallylamino-pyridin-4-yl)-urea | 0.68 | 488.40 |
| 446. | 1-[2-(4-Benzyl-4-hydroxy-piperidin-1-yl)-ethyl]-3-(2-dipropylamino-pyridin-4-yl)-urea | 0.69 | 480.45 |

Example 447

1-[2-(4-Benzyl-4-hydroxy-piperidin-1-yl)-ethyl]-3-(2-methylamino-pyridin-4-yl)-urea

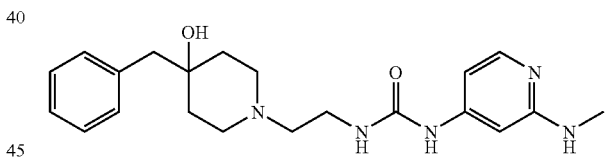

A suspension of 1-[2-(4-benzyl-4-hydroxy-piperidin-1-yl)-ethyl]-3-[2-(benzyl-methyl-amino)-pyridin-4-yl]-urea (Example 434., 0.3 g, 0.65 mmol), 2N aqueous HCl (0.65 mL, 1.3 mmol) and Pd—C 10% (30 mg) in MeOH (20 mL) is stirred under hydrogen atmosphere for 96 h. The catalyst is filtered off and the reaction mixture evaporated to provide the title compound.

The following compounds are prepared in an analogous fashion.

| Example | | $t_r$ | MS (ES+) |
|---|---|---|---|
| 447. | 1-[2-(4-Benzyl-4-hydroxy-piperidin-1-yl)-ethyl]-3-(2-methylamino-pyridin-4-yl)-urea | 0.69 | 384.16 |
| 448. | 1-[2-(4-Benzyl-piperidin-1-yl)-ethyl]-3-(2-methylamino-pyridin-4-yl)-urea | 0.72 | 368.17 |

Example 449

1-(2-Amino-pyridin-4-yl)-3-[2-(4-benzyl-4-hydroxy-piperidin-1-yl)-ethyl]-urea

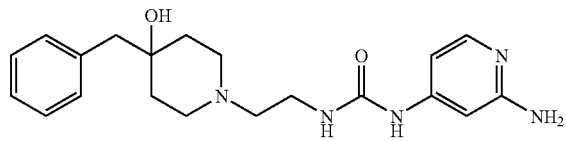

The compound is prepared from 1-[2-(4-benzyl-4-hydroxy-piperidin-1-yl)-ethyl]-3-(2-diallylamino-pyridin-4-yl)-urea (Example 445.) using the method described in Laguzza B. C., Ganem B., "A new protecting group for amines. Synthesis of Anticapsin from L-Tyrosine", Tetrahedron Lett. (1981) 22, 1483-1486.

| Example | | $t_r$ | MS (ES+) |
|---|---|---|---|
| 449. | 1-(2-Amino-pyridin-4-yl)-3-[2-(4-benzyl-4-hydroxy-piperidin-1-yl)-ethyl]-urea | 0.65 | 450.42 |

Example 450

In Vitro Biological Characterization

The inhibitory activity of the compounds of general formula 1 on the actions of urotensin II can be demonstrated using the test procedures described hereinafter:

1) Inhibition of Human [$^{125}$I]-Urotensin II Binding to a Rhabdomyosarcoma Cell Line Whole cell binding of human [$^{125}$I]-urotensin II is performed using human-derived TE-671 rhabdomyosarcoma cells (Deutsche Sammlung von Mikroorganismen und Zellkulturen, cell line #ACC-263), by methods adapted from a whole cell endothelin binding assay (Breu V et al, In vitro characterization of Ro-46-2005, a novel synthetic non-peptide antagonist of ET$_A$ and ET$_B$ receptors. FEBS Lett. 1993, 334, 210-214).

The assay is performed in 250 µL Dulbecco's Modified Eagle Medium, pH 7.4 (GIBCO BRL, CatNo 31885-023), including 25 mM HEPES (Fluka, CatNo 05473), 1.0% DMSO (Fluka, CatNo 41644) and 0.5% (w/v) BSA Fraction V (Fluka, CatNo 05473) in polypropylene microtiter plates (Nunc, CatNo 442587). 300'000 suspended cells are incubated with gentle shaking for 4 h at 20° C. with 20 pM human [$^{125}$I]Urotensin II (Anawa Trading SA, Wangen, Switzerland, 2130Ci/mmol) and increasing concentrations of unlabeled antagonist. Minimum and maximum binding are derived from samples with and without 100 nM unlabelled U-II, respectively. After the 4 h incubation period, the cells are filtered onto GF/C filterplates (Packard, CatNo 6005174). The filter plates are dried, and then 50 µL scintillation cocktail (Packard, MicroScint 20, CatNo 6013621) is added to each well. The filterplates are counted in a microplate counter (Packard Bioscience, TopCount NXT).

All test compounds are dissolved and diluted in 100% DMSO. A ten-fold dilution into assay buffer is performed prior to addition to the assay. The final concentration of DMSO in the assay is 1.0%, which is found not to interfere with the binding. IC50 values are defined as the concentration of antagonist inhibiting 50% of the specific binding of [$^{125}$I]human U-II. Specific binding is the difference between maximum binding and minimum binding, as described above. An IC$_{50}$ value of 0.206 nM is found for unlabeled human U-II. The compounds of the invention are found to have IC$_{50}$ values ranging from 0.1 to 1000 nM in this assay.

2) Inhibition of Human Urotensin II-Induced Contractions on Isolated Rat Thoracic Aorta:

Adult Wistar rats are anesthetized and exsanguinated. The proximal thoracic descending aorta is excised, dissected and a 3-5 mm ring is isolated. The endothelium is removed by gentle rubbing of the intimal surface. The ring is suspended in a 10 mL isolated organ bath filled with Krebs-Henseleit solution (in mM; NaCl 115, KCl 4.7, MgSO$_4$ 1.2, KH$_2$PO$_4$ 1.5, NaHCO$_3$ 25, CaCl$_2$ 2.5, glucose 10) kept at 37° C. and aerated with 95% O$_2$ and 5% CO$_2$. Indomethacin (10$^{-5}$ M) is added to the Krebs-Henseleit solution to avoid eicosanoid generation. The ring is stretched to a resting tension of 1 g. Changes of isometric force are measured using force transducers (EMKA Technologies SA, Paris, France). Following an equilibration period, the rings are briefly contracted with KCl (60 mM). Cumulative doses of human urotensin II(10$^{-12}$ M to 10$^{-6}$ M) are added after a 10 min incubation with the test compound or its vehicle. Functional antagonism is measured as the inhibition of maximal contraction to urotensin II.

The invention claimed is:
1. A compound of general formula 1,

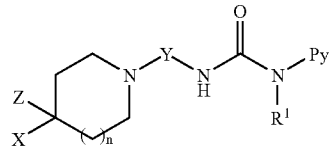

General Formula 1 wherein:
Py represents pyridin-4-yl mono-substituted in position 2 with —NR$^2$R$^3$; pyridin-4-yl disubstituted in position 2 with —NR$^2$R$^3$ and in position 6 with lower alkyl or arylalkyl; unsubstituted quinolin-4-yl; quinolin-4-yl mono-substituted in position 2 with lower alkyl; quinolin-4-yl di-substituted in position 2 with lower alkyl and in position 6, 7, or 8 with halogen, lower alkyl, or arylalkyl; 2-hydroxymethyl-quinolin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; or 1-benzyl-2,3-dihydro-1H-pyrrolo[2,3-b]pyridin-4-yl;

X represents aryl; aryl-O—; arylalkyl-; lower alkyl-SO$_2$NR$^2$—; aryl-SO$_2$NR$^2$—; arylalkyl-SO$_2$NR$^2$—; lower alkyl-CONR$^2$—; aryl-CONR$^2$—; arylalkyl-CONR$^2$—; lower alkyl-NR$^3$CONR$^2$—; aryl-NR$^3$CONR$^2$—; arylalkyl-NR$^3$CONR$^2$—; aryl-CO—; arylalkyl-CO—; lower alkyl-NR$^2$CO—;aryl-NR$^2$CO—; or arylalkyl-NR$^2$CO—;

Y represents —C(R$^4$)(R$^5$)(CH$_2$)$_m$— or —(CH$_2$)$_m$C(R$^4$)(R$^5$)—;

Z represents hydrogen; in case X represents aryl or arylalkyl, Z represents hydrogen, hydroxyl, carboxyl, aryl-CONR²—, lower alkyl-NR²CO—, aryl-NR²CO— or arylalkyl-NR²CO—;

n represents the number 0 or 1;

m represents the number 1 or 2;

R¹ represents hydrogen or lower alkyl;

R² and R³ represent independently hydrogen, lower alkyl, or arylalkyl; in case R² and R³ are attached to the same nitrogen atom, R² and R³ together form with the nitrogen to which they are attached, a piperidine, pyrrolidine or morpholine ring;

R⁴ represents hydrogen, lower alkyl, aryl, arylalkyl, or forms together with R⁵ a 3-, 4-, 5-, or 6-membered saturated carbocyclic ring including the carbon atom to which R⁴ and R⁵ are attached as ring atoms; and R⁵ represents hydrogen, methyl, or forms together with R⁴ a 3-, 4-, 5-, or 6-membered saturated carbocyclic ring including the carbon atom to which R⁴ and R⁵ are attached as ring atoms, or an optically pure enantiomer or diastereomer, a mixture of enantiomers or diastereomers, a diastereomeric racemate, and a mixture of diastereomeric racemates; or a pharmaceutically acceptable salt, of said compound.

2. A compound of general formula 2,

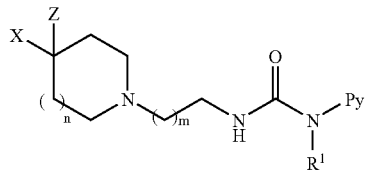

General Formula 2 wherein:

Py represents 2-(benzyl-methyl-amino)-pyridin-4-yl; 2-(benzyl-methyl-amino)-6-methyl-pyridin-4-yl; 2-(benzylamino)-pyridin-4-yl; 2-benzylamino-6-methyl-pyridin-4-yl; 2-(dimethylamino)-pyridin-4-yl; 2-(dimethylamino)-6-methyl-pyridin-4-yl; 2-(methylamino)-pyridin-4-yl; 2-(methylamino)-6-methyl-pyridin-4-yl; 2-aminopyridin-4-yl; 2-amino-6-methyl-pyridin-4-yl; 2-(pyrrolidin-1-yl)-pyridin-4-yl; quinol-4-yl; 2-methylquinol-4-yl; 2-cyclopropylquinol-4-yl; 8-benzyl-2-methyl-quinol-4-yl; [1,8]naphthyridin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; or 1-benzyl-2,3-dihydro-1H-pyrrolo[2,3-b]pyridin-4-yl;

X represents aryl; aryl-O—; arylalkyl-; lower alkyl-SO₂NR²—; aryl-SO₂NR²—; arylalkyl-SO₂NR²—; lower alkyl-CONR²—; aryl-CONR²—; arylalkyl-CONR²—; lower alkyl-NR³CONR²—; aryl-NR³CONR²—; arylalkyl-NR³CONR²—; aryl-CO—; arylalkyl-CO—; lower alkyl-NR²CO—; aryl-NR²CO—; or arylalkyl-NR²CO—;

Z represents hydrogen; in case X represents aryl or arylalkyl, Z represents hydrogen or hydroxyl;

n represents the number 0 or 1;

m represents the number 1 or 2;

R¹ represents hydrogen or lower alkyl; and

R² and R³ represent independently hydrogen, lower alkyl, or arylalkyl, or a pharmaceutically acceptable salt of said compound.

3. A compound of general formula 3,

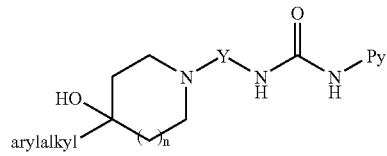

General formula 3 wherein:

Py represents pyridin-4-yl mono-substituted in position 2 with —NR²R³; pyridin-4-yl disubstituted in position 2 with —NR²R³ and in position 6 with lower alkyl or arylalkyl; unsubstituted quinolin-4-yl; quinolin-4-yl mono-substituted in position 2 with lower alkyl; quinolin-4-yl di-substituted in position 2 with lower alkyl and in position 6, 7, or 8 with halogen, lower alkyl, or arylalkyl; 2-hydroxymethyl-quinolin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; or 1-benzyl-2,3-dihydro-1H-pyrrolo[2,3-b]pyridin-4-yl;

Y represents —C(R⁴)(R⁵)(CH₂)ₘ— or —(CH₂)ₘC(R⁴)(R⁵)—;

n represents the number 0 or 1;

m represents the number 1 or 2;

R² and R³ represent independently hydrogen, lower alkyl, or arylalkyl; in case R² and R³ are attached to the same nitrogen atom, R² and R³ together form with the nitrogen to which they are attached, a piperidine, pyrrolidine or morpholine ring;

R⁴ represents hydrogen, lower alkyl, aryl, arylalkyl, or forms together with R⁵ a 3-, 4-, 5-, or 6-membered saturated carbocyclic ring including the carbon atom to which R⁴ and R⁵ are attached as ring atoms; and R⁵ represents hydrogen, methyl, or forms together with R⁴ a 3-, 4-, 5-, or 6-membered saturated carbocyclic ring including the carbon atom to which R⁴ and R⁵ are attached as ring atoms, or a pharmaceutically acceptable salt of said compound.

4. A compound of general formula 4,

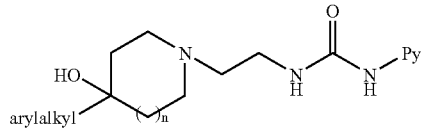

General formula 4 wherein:

Py represents 2-(benzyl-methyl-amino)-pyridin-4-yl; 2-(benzyl-methyl-amino)-6-methyl-pyridin-4-yl; 2-(benzylamino)-pyridin-4-yl; 2-benzylamino-6-methyl-pyridin-4-yl; 2-(dimethylamino)-pyridin-4-yl; 2-(dimethylamino)-6-methyl-pyridin-4-yl; 2-(methylamino)-pyridin-4-yl; 2-(methylamino)-6-methyl-pyridin-4-yl; 2-aminopyridin-4-yl; 2-amino-6-methyl-pyridin-4-yl; 2-(pyrrolidin-1-yl)-pyridin-4-yl; quinol-4-yl; 2-methylquinol-4-yl; 2-cyclopropylquinol-4-yl; 8-benzyl-2-methyl-quinol-4-yl; [1,8]naphthyridin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8] naphthyridin-4-yl; 8-methyl-5,6,7,8-tetrahydro-[1,8] naphthyridin-4-yl; 2,3-dihydro-1H-pyrrolo[2,3-b] pyridin-4-yl; 1-methyl-2,3-dihydro-1H-pyrrolo[2,3-b] pyridin-4-yl; or 1-benzyl-2,3-dihydro-1H-pyrrolo[2,3-b]pyridin-4-yl;

n represents the number 0 or 1, or a pharmaceutically acceptable salt of said compound.

5. A compound of general formula 5,

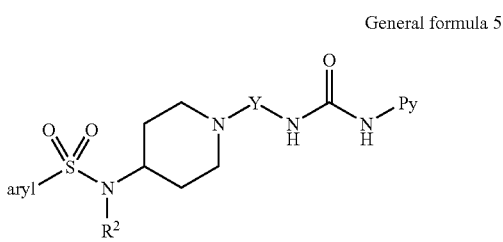

General formula 5 wherein:

Py represents pyridin-4-yl mono-substituted in position 2 with —NR²R³; pyridin-4-yl disubstituted in position 2 with —NR²R³ and in position 6 with lower alkyl or arylalkyl; unsubstituted quinolin-4-yl; quinolin-4-yl mono-substituted in position 2 with lower alkyl; quinolin-4-yl di-substituted in position 2 with lower alkyl and in position 6, 7, or 8 with halogen, lower alkyl, or arylalkyl; 2-hydroxymethyl-quinolin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8] naphthyridin-4-yl; 2,3-dihydro-1H-pyrrolo[2,3-b] pyridin-4-yl; 1-methyl-2,3-dihydro-1H-pyrrolo[2,3-b] pyridin-4-yl; or 1-benzyl-2,3-dihydro-1H-pyrrolo[2,3-b]pyridin-4-yl;

Y represents —C(R⁴)(R⁵)(CH₂)ₘ— or —(CH₂)ₘC(R⁴)(R⁵)—;

m represents the number 1 or 2;

R² and R³ represent independently hydrogen, lower alkyl, or arylalkyl; in case R² and R³ are attached to the same nitrogen atom, R² and R³ together form with the nitrogen to which they are attached, a piperidine, pyrrolidine or morpholine ring;

R⁴ represents hydrogen, lower alkyl, aryl, arylalkyl, or forms together with R⁵ a 3-, 4-, 5-, or 6-membered saturated carbocyclic ring including the carbon atom to which R⁴ and R⁵ are attached as ring atoms; and R⁵ represents hydrogen, methyl, or forms together with R⁴ a 3-, 4-, 5-, or 6-membered saturated carbocyclic ring including the carbon atom to which R⁴ and R⁵ are attached as ring atoms, or a pharmaceutically acceptable salt of said compound.

6. A compound of general formula 6,

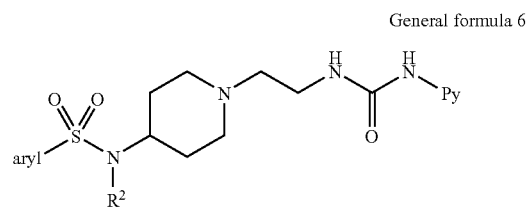

General formula 6 wherein:

Py represents 2-(benzyl-methyl-amino)-pyridin-4-yl; 2-(benzyl-methyl-amino)-6-methyl-pyridin-4-yl; 2-(benzylamino)-pyridin-4-yl; 2-benzylamino-6-methyl-pyridin-4-yl; 2-(dimethylamino)-pyridin-4-yl; 2-(dimethylamino)-6-methyl-pyridin-4-yl; 2-(methylamino)-pyridin-4-yl; 2-(methylamino)-6-methyl-pyridin-4-yl; 2-aminopyridin-4-yl; 2-amino-6-methyl-pyridin-4-yl; 2-(pyrrolidin-1-yl)-pyridin-4-yl; quinol-4-yl; 2-methylquinol-4-yl; 2-cyclopropylquinol-4-yl; 8-benzyl-2-methyl-quinol-4-yl; [1,8]naphthyridin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; or 1-benzyl-2,3-dihydro-1H-pyrrolo[2,3-b]pyridin-4-yl;

R² represents hydrogen or lower alkyl, or arylalkyl, or a pharmaceutically acceptable salt of said compound.

7. A compound of general formula 7,

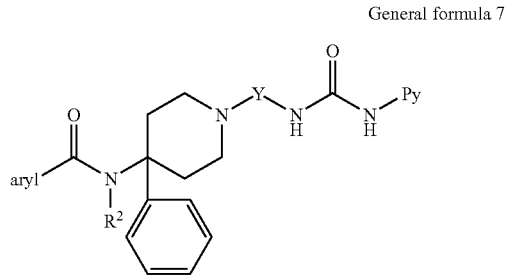

General formula 7 wherein:

Py represents pyridin-4-yl mono-substituted in position 2 with —NR²R³; pyridin-4-yl disubstituted in position 2 with —NR²R³ and in position 6 with lower alkyl or arylalkyl; unsubstituted quinolin-4-yl; quinolin-4-yl mono-substituted in position 2 with lower alkyl; quinolin-4-yl di-substituted in position 2 with lower alkyl and in position 6, 7, or 8 with halogen, lower alkyl, or arylalkyl; 2-hydroxymethyl-quinolin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8] naphthyridin-4-yl; 2,3-dihydro-1H-pyrrolo[2,3-b] pyridin-4-yl; 1-methyl-2,3-dihydro-1H-pyrrolo[2,3-b] pyridin-4-yl; or 1-benzyl-2,3-dihydro-1H-pyrrolo[2,3-b]pyridin-4-yl;

Y represents —C(R⁴)(R⁵)(CH₂)ₘ— or —(CH₂)ₘC(R⁴)(R⁵)—;

m represents the number 1 or 2;

$R^2$ and $R^3$ represent independently hydrogen, lower alkyl, or arylalkyl; in case $R^2$ and $R^3$ are attached to the same nitrogen atom, $R^2$ and $R^3$ together form with the nitrogen to which they are attached, a piperidine, pyrrolidine or morpholine ring;

$R^4$ represents hydrogen, lower alkyl, aryl, arylalkyl, or forms together with $R^5$ a 3-, 4-, 5-, or 6-membered saturated carbocyclic ring including the carbon atom to which $R^4$ and $R^5$ are attached as ring atoms; and $R^5$ represents hydrogen, methyl, or forms together with $R^4$ a 3-, 4-, 5-, or 6-membered saturated carbocyclic ring including the carbon atom to which $R^4$ and $R^5$ are attached as ring atoms, or a pharmaceutically acceptable salt of said compound.

8. A compound of general formula 8,

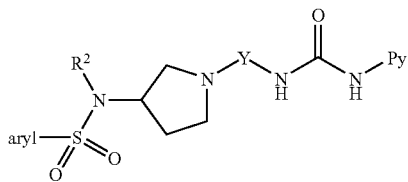

General formula 8 wherein:

Py represents pyridin-4-yl mono-substituted in position 2 with —NR²R³; pyridin-4-yl disubstituted in position 2 with —NR²R³ and in position 6 with lower alkyl or arylalkyl; unsubstituted quinolin-4-yl; quinolin-4-yl mono-substituted in position 2 with lower alkyl; quinolin-4-yl di-substituted in position 2 with lower alkyl and in position 6, 7, or 8 with halogen, lower alkyl, or arylalkyl; 2-hydroxymethyl-quinolin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; or 1-benzyl-2,3-dihydro-1H-pyrrolo[2,3-b]pyridin-4-yl;

Y represents —C(R⁴)(R⁵)(CH₂)ₘ— or —(CH₂)ₘC(R⁴)(R⁵)—;

m represents the number 1 or 2;

$R^2$ and $R^3$ represent independently hydrogen, lower alkyl, or arylalkyl; in case $R^2$ and $R^3$ are attached to the same nitrogen atom, $R^2$ and $R^3$ together form with the nitrogen to which they are attached, a piperidine, pyrrolidine or morpholine ring;

$R^4$ represents hydrogen, lower alkyl, aryl, arylalkyl, or forms together with $R^5$ a 3-, 4-, 5-, or 6-membered saturated carbocyclic ring including the carbon atom to which $R^4$ and $R^5$ are attached as ring atoms; and $R^5$ represents hydrogen, methyl, or forms together with $R^4$ a 3-, 4-, 5-, or 6-membered saturated carbocyclic ring including the carbon atom to which $R^4$ and $R^5$ are attached as ring atoms, or a pharmaceutically acceptable salt of said compound.

9. A compound of general formula 9,

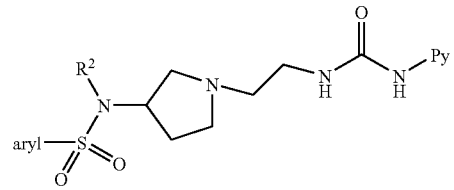

General formula 9 wherein:

Py represents 2-(benzyl-methyl-amino)-pyridin-4-yl; 2-(benzyl-methyl-amino)-6-methyl-pyridin-4-yl; 2-(benzylamino)-pyridin-4-yl; 2-benzylamino-6-methyl-pyridin-4-yl; 2-(dimethylamino)-pyridin-4-yl; 2-(dimethylamino)-6-methyl-pyridin-4-yl; 2-(methylamino)-pyridin-4-yl; 2-(methylamino)-6-methyl-pyridin-4-yl; 2-aminopyridin-4-yl; 2-amino-6-methyl-pyridin-4-yl; 2-(pyrrolidin-1-yl)-pyridin-4-yl; quinol-4-yl; 2-methylquinol-4-yl; 2-cyclopropylquinol-4-yl; 8-benzyl-2-methyl-quinol-4-yl; [1,8]naphthyridin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; or 1-benzyl-2,3-dihydro-1H-pyrrolo[2,3-b]pyridin-4-yl; and $R^2$ represents hydrogen or lower alkyl, or arylalkyl, or a pharmaceutically acceptable salt of said compound.

10. A compound of general formula 10,

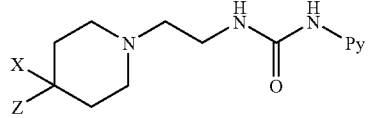

General formula 10 wherein:

Py represents pyridin-4-yl mono-substituted in position 2 with —NR²R³; pyridin-4-yl disubstituted in position 2 with —NR²R³ and in position 6 with lower alkyl or arylalkyl; unsubstituted quinolin-4-yl; quinolin-4-yl mono-substituted in position 2 with lower alkyl; quinolin-4-yl di-substituted in position 2 with lower alkyl and in position 6, 7, or 8 with halogen, lower alkyl, or arylalkyl; 2-hydroxymethyl-quinolin-4-yl; 7-methyl-[1,8]naphthyridin-4-yl; 5,6,7,8-tetrahydro-[1,8]naphthyridin-4-yl; 8-benzyl-5,6,7,8-tetrahydro-[1,8]naphthyridin-4-yl; 8-methyl-5,6,7,8-tetrahydro-[1,8]naphthyridin-4-yl; 2,3-dihydro-1H-pyrrolo[2,3-b]pyridin-4-yl; 1-methyl-2,3-dihydro-1H-pyrrolo[2,3-b]pyridin-4-yl; or 1-benzyl-2,3-dihydro-1H-pyrrolo[2,3-b]pyridin-4-yl;

X represents aryl; aryl-O—; arylalkyl-; lower alkyl-SO₂NR²—; aryl-SO₂NR²—; arylalkyl-SO₂NR²—; lower alkyl-CONR²—; aryl-CONR²—; arylalkyl-CONR²—; lower alkyl-NR³CONR²—; aryl-NR³CONR²—; arylalkyl-NR³CONR²—; aryl-CO—; arylalkyl-CO—; lower alkyl-NR²CO—; aryl-NR²CO—; or arylalkyl-NR²CO—;

Z represents hydrogen; in case X represents aryl or arylalkyl, Z represents hydrogen, hydroxyl, carboxyl, aryl-CONR$^2$—, lower alkyl-NR$^2$CO—, aryl-NR$^2$CO— or arylalkyl-NR$^2$CO—; and R$^2$ and R$^3$ represent independently hydrogen, lower alkyl, or arylalkyl; in case R$^2$ and R$^3$ are attached to the same nitrogen atom, R$^2$ and R$^3$ together form with the nitrogen to which they are attached, a piperidine, pyrrolidine or morpholine ring, or a pharmaceutically acceptable salt of said compound.

11. A compound of general formula 11,

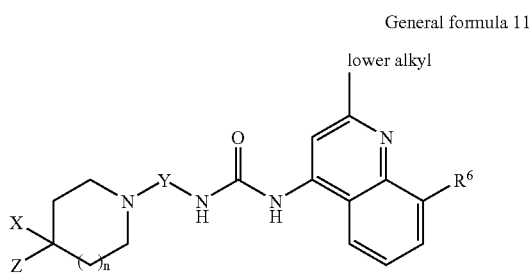

General formula 11 wherein:

R$^6$ is hydrogen, lower alkyl, or arylalkyl;

X represents aryl; aryl-O—; arylalkyl-; lower alkyl-SO$_2$NR$^2$—; aryl-SO$_2$NR$^2$—; arylalkyl-SO$_2$NR$^2$—; lower alkyl-CONR$^2$—; aryl-CONR$^2$—; arylalkyl-CONR$^2$—; lower alkyl-NR$^3$CONR$^2$—; aryl-NR$^3$CONR$^2$—; arylalkyl-NR$^3$CONR$^2$—; aryl-CO—; arylalkyl-CO—; lower alkyl-NR$^2$CO—; aryl-NR$^2$CO—; or arylalkyl-NR$^2$CO—;

Y represents —C(R$^4$)(R$^5$)(CH$_2$)$_m$— or —(CH$_2$)$_m$C(R$^4$)(R$^5$)—;

Z represents hydrogen; in case X represents aryl or arylalkyl, Z represents hydrogen, hydroxyl, carboxyl, aryl-CONR$^2$—, lower alkyl-NR$^2$CO—, aryl-NR$^2$CO— or arylalkyl-NR$^2$CO—;

n represents the number 0 or 1;

m represents the number 1 or 2;

R$^2$ and R$^3$ represent independently hydrogen, lower alkyl, or arylalkyl; in case R$^2$ and R$^3$ are attached to the same nitrogen atom, R$^2$ and R$^3$ together form with the nitrogen to which they are attached, a piperidine, pyrrolidine or morpholine ring;

R$^4$ represents hydrogen, lower alkyl, aryl, arylalkyl, or forms together with R$^5$ a 3-, 4-, 5-, or 6-membered saturated carbocyclic ring including the carbon atom to which R$^4$ and R$^5$ are attached as ring atoms; and R$^5$ represents hydrogen, methyl, or forms together with R$^4$ a 3-, 4-, 5-, or 6-membered saturated carbocyclic ring including the carbon atom to which R$^4$ and R$^5$ are attached as ring atoms, or a pharmaceutically acceptable salt of said compound.

12. A compound of general formula 12,

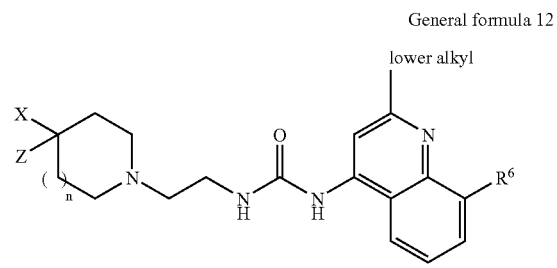

General formula 12 wherein:

R$^6$ represents hydrogen, lower alkyl, or arylalkyl;

X represents aryl; aryl-O—; arylalkyl-; lower alkyl-SO$_2$NR$^2$—; aryl-SO$_2$NR$^2$—; arylalkyl-SO$_2$NR$^2$—; lower alkyl-CONR$^2$—; aryl-CONR$^2$—; arylalkyl-CONR$^2$—; lower alkyl-NR$^3$CONR$^2$—; aryl-NR$^3$CONR$^2$—; arylalkyl-NR$^3$CONR$^2$—; aryl-CO—; arylalkyl-CO—; lower alkyl-NR$^2$CO—; aryl-NR$^2$CO—; or arylalkyl-NR$^2$CO—;

Z represents hydrogen; in case X represents aryl or arylalkyl, Z represents hydrogen, or hydroxyl;

n represents the number 0 or 1; and

R$^2$ and R$^3$ represent independently hydrogen, lower alkyl, or arylalkyl, or a pharmaceutically acceptable salt of said compound.

13. A compound of general formula 13,

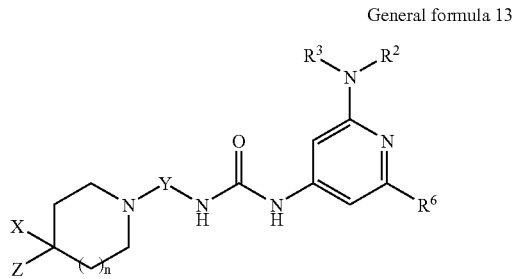

General formula 13 wherein:

R$^6$ represents hydrogen, lower alkyl, or arylalkyl;

X represents aryl; aryl-O—; arylalkyl-; lower alkyl-SO$_2$NR$^2$—; aryl-SO$_2$NR$^2$—; arylalkyl-SO$_2$NR$^2$—; lower alkyl-CONR$^2$—; aryl-CONR$^2$—; arylalkyl-CONR$^2$—; lower alkyl-NR$^3$CONR$^2$—; aryl-NR$^3$CONR$^2$—; arylalkyl-NR$^3$CONR$^2$—; aryl-CO—; arylalkyl-CO—; lower alkyl-NR$^2$CO—;aryl-NR$^2$CO—; or arylalkyl-NR$^2$CO—;

Y represents —C(R$^4$)(R$^5$)(CH$_2$)$_m$— or —(CH$_2$)$_m$C(R$^4$)(R$^5$)—;

Z represents hydrogen; in case X represents aryl or arylalkyl, Z represents hydrogen, hydroxyl, carboxyl, aryl-CONR$^2$—, lower alkyl-NR$^2$CO—, aryl-NR$^2$CO— or arylalkyl-NR$^2$CO—;

n represents the number 0 or 1;

m represents the number 1 or 2;

R$^2$ and R$^3$ represent independently hydrogen, lower alkyl, or arylalkyl; in case R$^2$ and R$^3$ are attached to the same nitrogen atom, R$^2$ and R$^3$ together form with the nitrogen to which they are attached, a piperidine, pyrrolidine or morpholine ring;

$R^4$ represents hydrogen, lower alkyl, aryl, arylalkyl, or forms together with $R^5$ a 3-, 4-, 5-, or 6-membered saturated carbocyclic ring including the carbon atom to which $R^4$ and $R^5$ are attached as ring atoms; and $R^5$ represents hydrogen, methyl, or forms together with $R^4$ a 3-, 4-, 5-, or 6-membered saturated carbocyclic ring including the carbon atom to which $R^4$ and $R^5$ are attached as ring atoms, or a pharmaceutically acceptable salt of said compound.

14. A compound of general formula 14,

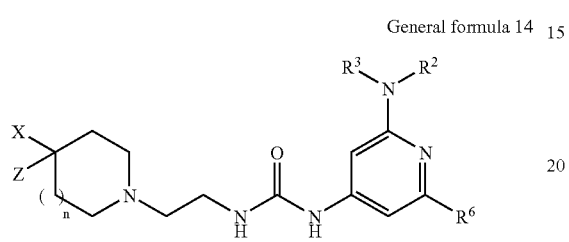

General formula 14 wherein:

$R^6$ represents hydrogen, lower alkyl, or arylalkyl;

X represents aryl; aryl-O—; arylalkyl-; lower alkyl-SO$_2$NR$^2$—; aryl-SO$_2$NR$^2$—; arylalkyl-SO$_2$NR$^2$—; lower alkyl-CONR$^2$—; aryl-CONR$^2$—; arylalkyl-CONR$^2$—; lower alkyl-NR$^3$CONR$^2$—; aryl-NR$^3$CONR$^2$—; arylalkyl-NR$^3$CONR$^2$—; aryl-CO—; arylalkyl-CO—; lower alkyl-NR$^2$CO—; aryl-NR$^2$CO—; or arylalkyl-NR$^2$CO—;

Z represents hydrogen; in case X represents aryl or arylalkyl, Z represents hydrogen, hydroxyl, carboxyl, aryl-CONR$^2$—, lower alkyl-NR$^2$CO—, aryl-NR$^2$CO— or arylalkyl-NR$^2$CO—;

n represents the number 0 or 1; and $R^2$ and $R^3$ represent independently hydrogen, lower alkyl, or arylalkyl; in case $R^2$ and $R^3$ are attached to the same nitrogen atom, $R^2$ and $R^3$ together form with the nitrogen to which they are attached, a piperidine, pyrrolidine or morpholine ring, or a pharmaceutically acceptable salt of said compound.

15. A compound of general formula 15,

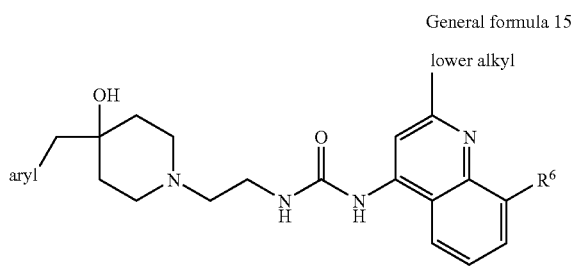

General formula 15 wherein $R^6$ represents hydrogen, lower alkyl, or arylalkyl, or a pharmaceutically acceptable salt of said compound.

16. A compound of general formula 16,

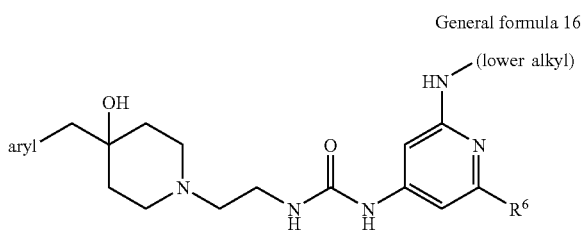

General formula 16 wherein $R^6$ represents hydrogen, lower alkyl, or arylalkyl, or a pharmaceutically acceptable salt of said compound.

17. A compound of general formula 17,

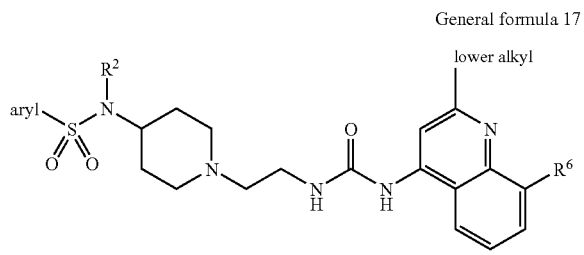

General formula 17 wherein $R^6$ and $R^2$ represent independently hydrogen, lower alkyl, or arylalkyl, or a pharmaceutically acceptable salt of said compound.

18. A compound of general formula 18,

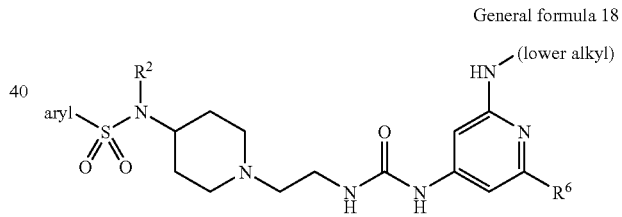

General formula 18 wherein $R^6$ and $R^2$ represent independently hydrogen, lower alkyl, or arylalkyl, or a pharmaceutically acceptable salt of said compound.

19. A compound of general formula 19,

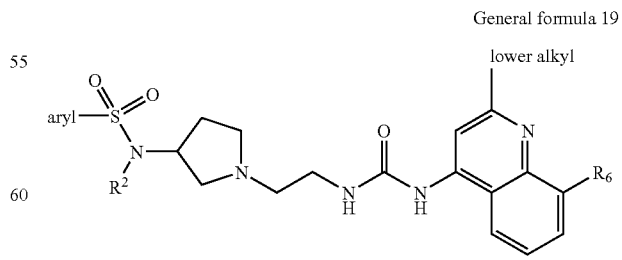

General formula 19 wherein $R^6$ and $R^2$ represent independently hydrogen, lower alkyl, or arylalkyl;

or a pharmaceutically acceptable salt of said compound.

20. A compound of general formula 20,

General formula 20

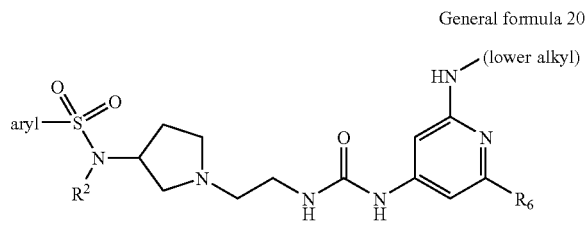

wherein $R^6$ and $R^2$ represent independently hydrogen, lower alkyl, or arylalkyl;

or a pharmaceutically acceptable salt of said compound.

21. The compound according to claim 1 that is selected from the group consisting of N-(1-{2-[3-(2-Methyl-quinolin-4-yl)-ureido]-ethyl}-piperidin-4-yl)-4-trifluoromethyl-benzenesulfonamide;
N-Methyl-N-(1-{2-[3-(2-methyl-quinolin-4-yl)-ureido]-ethyl}-pyrrolidin-3-yl)-benzenesulfonamide;
Thiophene-2-sulfonic acid (1-{2-[3-(2-methyl-quinolin-4-yl)-ureido]-ethyl}-pyrrolidin-3-yl)-amide; p1 3-Methyl-N-(1-{2-[3-(2-methyl-quinolin-4-yl)-ureido]-ethyl}-pyrrolidin-3-yl)-benzenesulfonamide;
3,N-Dimethyl-N-(1-{2-[3-(2-methyl-quinolin-4-yl)-ureido]-ethyl}-pyrrolidin-3-yl)-benzenesulfonamide;
2-Methyl-N-(1-{2-[3-(2-methyl-quinolin-4-yl)-ureido]-ethyl}-pyrrolidin-3-yl)-benzenesulfonamide;
2,N-Dimethyl-N-(1-{2-[3-(2-methyl-quinolin-4-yl)-ureido]-ethyl}-pyrrolidin-3-yl)-benzenesulfonamide;
4-Methyl-N-(1-{2-[3-(2-methyl-quinolin-4-yl)-ureido]-ethyl}-piperidin-4-yl)-benzenesulfonamide;
4-Methyl-N-(1-{2-[3-(2-methyl-quinolin-4-yl)-ureido]-ethyl}-pyrrolidin-3-yl)-benzenesulfonamide;
4,N-Dimethyl-N-(1-{2-[3-(2-methyl-quinolin-4-yl)-ureido]-ethyl}-pyrrolidin-3-yl)-benzenesulfonamide;
2-Fluoro-N-(1-{2-[3-(2-methyl-quinolin-4-yl)-ureido]-ethyl}-pyrrolidin-3-yl)-benzenesulfonamide;
2-Fluoro-N-methyl-N-(1-{2-[3-(2-methyl-quinolin-4-yl)-ureido]-ethyl}-pyrrolidin-3-yl)-benzenesulfonamide;
3-Fluoro-N-methyl-N-(1-{2-[3-(2-methyl-quinolin-4-yl)-ureido]-ethyl}-pyrrolidin-3-yl)-benzenesulfonamide;
4-Fluoro-N-methyl-N-(1-{2-[3-(2-methyl-quinolin-4-yl)-ureido]-ethyl}-pyrrolidin-3-yl)-benzenesulfonamide;
4-Cyano-N-(1-{2-[3-(2-methyl-quinolin-4-yl)-ureido]-ethyl}-piperidin-4-yl)-benzenesulfonamide;
3-Methoxy-N-(1-{2-[3-(2-methyl-quinolin-4-yl)-ureido]-ethyl}-pyrrolidin-3-yl)-benzenesulfonamide;
3-Methoxy-N-methyl-N-(1-{2-[3-(2-methyl-quinolin-4-yl)-ureido]-ethyl}-pyrrolidin-3-yl)-benzenesulfonamide;
4-Methoxy-N-(1-{2-[3-(2-methyl-quinolin-4-yl)-ureido]-ethyl}-piperidin-4-yl)-benzenesulfonamide;
4-Methoxy-N-(1-{2-[3-(2-methyl-quinolin-4-yl)-ureido]-ethyl}-pyrrolidin-3-yl)-benzenesulfonamide;
4-Methoxy-N-methyl-N-(1-{2-[3-(2-methyl-quinolin-4-yl)-ureido]-ethyl}-pyrrolidin-3-yl)-benzenesulfonamide;
3-Chloro-N-(1-{2-[3-(2-methyl-quinolin-4-yl)-ureido]-ethyl}-pyrrolidin-3-yl)-benzenesulfonamide;
3-Chloro-N-methyl-N-(1-{2-[3-(2-methyl-quinolin-4-yl)-ureido]-ethyl}-pyrrolidin-3-yl)-benzenesulfonamide;
4-Chloro-N-(1-{2-[3-(2-methyl-quinolin-4-yl)-ureido]-ethyl}-piperidin-4-yl)-benzenesulfonamide;
4-Chloro-N-(1-{2-[3-(2-methyl-quinolin-4-yl)-ureido]-ethyl}-pyrrolidin-3-yl)-benzenesulfonamide;
2-Chloro-N-(1-{2-[3-(2-methyl-quinolin-4-yl)-ureido]-ethyl}-pyrrolidin-3-yl)-benzenesulfonamide;
Biphenyl-4-sulfonic acid methyl-(1-{2-[3-(2-methyl-quinolin-4-yl)-ureido]-ethyl}-pyrrolidin-3-yl)-amide;
N-(1-{2-[3-(2-Methyl-quinolin-4-yl)-ureido]-ethyl}-pyrrolidin-3-yl)-4-propyl-benzenesulfonamide;
N-Methyl-N-(1-{2-[3-(2-methyl-quinolin-4-yl)-ureido]-ethyl}-pyrrolidin-3-yl)-4-propyl-benzenesulfonamide;
Naphthalene-2-sulfonic acid (1-{2-[3-(2-methyl-quinolin-4-yl)-ureido]-ethyl}-piperidin-4-yl)-amide;
Naphthalene-2-sulfonic acid (1-{2-[3-(2-methyl-quinolin-4-yl)-ureido]-ethyl}-pyrrolidin-3-yl)-amide;
Naphthalene-2-sulfonic acid methyl-(1-{2-[3-(2-methyl-quinolin-4-yl)-ureido]-ethyl}-pyrrolidin-3-yl)-amide;
Naphthalene-1-sulfonic acid (1-{2-[3-(2-methyl-quinolin-4-yl)-ureido]-ethyl}-piperidin-4-yl)-amide;
Naphthalene-1-sulfonic acid (1-{2-[3-(2-methyl-quinolin-4-yl)-ureido]-ethyl}-pyrrolidin-3-yl)-amide;
Naphthalene-1-sulfonic acid methyl-(1-{2-[3-(2-methyl-quinolin-4-yl)-ureido]-ethyl}-pyrrolidin-3-yl)-amide;
Quinoline-8-sulfonic acid (1-{2-[3-(2-methyl-quinolin-4-yl)-ureido]-ethyl}-pyrrolidin-3-yl)-amide;
Quinoline-8-sulfonic acid methyl-(1-{2-[3-(2-methyl-quinolin-4-yl)-ureido]-ethyl}-pyrrolidin-3-yl)-amide;
4-tert-Butyl-N-(1-{2-[3-(2-methyl-quinolin-4-yl)-ureido]-ethyl}-pyrrolidin-3-yl)-benzenesulfonamide;
4-tert-Butyl-N-methyl-N-(1-{2-[3-(2-methyl-quinolin-4-yl)-ureido]-ethyl}-pyrrolidin-3-yl)-benzenesulfonamide;
N-(1-{2-[3-(2-Methyl-quinolin-4-yl)-ureido]-ethyl}-pyrrolidin-3-yl)-4-trifluoromethyl-benzenesulfonamide;
N-Methyl-N-(1-{2-[3-(2-methyl-quinolin-4-yl)-ureido]-ethyl}-pyrrolidin-3-yl)-4-trifluoromethyl-benzenesulfonamide;
N-(1-{2-[3-(2-Methyl-quinolin-4-yl)-ureido]-ethyl}-piperidin-4-yl)-2-trifluoromethyl-benzenesulfonamide;
N-(1-{2-[3-(2-Methyl-quinolin-4-yl)-ureido]-ethyl}-pyrrolidin-3-yl)-2-trifluoromethyl-benzenesulfonamide;
N-Methyl-N-(1-{2-[3-(2-methyl-quinolin-4-yl)-ureido]-ethyl}-pyrrolidin-3-yl)-2-trifluoromethyl-benzenesulfonamide;
N-(1-{2-[3-(2-Methyl-quinolin-4-yl)-ureido]-ethyl}-pyrrolidin-3-yl)-3-trifluoromethyl-benzenesulfonamide;
3,4-Dichloro-N-(1-{2-[3-(2-methyl-quinolin-4-yl)-ureido]-ethyl}-piperidin-4-yl)-benzenesulfonamide;
3,4-Dichloro-N-methyl-N-(1-{2-[3-(2-methyl-quinolin-4-yl)-ureido]-ethyl}-pyrrolidin-3-yl)-benzenesulfonamide;
N-(1-{2-[3-(2-Methyl-quinolin-4-yl)-ureido]-ethyl}piperidin-4-yl)-4-pentyl-benzenesulfonamide;
N-(1-{2-[3-(2-Methyl-quinolin-4-yl)-ureido]-ethyl}pyrrolidin-3-yl)-4-pentyl-benzenesulfonamide;
N-Methyl-N-(1-{2-[3-(2-methyl-quinolin-4-yl)-ureido]-ethyl}-pyrrolidin-3-yl)-4-pentyl-benzenesulfonamide;
4-Butoxy-N-(1-{2-[3-(2-methyl-quinolin-4-yl)-ureido]-ethyl}-pyrrolidin-3-yl)-benzenesulfonamide;
4-Butoxy-N-methyl-N-(1-{2-[3-(2-methyl-quinolin-4-yl)-ureido]-ethyl}-pyrrolidin-3-yl)-benzenesulfonamide;
4,5-Dichloro-thiophene-2-sulfonic acid (1-{2-[3-(2-methyl-quinolin-4-yl)-ureido]-ethyl}-piperidin-4-yl)-amide;
4,5-Dichloro-thiophene-2-sulfonic acid (1-{2-[3-(2-methyl-quinolin-4-yl)-ureido]-ethyl}-pyrrolidin-3-yl)-amide;

4,5-Dichloro-thiophene-2-sulfonic acid methyl-(1-{2-[3-(2-methyl-quinolin-4-yl)-ureido]-ethyl}-pyrrolidin-3-yl)-amide;
4-(3-Chloro-2-cyano-phenoxy)-N-(1-{2-[3-(2-methyl-quinolin-4-yl)-ureido]-ethyl}-piperidin-4-yl)-benzenesulfonamide;
4-(3-Chloro-2-cyano-phenoxy)-N-(1-{2-[3-(2-methyl-quinolin-4-yl)-ureido]-ethyl}-pyrrolidin-3-yl)-benzenesulfonamide;
4-(3-Chloro-2-cyano-phenoxy)-N-methyl-N-(1-{2-[3-(2-methyl-quinolin-4-yl)-ureido]-ethyl}-pyrrolidin-3-yl)-benzenesulfonamide;
N-[4-Methyl-5-(1-{2-[3-(2-methyl-quinolin-4-yl)-ureido]-ethyl}-piperidin-4-ylsulfamoyl)-thiazol-2-yl]-acetamide;
3-Bromo-N-(1-{2-[3-(2-methyl-quinolin-4-yl)-ureido]-ethyl}-piperidin-4-yl)-benzenesulfonamide;
3-Bromo-N-(1-{2-[3-(2-methyl-quinolin-4-yl)-ureido]-ethyl}-pyrrolidin-3-yl)-benzenesulfonamide;
3-Bromo-N-methyl-N-(1-{2-[3-(2-methyl-quinolin-4-yl)-ureido]-ethyl}-pyrrolidin-3-yl)-benzenesulfonamide;
4-Bromo-N-(1-{2-[3-(2-methyl-quinolin-4-yl)-ureido]-ethyl}-piperidin-4-yl)-benzenesulfonamide;
4-Bromo-N-(1-{2-[3-(2-methyl-quinolin-4-yl)-ureido]-ethyl}-pyrrolidin-3-yl)-benzenesulfonamide;
4-Bromo-N-methyl-N-(1-{2-[3-(2-methyl-quinolin-4-yl)-ureido]-ethyl}-pyrrolidin-3-yl)-benzenesulfonamide;
N-(1-{2-[3-(2-Methyl-quinolin-4-yl)-ureido]-ethyl}-pyrrolidin-3-yl)-2-trifluoromethoxy-benzenesulfonamide;
N-(1-{2-[3-(2-Methyl-quinolin-4-yl)-ureido]-ethyl}-piperidin-4-yl)-4-trifluoromethoxy-benzenesulfonamide;
N-(1-{2-[3-(2-Methyl-quinolin-4-yl)-ureido]-ethyl}pyrrolidin-3-yl)-4-trifluoromethoxy-benzenesulfonamide;
N-Methyl-N-(1-{2-[3-(2-methyl-quinolin-4-yl)-ureido]-ethyl}-pyrrolidin-3-yl)-4-trifluoromethoxy-benzenesulfonamide;
5-Dimethylamino-naphthalene-1-sulfonic acid (1-{2-[3-(2-methyl-quinolin-4-yl)-ureido]-ethyl}-piperidin-4-yl)-amide;
5-Dimethylamino-naphthalene-1-sulfonic acid (1-{2-[3-(2-methyl-quinolin-4-yl)-ureido]-ethyl}-pyrrolidin-3-yl)-amide;
5-Dimethylamino-naphthalene-1-sulfonic acid methyl-(1-{2-[3-(2-methyl-quinolin-4-yl)-ureido]-ethyl}-pyrrolidin-3-yl)-amide;
5-Chloro-3-methyl-benzo[b]thiophene-2-sulfonic acid (1-{2-[3-(2-methyl-quinolin-4-yl)-ureido]-ethyl}-piperidin-4-yl)-amide;
5-Chloro-3-methyl-benzo[b]thiophene-2-sulfonic acid (1-{2-[3-(2-methyl-quinolin-4-yl)-ureido]-ethyl}-pyrrolidin-3-yl)-amide;
5-Chloro-3-methyl-benzo[b]thiophene-2-sulfonic acid methyl-(1-{2-[3-(2-methyl-quinolin-4-yl)-ureido]-ethyl}pyrrolidin-3-yl)-amide;
4-Bromo-2-ethyl-N-(1-{2-[3-(2-methyl-quinolin-4-yl)-ureido]-ethyl}-piperidin-4-yl)-benzenesulfonamide;
4-Bromo-2-ethyl-N-(1-{2-[3-(2-methyl-quinolin-4-yl)-ureido]-ethyl}-pyrrolidin-3-yl)-benzenesulfonamide;
4-Bromo-2-ethyl-N-methyl-N-(1-{2-[3-(2-methyl-quinolin-4-yl)-ureido]-ethyl}-pyrrolidin-3-yl)-benzenesulfonamide;
N-[5-(1-{2-[3-(2-Methyl-quinolin-4-yl)-ureido]-ethyl}-piperidin-4-ylsulfamoyl)-thiophen-2-ylmethyl]-benzamide;
N-[5-(1-{2-[3-(2-Methyl-quinolin(4-yl)-ureido]-ethyl}-pyrrolidin-3-ylsulfamoyl)-thiophen-2-ylmethyl]-benzamide;
N-{5-[Methyl-(1-{2-[3-(2-methyl-quinolin-4-yl)-ureido]-ethyl}-pyrrolidin-3-yl)-sulfamoyl]-thiophen-2-ylmethyl}benzamide;
4-Benzenesulfonyl-thiophene-2-sulfonic acid (1-{2-[3-(2-methyl-quinolin-4-yl)-ureido]-ethyl}piperidin-4-yl)-amide;
4-Benzenesulfonyl-thiophene-2-sulfonic acid (1-{2-[3-(2-methyl-quinolin-4-yl)-ureido]-ethyl}-pyrrolidin-3-yl)-amide;
4-Benzenesulfonyl-thiophene-2-sulfonic acid methyl-(1-{2-[3-(2-methyl-quinolin-4-yl)-ureido]-ethyl}pyrrolidin-3-yl)-amide;
2-(2,2,2-Trifluoro-acetyl)-1,2,3,4-tetrahydro-isoquinoline-7-sulfonic acid (1-{2-[3-(2-methyl-quinolin-4-yl)-ureido]-ethyl}piperidin-4-yl)-amide;
2-(2,2,2-Trifluoro-acetyl)-1,2,3,4-tetrahydro-isoquinoline-7-sulfonic acid (1-{2-[3-(2-methyl-quinolin-4-yl)-ureido]-ethyl}-pyrrolidin-3-yl)-amide
2-(2,2,2-Trifluoro-acetyl)-1,2,3,4-tetrahydro-isoquinoline-7-sulfonic acid methyl-(1-{2-[3-(2-methyl-quinolin-4-yl)-ureido]-ethyl}-pyrrolidin-3-yl)-amide;
2-Phenyl-ethanesulfonic acid (1-{2-[3-(2-methyl-quinolin-4-yl)-ureido]-ethyl}-piperidin-4-yl)-amide;
4-Chloro-N-methyl-N-(1-{2-[3-(2-methyl-quinolin-4-yl)-ureido]-ethyl}-pyrrolidin-3-yl)-benzenesulfonamide;
4-Bromo-N-methyl-N-(1-{2-[3-(2-methyl-quinolin-4-yl)-ureido]-ethyl}-piperidin-4-yl)-benzenesulfonamide;
1-{2-[4-(3-Biphenyl-2-yl-ureido)-piperidin-1-yl]-ethyl}-3-(2-methyl-quinolin-4-yl)-urea;
1-{2-[3-(3-Biphenyl-2-yl-ureido)-pyrrolidin-1-yl]-ethyl}-3-(2-methyl-quinolin-4-yl)-urea;
1-(2-{4-[3-(2-Isopropyl-phenyl)-ureido]-piperidin-1-yl}ethyl)-3-(2-methyl-quinolin-4-yl)-urea;
1-(2-{4-[3-(2-Isopropyl-phenyl)-ureido]-pyrrolidin-1-yl]-ethyl)-3-(2-methyl-quinolin-4-yl)-urea;
1-(2-Methyl-quinolin-4-yl)-3-(2-{3-[3-(2-phenoxy-phenyl)-ureido]-pyrrolidin-1-yl]-ethyl)-urea;
N-(1-{2-[3-(2-Methyl-quinolin-4-yl)-ureido]-ethyl}-piperidin-4-yl)-2-naphthalen-1-yl-acetamide;
2-(4-Bromo-phenyl)-N-(1-{2-[3-(2-methyl-quinolin-4-yl)-ureido]-ethyl}-piperidin-4-yl)-acetamide;
4-Benzoyl-N-methyl-N-(1-{2-[3-(2-methyl-quinolin-4-yl)-ureido]-ethyl}-pyrrolidin-3-yl)-benzamide;
1-(2-Methyl-quinolin-4-yl)-3-[2-(4-phenyl-piperidin-1-yl)-ethyl]-urea;
1-(2-Methyl-quinolin-4-yl)-3-[2-(4-o-tolyl-piperidin-1-yl)-ethyl]-urea;
1-[2-(4-Benzyl-4-hydroxy-piperidin-1-yl)-ethyl]-3-(2-methyl-quinolin-4-yl)-urea;
1-[2-(4-Hydroxy-4-phenyl-piperidin-1-yl)-ethyl]-3-(2-methyl-quinolin-4-yl)-urea;
1-[2-(4-Benzyl-piperidin-1-yl)-ethyl]-3-(2-methyl-quinolin-4-yl)-urea; and
1-[2-(Benzyl-methyl-amino)-pyridin-4-yl]-3-[2-(4-benzyl-piperidin-1-yl)-ethyl]-urea,
or a pharmaceutically acceptable salt of said compound.

22. The compound according to claim 1 that is selected from the group consisting of
4-Bromo-N-methyl-N-(1-{2-[3-(2-methyl-quinolin-4-yl)-ureido]-ethyl}-piperidin-4-yl)-benzenesulfonamide;
4-Bromo-N-ethyl-N-(1-{2-[3-(2-methyl-quinolin-4-yl)-ureido]-ethyl}-pyrrolidin-3-yl)-benzenesulfonamide;

4-Bromo-N-(1-{2-[3-(2-methyl-quinolin-4-yl)-ureido]-ethyl}-piperidin-4-yl)-N-propyl-benzenesulfonamide;
4-Bromo-N-(1-{2-[3-(2-methyl-quinolin-4-yl)-ureido]-ethyl}-pyrrolidin-3-yl)-N-propyl-benzenesulfonamide;
4-Bromo-N-isobutyl-N-(1-{2-[3-(2-methyl-quinolin-4-yl)-ureido]-ethyl}-piperidin-4-yl)-benzenesulfonamide;
4-Bromo-N-isobutyl-N-(1-{2-[3-(2-methyl-quinolin-4-yl)-ureido]-ethyl}-pyrrolidin-3-yl)-benzenesulfonamide;
4-Bromo-N-butyl-N-(1-{2-[3-(2-methyl-quinolin-4-yl)-ureido]-ethyl}-piperidin-4-yl)-benzenesulfonamide;
4-Bromo-N-butyl-N-(1-{2-[3-(2-methyl-quinolin-4-yl)-ureido]-ethyl}-pyrrolidin-3-yl)-benzenesulfonamide;
N-Benzyl-4-bromo-N-(1-{2-[3-(2-methyl-quinolin-4-yl)-ureido]-ethyl}-piperidin-4-yl)-benzenesulfonamide;
N-Benzyl-4-bromo-N-(1-{2-[3-(2-methyl-quinolin-4-yl)-ureido]-ethyl}-pyrrolidin-3-yl)-benzenesulfonamide;
4-Bromo-N-(1-{2-[3-(2-methyl-quinolin-4-yl)-ureido]-ethyl}-piperidin-4-yl)-N-phenethyl-benzenesulfonamide;
4-Bromo-N-(1-{2-[3-(2-methyl-quinolin-4-yl)-ureido]-ethyl}-pyrrolidin-3-yl)-N-phenethyl-benzenesulfonamide;
4-Bromo-N-methyl-N-((R)-1-{2-[3-(2-methyl-quinolin-4-yl)-ureido]-ethyl}pyrrolidin-3-yl)-benzenesulfonamide;
4-Bromo-N-ethyl-N-((R)-1-{2-[3-(2-methyl-quinolin-4-yl)-ureido]-ethyl}-pyrrolidin-3-yl)-benzenesulfonamide;
4-Bromo-N-ethyl-N-((S)-1-{2-[3-(2-methyl-quinolin-4-yl)-ureido]-ethyl}-pyrrolidin-3-yl)-benzenesulfonamide;
4-Bromo-N-methyl-N-((S)-1-{2-[3-(2-methyl-quinolin-4-yl)-ureido]-ethyl}-pyrrolidin-3-yl)-benzenesulfonamide;
N-Ethyl-3-methyl-N-(1-{2-[3-(2-methyl-quinolin-4-yl)-ureido]-ethyl}-piperidin-4-yl)-benzenesulfonamide;
N-Ethyl-4-methyl-N-(1-{2-[3-(2-methyl-quinolin-4-yl)-ureido]-ethyl}-piperidin-4-yl)-benzenesulfonamide;
N-Ethyl-2-methyl-N-(1-{2-[3-(2-methyl-quinolin-4-yl)-ureido]-ethyl}-piperidin-4-yl)-benzenesulfonamide;
3-Chloro-N-ethyl-N-(1-{2-[3-(2-methyl-quinolin-4-yl)-ureido]-ethyl}-piperidin-4-yl)-benzenesulfonamide;
2-Chloro-N-ethyl-N-(1-{2-[3-(2-methyl-quinolin-4-yl)-ureido]-ethyl}-piperidin-4-yl)-benzenesulfonamide;
4-Chloro-N-ethyl-N-(1-{2-[3-(2-methyl-quinolin-4-yl)-ureido]-ethyl}-piperidin-4-yl)-benzenesulfonamide;
N-Ethyl-4-fluoro-N-(1-{2-[3-(2-methyl-quinolin-4-yl)-ureido]-ethyl}-piperidin-4-yl)-benzenesulfonamide;
N-Ethyl-4-methoxy-N-(1-{2-[3-(2-methyl-quinolin-4-yl)-ureido]-ethyl}-piperidin-4-yl)-benzenesulfonamide;
3,4-Dichloro-N-ethyl-N-(1-{2-[3-(2-methyl-quinolin-4-yl)-ureido]-ethyl}-piperidin-4-yl)-benzenesulfonamide;
N-Ethyl-N-(1-{2-[3-(2-methyl-quinolin-4-yl)-ureido]-ethyl}-piperidin-4-yl)-4-trifluoromethyl-benzenesulfonamide;
1-(2-Methyl-quinolin-4-yl)-3-{2-[4-(3-phenethyl-ureido)-piperidin-1-yl]-ethyl}-urea;
1-[(S)-1-(4-Benzyl-piperidin-1-ylmethyl)-2-methyl-propyl]-3-(2-methyl-quinolin-4-yl)-urea;
1-[(S)-1-Benzyl-2-(4-benzyl-piperidin-1-yl)-ethyl]-3-(2-methyl-quinolin-4-yl)-urea;
1-[(S)-1-(4-Benzyl-piperidin-1-ylmethyl)-3-methyl-butyl]-3-(2-methyl-quinolin-4-yl)-urea;
1-[2-(4-Benzyl-4-hydroxy-piperidin-1-yl)-ethyl]-3-(2-cyclopropyl-quinolin-4-yl)-urea;
1-{2-[4-(3-Methyl-benzyl)-piperidin-1-yl]-ethyl}3-(2-methyl-quinolin-4-yl)-urea;
1-{2-[4-(2-Methyl-benzyl)-piperidin-1-yl]-ethyl}3-(2-methyl-quinolin-4-yl)-urea;
1-{2-[4-(4-Fluoro-benzyl)-piperidin-1-yl]-ethyl}-3-(2-methyl-quinolin-4-yl)-urea;
1-{2-[3-(2-Methyl-quinolin-4-yl)-ureido]-ethyl}piperidine-4-carboxylic acid benzyl-phenyl-amide;
1-{2-[3-(2-Methyl-quinolin-4-yl)-ureido]-ethyl}piperidine-4-carboxylic acid (2-chloro-phenyl)-methyl-amide;
1-{2-[3-(2-Methyl-quinolin-4-yl)-ureido]-ethyl}4-phenyl-piperidine-4-carboxylic acid benzyl-methyl-amide;
1-{2-[3-(2-Methyl-quinolin-4-yl)-ureido]-ethyl}4-phenyl-piperidine-4-carboxylic acid methyl-phenethyl-amide;
1-{2-[3-(2-Methyl-quinolin-4-yl)-ureido]-ethyl}4-phenyl-piperidine-4-carboxylic acid benzyl-ethyl-amide;
1-{2-[3-(2-Methyl-quinolin-4-yl)-ureido]-ethyl}4-phenyl-piperidine-4-carboxylic acid dimethylamide;
4-Benzyl-1-{2-[3-(2-methyl-quinolin-4-yl)-ureido]-ethyl}piperidine-4-carboxylic acid benzyl-ethyl-amide;
1-[2-(4-Benzyl-4-hydroxy-piperidin-1-yl)-ethyl]-3-(2-methylamino-pyridin-4-yl)-urea; and
1-[2-(4-Benzyl-piperidin-1-yl)-ethyl]-3-(2-methylamino-pyridin-4-yl)-urea, or a pharmaceutically acceptable salt of said compound.

23. The compound according to claim 1 being 1-[2-(4-Benzyl-4-hydroxy-piperidin-1-yl)-ethyl]-3-(2-methyl-quinolin-4-yl)-urea, or a pharmaceutically acceptable salt thereof.

* * * * *